United States Patent
Riggs-Sauthier et al.

(10) Patent No.: US 9,827,239 B2
(45) Date of Patent: *Nov. 28, 2017

(54) OLIGOMER-OPIOID AGONIST CONJUGATES

(71) Applicant: Nektar Therapeutics, San Francisco, CA (US)

(72) Inventors: Jennifer Riggs-Sauthier, San Francisco, CA (US); Bo-Liang Deng, San Ramon, CA (US); Timothy A. Riley, Worcester, MA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/341,470

(22) Filed: Nov. 2, 2016

(65) Prior Publication Data

US 2017/0112826 A1 Apr. 27, 2017

Related U.S. Application Data

(63) Continuation of application No. 14/959,604, filed on Dec. 4, 2015, now Pat. No. 9,512,135, which is a continuation of application No. 14/581,832, filed on Dec. 23, 2014, now Pat. No. 9,233,168, which is a continuation of application No. 14/032,648, filed on Sep. 20, 2013, now Pat. No. 8,952,032, which is a continuation of application No. 13/386,327, filed as application No. PCT/US2010/042792 on Jul. 21, 2010, now Pat. No. 8,575,196, which is a continuation-in-part of application No. 12/558,395, filed on Sep. 11, 2009, now Pat. No. 8,173,666, which is a continuation-in-part of application No. PCT/US2008/003353, filed on Mar. 12, 2008.

(60) Provisional application No. 61/350,853, filed on Jun. 2, 2010, provisional application No. 61/227,399, filed on Jul. 21, 2009, provisional application No. 61/192,261, filed on Sep. 16, 2008, provisional application No. 60/906,387, filed on Mar. 12, 2007.

(51) Int. Cl.
*A61K 31/485* (2006.01)
*C07D 489/08* (2006.01)
*A61K 47/10* (2017.01)

(52) U.S. Cl.
CPC ............ *A61K 31/485* (2013.01); *A61K 47/10* (2013.01)

(58) Field of Classification Search
CPC ............................. C07D 489/08; A61K 31/485
USPC ...................... 546/44, 45; 514/282
See application file for complete search history.

(56) References Cited

U.S. PATENT DOCUMENTS

| | | |
|---|---|---|
| 2,628,962 A | 2/1953 | Homeyer et al. |
| 2,649,454 A | 8/1953 | Rapoport |
| 2,654,756 A | 10/1953 | Homeyer et al. |
| 2,715,626 A | 8/1955 | Pfister et al. |
| 2,806,033 A | 9/1957 | Lewenstein et al. |
| 3,254,088 A | 5/1966 | Lewenstein et al. |
| 4,632,935 A | 12/1986 | Kaplan |
| 5,240,933 A | 8/1993 | Merz et al. |
| 5,356,907 A | 10/1994 | Clemence et al. |
| 5,428,159 A | 6/1995 | Shieh et al. |
| 5,475,019 A | 12/1995 | Privette et al. |
| 5,672,662 A | 9/1997 | Harris et al. |
| 5,843,900 A | 12/1998 | Cheronis et al. |
| 6,004,577 A | 12/1999 | Murdock |
| 6,645,528 B1 | 11/2003 | Straub et al. |
| 6,858,580 B2 | 2/2005 | Ekwuribe et al. |
| 7,026,134 B2 | 4/2006 | Lamont et al. |
| 7,056,500 B2 | 6/2006 | Bentley et al. |
| 7,109,310 B2 | 9/2006 | McConnell et al. |
| 7,230,005 B2 | 6/2007 | Shafer et al. |
| 7,662,365 B2 | 2/2010 | Bentley et al. |
| 8,034,825 B2 | 10/2011 | Bentley et al. |
| 8,173,666 B2 | 5/2012 | Riggs-Sauthier et al. |
| 8,440,687 B2 | 5/2013 | Riggs-Sauthier et al. |
| 8,569,343 B2 | 10/2013 | Riggs-Sauthier et al. |
| 8,575,196 B2 | 11/2013 | Riggs-Sauthier et al. |
| 8,946,285 B2 | 2/2015 | Riggs-Sauthier et al. |
| 8,952,032 B2 | 2/2015 | Riggs-Sauthier et al. |
| 9,233,167 B2 | 1/2016 | Riggs-Sauthier et al. |
| 9,233,168 B2 | 1/2016 | Riggs-Sauthier et al. |
| 9,458,166 B2 * | 10/2016 | Riggs-Sauthier .... A61K 31/439 |
| 9,512,135 B2 * | 12/2016 | Riggs-Sauthier .... A61K 31/439 |
| 2002/0142050 A1 | 10/2002 | Straub et al. |
| 2003/0095992 A1 | 5/2003 | Erhardt |
| 2004/0062717 A1 | 4/2004 | Rosell et al. |
| 2004/0092531 A1 | 5/2004 | Chizh et al. |

(Continued)

FOREIGN PATENT DOCUMENTS

| | | |
|---|---|---|
| CN | 102060753 | 5/2011 |
| DE | 100 25 946 | 11/2001 |

(Continued)

OTHER PUBLICATIONS

Abreu et al., "Effect of intravenous injection speed on responses to cocaine and hydromorphone in humans," Psychopharmacol., vol. 154, pp. 76-84, (2001).

Adams et al., "Development of a Self-Report Screening Instrument for Assessing Potential Opioid Medication Misuse in Chronic Pain Patients," Journal of Pain and Symptom Management, vol. 27, No. 5, pp. 440-459, (May 2004).

Anderson et al., "Structure-Activity Relationship Assessment of Conjugated Enkephalins in Centrally Mediated Analgesia," Soc. For NeuroSci., (Abstract), vol. 25, pp. 180, (1999).

(Continued)

*Primary Examiner* — Charanjit Aulakh

(57) ABSTRACT

The invention provides compounds that are chemically modified by covalent attachment of a water—soluble oligomer. A compound of the invention, when administered by any of a number of administration routes, exhibits characteristics that are different from those of the compound not attached to the water—soluble oligomer.

18 Claims, 24 Drawing Sheets

(56) References Cited

U.S. PATENT DOCUMENTS

| | | |
|---|---|---|
| 2004/0180036 A1 | 9/2004 | Ashton et al. |
| 2004/0180080 A1 | 9/2004 | Furusawa et al. |
| 2005/0042173 A1 | 2/2005 | Besse et al. |
| 2005/0048116 A1 | 3/2005 | Straub et al. |
| 2005/0136031 A1 | 6/2005 | Bentley et al. |
| 2005/0226922 A1 | 10/2005 | Ameri et al. |
| 2005/0233459 A1 | 10/2005 | Melker et al. |
| 2005/0266070 A1 | 12/2005 | Mickle et al. |
| 2006/0009478 A1 | 1/2006 | Friedmann et al. |
| 2006/0105046 A1 | 5/2006 | Bentley et al. |
| 2007/0003617 A1* | 1/2007 | Fischer ............... A61K 9/0092 424/468 |
| 2007/0083186 A1 | 4/2007 | Carter et al. |
| 2007/0258894 A1 | 11/2007 | Melker et al. |
| 2008/0057074 A1 | 3/2008 | Takaoka et al. |
| 2008/0066741 A1 | 3/2008 | LeMahieu et al. |
| 2008/0076789 A1 | 3/2008 | Stinchcomb et al. |
| 2009/0221766 A1 | 9/2009 | Cheng et al. |
| 2009/0246265 A1 | 10/2009 | Stinchcomb et al. |
| 2010/0016365 A1 | 1/2010 | Gant et al. |
| 2010/0048602 A1 | 2/2010 | Riggs-Sauthier et al. |
| 2011/0021419 A1 | 1/2011 | Zimmer et al. |
| 2011/0165248 A1 | 7/2011 | Machonis |
| 2011/0237614 A1 | 9/2011 | Jude-Fishburn et al. |
| 2012/0184581 A1 | 7/2012 | Riggs-Sauthier et al. |
| 2012/0264775 A1 | 10/2012 | Riggs-Sauthier et al. |
| 2012/0289548 A1 | 11/2012 | Riggs-Sauthier et al. |
| 2013/0023553 A1 | 1/2013 | Jude-Fishburn et al. |
| 2014/0187790 A1 | 7/2014 | Riggs-Sauthier et al. |
| 2014/0200235 A1 | 7/2014 | Riggs-Sauthier et al. |
| 2015/0112069 A1 | 4/2015 | Riggs-Sauthier et al. |
| 2015/0238624 A1 | 8/2015 | Riggs-Sauthier et al. |
| 2016/0130276 A1 | 5/2016 | Riggs-Sauthier et al. |
| 2016/0214990 A1 | 7/2016 | Riggs-Sauthier et al. |
| 2016/0243111 A1 | 8/2016 | Jude-Fishburn et al. |
| 2016/0375009 A1 | 12/2016 | Riggs-Sauthier et al. |

FOREIGN PATENT DOCUMENTS

| | | |
|---|---|---|
| EP | 0 396 282 | 11/1990 |
| EP | 1 312 923 | 5/2003 |
| EP | 1 782 834 | 5/2007 |
| FR | 2.430 | 4/1964 |
| GB | 2 399 286 | 9/2004 |
| JP | 60-149589 A | 7/1985 |
| JP | 2002-275066 | 9/2002 |
| JP | 2005-119987 | 5/2005 |
| WO | WO 92/03122 | 3/1992 |
| WO | WO 94/27967 | 12/1994 |
| WO | WO 96/39425 | 12/1996 |
| WO | WO 97/21416 | 6/1997 |
| WO | WO 98/54196 | 12/1998 |
| WO | WO 00/09073 | 2/2000 |
| WO | WO 00/14089 | 3/2000 |
| WO | WO 00/16751 | 3/2000 |
| WO | WO 01/24831 | 4/2001 |
| WO | WO 02/09707 | 2/2002 |
| WO | WO 02/45713 | 6/2002 |
| WO | WO 02/098427 A2 | 12/2002 |
| WO | WO 02/098949 | 12/2002 |
| WO | WO 03/032914 | 4/2003 |
| WO | WO 03/032990 | 4/2003 |
| WO | WO 03/048081 | 6/2003 |
| WO | WO 03/048158 | 6/2003 |
| WO | WO 03/051113 | 6/2003 |
| WO | WO 03/072561 | 9/2003 |
| WO | WO 2004/037817 | 5/2004 |
| WO | WO 2004/039317 | 5/2004 |
| WO | WO 2004/069198 | 8/2004 |
| WO | WO 2004/082620 | 9/2004 |
| WO | WO 2005/058367 | 6/2005 |
| WO | WO 2005/074913 | 8/2005 |
| WO | WO 2006/030925 | 3/2006 |
| WO | WO 2006/064351 | 6/2006 |
| WO | WO 2006/073396 | 7/2006 |
| WO | WO 2006/086609 | 8/2006 |
| WO | WO 2006/105035 | 10/2006 |
| WO | WO 2006/126529 A1 | 11/2006 |
| WO | WO 2007/007059 | 1/2007 |
| WO | WO 2007/087431 | 8/2007 |
| WO | WO 2007/140272 A2 | 12/2007 |
| WO | WO 2008/023261 | 2/2008 |
| WO | WO 2008/036980 | 3/2008 |
| WO | WO 2008/057579 | 5/2008 |
| WO | WO 2008/112288 | 9/2008 |
| WO | WO 2008/116165 | 9/2008 |
| WO | WO 2008/135283 | 11/2008 |
| WO | WO 2009/017837 | 2/2009 |
| WO | WO 2009/033281 | 3/2009 |
| WO | WO 2009/077584 | 6/2009 |
| WO | WO 2009/094209 | 7/2009 |
| WO | WO 2009/119992 | 10/2009 |
| WO | WO 2009/121997 | 10/2009 |
| WO | WO 2009/151590 | 12/2009 |
| WO | WO 2010/033195 | 3/2010 |
| WO | WO 2010/068789 | 6/2010 |
| WO | WO 2010/101649 | 9/2010 |
| WO | WO 2010/122355 | 10/2010 |
| WO | WO 2011/002995 | 1/2011 |
| WO | WO 2011/011543 | 1/2011 |
| WO | WO 2011/078370 | 6/2011 |
| WO | WO 2011/088140 | 7/2011 |
| WO | WO 2011/088192 | 7/2011 |
| WO | WO 2011/098539 | 8/2011 |

OTHER PUBLICATIONS

Atluri et al., "Development of a Screening Tool to Detect the Risk of Inappropriate Prescription Opioid Use in Patients with Chronic Pain," Pain Physician, vol. 47, pp. 333-338, (2004).

Balster et al., "Fixed-Interval Schedule of Cocaine Reinforcement: Effect of Dose and Infusion Duration," J. Of the Exper. Analy. of Behav., vol. 20, No. 1, pp. 119-129, (Jul. 1973).

Basbaum et al., "Toward Better Pain Control," Scientific American, 4 pages, (Jun. 2006).

Batz et al., "Pharmacologicaly Active Polymers 9th Report: Retard Forms of Morphine Antagonists," Drug Res., pp. 1-18, (1977).

Bennett et al., "Biodegradable polymeric prodrugs of naltrexone," J. of Contr. Rel., vol. 16, pp. 43-52, (1991).

Bergman et al., "Measuring the Reinforcing Strength of Abused Drugs," Mol. Interventions, vol. 6, No. 5, pp. 273-283, (Oct. 2006).

Bostros et al., "Investigation of the Structural Requirements for the κ-Selective Opioid Receptor Antagonist, 6β,6β'-[Ethylenebis(oxyethyleneimino)]bis[17-(cyclopropylmethyl)-4,5α-epoxymorphinan-3,14-diol] (TENA)," J. Med. Chem., vol. 29, pp. 874-876, (1986).

Brower, "New paths to pain relief," Nature Biotechnology, vol. 18, pp. 387-391, (Apr. 2000).

Bush et al., "The K-opioid agonist, asimadoline, alters cytokine gene expression in adjuvant arthritis," Rheumatology, vol. 40, pp. 1013-1021, (2001).

Caudle et al., "GR89,696 Is a Kappa-2 Opioid Receptor Agonist and a Kappa-1 Opioid Receptor Antagonist in the Guinea Pig Hippocampus," The Journal of Pharmacology and Experimental Therapeutics, vol. 283, No. 3, pp. 1342-1349, (1997).

Chatterjie et al., "Reduction of 6-Ketones of the Morphine Series with Formamidinesulfinic Acid Stereoselectivity Opposite to That of Hydride Reductions," J. Org. Chem., vol. 41, No. 22, pp. 3624-3625, (1976).

Chen et al., "Synthesis and Properties of ABA Amphiphiles," J. Org. Chem., vol. 64, pp. 6870-6873, (1999).

Dahlstrom et al., "Pharmacokinetic Interpretation of the Enterohepatic Recirculation and First-Pass Elimination of Morphine in the Rat," J. of Pharmacokinect. and Biopharmaceu., vol. 6, No. 6, pp. 505-519, (1978).

Davankov, "Analytical Chiral Separation Methods," Pure Appl. Chem., vol. 69, No. 7, pp. 1469-1474, (1997).

Dickenson, "Plasticity: Implications for Opioid and Other Pharmacological Interventions in Specific Pain States," Behavioral and Brain Sciences, vol. 20, No. 3, 22 pages, (1997).

(56) References Cited

OTHER PUBLICATIONS

Erez et al., "Narcotic Antagonistic Potency of Bivalent Ligands Which Contain β-Naltrexamine . . . ," J. Med. Chem., vol. 25, pp. 847-849, (1982).
Ertl et al., "Fast Calculation of Molecular Polar Surface Area as a Sum of Fragment-Based Contributions . . . ," J. Med. Chem., vol. 43, pp. 3714-3717, (2000).
Frensch et al., "Oligo Ethylene Glycol Ethers of Morphine," Liebigs Annalen Der Chemie., pp. 2118-2120, (1979).
Fujii et al., "An expedient and selective route to crowned morphine and isomorphine congeners. A probe for ionophore and molecular recognition of opiate receptor," Tetrahedron Letters, vol. 25, No. 31, pp. 3335-3338, (1984).
Fukuda et al., "Partial Agonistic Activity of Naloxone on the Opioid Receptors Expressed from Complementary Deoxyribonucleic Acids in Chinese Hamster Ovary Cells," Anesth. Analg., vol. 87, pp. 450-455, (1998).
Gasior et al., "Evaluation of the Reinforcing Effects of Monoamine Reuptake Inhibitors Under a Concurrent Schedule of Food and I.V. Drug Delivery in Rhesus Monkeys," Neuropsychopharmacology, vol. 30, pp. 758-764, (2005).
Griffiths et al., "Predicting the Abuse Liability of Drugs with Animal Drug Self-Administration Procedures: Psychomotor Stimulants and Hallucinogens," Advances in Behavioral Pharmacology, vol. 2, pp. 163-208, (1979).
Guiotto et al., "Anchimeric assistance effect on regioselective hydrolysis of branched PEGs: a mechanistic investigation," Bioorg. & Med. Chem., vol. 12, pp. 5031-5037, (2004).
Harris et al., "Effect of Pegylation on Pharmaceuticals," Nature, vol. 2, pp. 214-221, (Mar. 2003).
Johanson et al., "A summary of the results of a drug self-administration study using substitution procedures in rhesus monkeys," Bulletin on Narcotics, vol. 30, No. 3, pp. 43-54, (Jul.-Sep. 1978).
Johansson et al., "Affinity Partitioning of Biopolymers and Membranes in Ficoll-Dextran Aqueous Two-Phase Systems," Journal of Chromatography, vol. 331, pp. 11-21, (1985).
Johansson et al., "Effect of some poly(ethylene glycol)-bound and dextran-bound affinity ligands on the partition of synaptic membranes in aqueous two-phase systems," J. of Chromatog. B., vol. 652, pp. 137-147, (1994).
Kelder et al., "Polar Molecular Surface as a Dominating Determinant for Oral Absorption and Brain Penetration of Drugs," Pharmaceu. Res., vol. 16, No. 10, pp. 1514-1519, (1999).
Kinouchi et al., "Evidence for KI opioid receptor multiplicity in the guinea pig cerebellum," Euro. J. of Pharmacol., Mol. Pharma. Sec., vol. 207, pp. 135-141, (1991).
Ko et al., "Relative Reinforcing Effects of Three Opioids with Different Durations of Action," The J. of Pharmacol. and Exper. Therap., vol. 301, No. 2, pp. 698-704, (2002).
Lahti et al., "[3H]U-69593 A Highly Selective Ligand for the Opioid K Receptor," Euro. J. of Pharmacol., vol. 109, pp. 281-284, (1985).
Lenz et al., "Stereoselective Reduction of Codeinone, the Penultimate Enzymic Step During Morphine Biosynthesis in Papaver somniferum," Tetra. Lett., vol. 36, No. 14, pp. 2449-2452, (1995).
Lobbezoo et al., "Opiate Receptor Interaction of Compounds Derived from or Structurally Related to Fentanyl," J. Med. Chem., vol. 24, pp. 777-782, (1981).
Mahkam et al., "Preparation of new biodegradable polyurethanes as a therapeutic agent," Poly. Degrad. and Stab., vol. 80, pp. 199-202, (2003).
Malatynska et al., "Human δ opioid receptor: a stable cell line for functional studies of opioids," NeuroReport, vol. 6, pp. 613-616, (1995).
Malspeis et al., "Metabolic Reduction of Naltrexone I. Synthesis, Separation and Characterization of Naloxone and Naltrexone . . . ," Res. Commun. Chem. Pathol. and Pharmacol., vol. 12, No. 1, pp. 43-65, (Sep. 1975).
Manchikanti et al., "Monitoring Opioid Adherence in Chronic Pain Patients: Tools, Techniques, and Utility," Pain Physician, Opioids Special Issue, vol. 11, pp. S155-S180, (2008).
Metcalf et al., "Kappa Opioid Antagonists: Past Successes and Future Prospects," The AAPS Journal, vol. 7, No. 3, pp. E704-E722, (2005).
Nath et al., "Morphine-induced straub tail response: mediated by central $\mu_2$-opioid receptor," European Journal of Pharmacology, vol. 263, pp. 203-205, (1994).
Neilan et al., "Characterization of the Binding of [$^3$H][Dmt$^1$]H-Dmt-$_D$-Arg-Phe-Lys-NH$_2$, a Highly Potent Opioid Peptide," The Journal of Pharmacology and Experimental Therapeutics, vol. 306, No. 2, pp. 430-436, (2003).
Okuda et al., "Prolonged Antinociceptive Effect after Epidural Injection of Polyethylene Glycol-Morphine Composites in Rats," Masui-JP, J. of Anesthesiology with English Abstract, vol. 45, No. 5, pp. 571-575, (Jan. 1, 1996).
Olde et al., "Affinity Partitioning and Centrifugal Counter-Current Distribution of Membrane-Bound Opiate Receptors Using Naloxone-Poly(Ethylene Glycol),"NeuroSci., vol. 15, No. 4, pp. 1247-1253, (1985).
Panlilio et al., "Self-administration of remifentanil, an ultra-short acting opioid, under continuous and progressive-ratio schedules of reinforcement in rats," Psychopharmacol., vol. 150, pp. 61-66, (2000).
Rothman et al., "Interaction of Opioid Peptides and Other Drugs With Multiple Kappa Receptors in Rat and Human Brain. Evidence for Species Differences," Peptides, vol. 13, pp. 977-987, (1992).
Rubin, "The Cell Biology of the Blood-Brain Barrier," Annu. Rev. Neurosci., vol. 22, pp. 11-28, (1999).
Summerfield et al., "Central Nervous System Drug Disposition: . . . ," The J. of Pharmacol. and Exper. Therap., vol. 322, No. 1, pp. 205-213, & pp. 971-972 SUPP sheets regarding correction on the article, (2007).
Tsuji, "Small Molecular Drug Transfer across the Blood-Brain Barrier via Carrier-Mediated Transport Systems," The Amer. Soc. for Exper. NeuroTherap., vol. 2, pp. 54-62, (Jan. 2005).
Wang et al., "Comparison of Pharmacological Activities of Three Distinct $_\kappa$ Ligands (Salvinorin A, TRK-820 and 3FLB) on $_\kappa$ Opioid Receptors in Vitro and Their Antipruritic and Antinociceptive Activities in Vivo," The J. of Pharmacol. and Exp. Therap., vol. 312, No. 1, pp. 220-230, (2005).
Winger et al., "Relative Reinforcing Strength of Three N-Methyl-D-Aspartate Antagonists with Different Onsets of Action," The J. of Pharmacol. and Exper. Therap., vol. 301, No. 2, pp. 690-697, (2002).
Witt et al., "Pharmacodynamic and Pharmacokinetic Characterization of Poly(Ethylene Glycol) . . . ," The J. of Pharmacol. and Exper. Therap., vol. 298, No. 2, pp. 848-856, (2001).
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).

(56) References Cited

OTHER PUBLICATIONS

Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
PCT International Search Report in PCT Application No. PCT/US2008/003353 dated Nov. 5, 2008.
PCT International Preliminary Report on Patentability in PCT Application No. PCT/US2008/003353 dated Sep. 24, 2009.
PCT International Search Report in PCT Application No. PCT/US2010/042792 dated Oct. 26, 2010.
PCT International Preliminary Report on Patentability in PCT Application No. PCT/US2010/042792 dated Feb. 2, 2012.
PCT International Search Report and Written Opinion in PCT Application No. PCT/US2009/005174 dated Feb. 25, 2010.
PCT International Preliminary Report on Patentability in PCT Application No. PCT/US2009/005174 dated Mar. 31, 2011.
PCT International Search Report and Written Opinion in PCT Application No. PCT/US2011/021017 dated Mar. 22, 2011.
PCT International Preliminary Report on Patentability in PCT Application No. PCT/US2011/021017 dated Jul. 26, 2012.
U.S. Notice of Allowability in U.S. Appl. No. 12/558,395 dated Mar. 12, 2012.
U.S. Notice of Allowability in U.S. Appl. No. 13/426,521 dated Jan. 14, 2013.
U.S. Office Action Summary in U.S. Appl. No. 13/426,521 dated Sep. 17, 2012.
U.S. Office Action Summary in U.S. Appl. No. 13/538,540 dated Mar. 4, 2013.
U.S. Notice of Allowability in U.S. Appl. No. 13/538,540 dated Jun. 21, 2013.
Australian Patent Examination Report No. 1 in Australian Patent Application No. 2008226822 dated Jun. 28, 2012.
Australian Patent Examination Report No. 1 in Australian Patent Application No. 2010276244 dated Jul. 15, 2014.
Australian Patent Examination Report No. 1 in Australian Patent Application No. 2009292631 dated Mar. 31, 2014.
Canadian Office Action in Canadian Patent Application No. 2,679,479 dated Jul. 5, 2013.
Canadian Office Communication in Canadian Patent Application No. 2,679,479 dated May 15, 2014.
Office Action in Canadian Patent Application No. 2,734,333 dated Apr. 30, 2015.
Office Communication in Canadian Patent Application No. 2,734,333 dated Dec. 14, 2015.
English Translation of Notification of the First Office Action in Chinese Patent Application No. 200880007968.X dated Jun. 8, 2011.
English Translation of Notification of the Second Office Action in Chinese Patent Application No. 200880007968.X dated Mar. 19, 2012.
English Translation of Notification of the Third Office Action in Chinese Patent Application No. 200880007968.X dated Aug. 28, 2012.
English Translation of Chinese Notification of the First Office Action in Chinese Patent Application No. 201080037610.9 dated Feb. 20, 2013.
English Translation of Chinese Notification of the Second Office Action in Chinese Patent Application No. 201080037610.9 dated Dec. 6, 2013.
English translation of Chinese Rejection Decision in Chinese Patent Application No. 201080037610.9 dated Jul. 31, 2014.
English Translation of Chinese Notification of the First Office Action in Chinese Patent Application No. 200980136089.1 dated Mar. 23, 2012.
English Translation of Chinese Notification of the Second Office Action in Chinese Patent Application No. 200980136089.1 dated Feb. 18, 2013.
English Translation of Chinese Notification of the Third Office Action in Chinese Patent Application No. 200980136089.1 dated Nov. 8, 2013.
English translation of Chinese Rejection Decision in Chinese Patent Application No. 200980136089.1 dated Jul. 23, 2014.
English Translation of Notification of Reexamination in Chinese Patent Application No. 200980136089.1 dated Nov. 10, 2015.
English Translation of Notification of Reexamination in Chinese Patent Application No. 201080037610.9 dated Oct. 30, 2015.
European Communication in European Patent Application No. 08 742 082.4-1216 dated Feb. 10, 2011.
European Communication in European Patent Application No. 08 742 082.4-1216 dated Sep. 22, 2011.
European Communication in European Patent Application No. 08 742 082.4-1216 dated Mar. 14, 2012.
European Communication in European Patent Application No. 08 742 082.4 dated Nov. 9, 2012.
European Communication in European Patent Application No. 08 742 082.4 dated Jan. 25, 2013.
European Communication in European Patent Application No. 10 735 413 dated Nov. 5, 2012.
European Communication in European Patent Application No. 09 789 323.4 dated Feb. 14, 2012.
European Search Report in European Patent Application No. 13155670.6 dated Jul. 8, 2013.
European Extended Search Report in European Patent Application No. 13155667.2 dated Jul. 1, 2013.
European Communication in European Patent Application No. 13167519.1 dated Jul. 17, 2013.
Office Communication in European Patent Application No. 09 789 323.4-1453 dated Oct. 21, 2015.
Office Communication in European Patent Application No. 13 155 667.2-1453 dated Nov. 23, 2015.
Office Communication in European Patent Application No. 13 167 519.1-1453 dated Jul. 8, 2014.
English Translation of Israel First Substantive Examination Report in Israel Patent Application No. 200845 dated Jul. 22, 2012.
English Translation of Israel Office Action in Israel Patent Application No. 200845 dated Nov. 25, 2013.
English translation of Israel Office Communication in Israel Patent Application No. 200845 dated Aug. 13, 2014.
English translation of Israel Office Communication in Israel Patent Application No. 217634 dated Jan. 21, 2015.
English translation of Israel Office Communication in Israel Patent Application No. 211762 dated Jan. 21, 2015.
English translation of Office Communication in Israeli Patent Application No. 217634 dated Jun. 8, 2016.
English Translation of Japanese Notice of Reasons for Rejection in Japanese Patent Application No. 2009-553629 dated Nov. 9, 2012.
English translation of Japanese Notice of Reasons for Rejection in Japanese Patent Application No. 2012-521761 dated Jul. 24, 2014.
English Translation of Notice of Final Rejection in Japanese Patent Application No. 2012-521761 dated Mar. 12, 2015.
English translation of Japanese Notice of Reasons for Rejection in Japanese Patent Application No. 2011-526872 dated Mar. 3, 2014.
English translation of Japanese Notice of Reasons for Rejection in Japanese Patent Application No. 2011-526872 dated Feb. 23, 2015.
English Translation of Notice of Reasons for Rejection in Japanese Patent Application No. 2013-099473 dated May 20, 2015.

(56) References Cited

OTHER PUBLICATIONS

English Translation of Notice of Reasons for Rejection in Japanese Patent Application No. 2011-526872 dated Jun. 18, 2015.
English translation of Korean Notice of Grounds for Rejection in Korean Patent Application No. 2009-7018448 dated Aug. 1, 2014.
English Translation of Notice of Final Rejection in Korean Patent Application No. 2009-7018448 dated Apr. 8, 2015.
English Translation of Notice of Grounds for Rejection in Korean Patent Application No. 2011-7004392 dated Feb. 1, 2016.
English Translation of Mexican Office Action in Mexican Patent Application No. MX/a/2012/000980 dated Nov. 1, 2013.
English Translation of Communication of the substantive examination report in Mexican Patent Application No. MX/a/2011/002748 dated Nov. 4, 2015.
Kovacs et al., "Site-specific acid-base properties of pholcodine and related compounds", Anal. Bioanal. Chem., vol. 386, pp. 1709-1716, (2006).
Ohta et al., "Studies on Fentanyl and Related Compounds IV. Chromatographic and Spectrometric Discrimination of Fentanyl and its Derivatives", Journal of Analytical Toxicology, Vol, 23, pp. 280-285, (Jul./Aug. 1999).
Communication in Canadian Patent Application No. 2,768,392 dated Jun. 21, 2016.
English translation of Examination Report in Indian Patent Application No. 5550/DELNP/2009 dated Oct. 24, 2016.
English translation of Notice of Grounds for Rejection in Korean Patent Application No. 2012-7004344 dated Nov. 21, 2016.

\* cited by examiner

|  | A / B | | | C / D | | |
|---|---|---|---|---|---|---|
|  | Mean | SD | N | Mean | SD | N |
| Morphine | 0.97 | 0.019 | 3 |  |  |  |
| α-6-mPEG$_1$-O-Morphine | 1.19 | 0.341 | 3 |  |  |  |
| α-6-mPEG$_2$-O-Morphine | 0.31 | 0.019 | 3 |  |  |  |
| α-6-mPEG$_3$-O-Morphine | 0.35 | 0.057 | 3 |  |  |  |
| α-6-mPEG$_4$-O-Morphine | 0.34 | 0.023 | 3 |  |  |  |
| α-6-mPEG$_5$-O-Morphine | 0.53 | 0.179 | 3 |  |  |  |
| α-6-mPEG$_6$-O-Morphine | 0.37 | 0.016 | 3 |  |  |  |
| α-6-mPEG$_7$-O-Morphine | 0.36 | 0.050 | 3 |  |  |  |
| α-6-mPEG$_9$-O-Morphine | 0.25 | 0.067 | 3 |  |  |  |
| Atenolol |  |  |  | 0.060 | 0.008 | 3 |

| Molecule | Brain:plasma ratios | | | | | |
|---|---|---|---|---|---|---|
| | A / B | | | C / D | | |
| | Mean | SD | N | Mean | SD | N |
| Codeine | 2.88 | 0.276 | 3 | | | |
| α-6-mPEG$_1$-O-Codeine | 1.06 | 0.214 | 3 | | | |
| α-6-mPEG$_2$-O-Codeine | 0.24 | 0.014 | 3 | | | |
| α-6-mPEG$_3$-O-Codeine | 0.14 | 0.011 | 3 | | | |
| α-6-mPEG$_4$-O-Codeine | 0.12 | 0.009 | 3 | | | |
| α-6-mPEG$_5$-O-Codeine | 0.16 | 0.049 | 3 | | | |
| α-6-mPEG$_6$-O-Codeine | 0.21 | 0.006 | 3 | | | |
| α-6-mPEG$_7$-O-Codeine | 0.30 | 0.017 | 3 | | | |
| α-6-mPEG$_9$-O-Codeine | 0.31 | 0.047 | 3 | | | |
| Atenolol | | | | 0.060 | 0.013 | 3 |

| Molecule | Brain:plasma ratios | | | | | |
|---|---|---|---|---|---|---|
| | A / B | | | C / D | | |
| | Mean | SD | N | Mean | SD | N |
| Oxycodone | 3.63 | 0.073 | 3 | | | |
| α-6-mPEG$_1$-O-Hydroxycodone | 0.47 | 0.108 | 3 | | | |
| α-6-mPEG$_2$-O-Hydroxycodone | 0.18 | 0.008 | 3 | | | |
| α-6-mPEG$_3$-O-Hydroxycodone | 0.10 | 0.006 | 3 | | | |
| α-6-mPEG$_4$-O-Hydroxycodone | 0.12 | 0.028 | 3 | | | |
| α-6-mPEG$_5$-O-Hydroxycodone | 0.21 | 0.029 | 3 | | | |
| α-6-mPEG$_6$-O-Hydroxycodone | 0.29 | 0.026 | 3 | | | |
| α-6-mPEG$_7$-O-Hydroxycodone | 0.29 | 0.020 | 3 | | | |
| α-6-mPEG$_9$-O-Hydroxycodone | 0.27 | 0.039 | 3 | | | |
| Atenolol | | | | 0.059 | 0.015 | 3 |

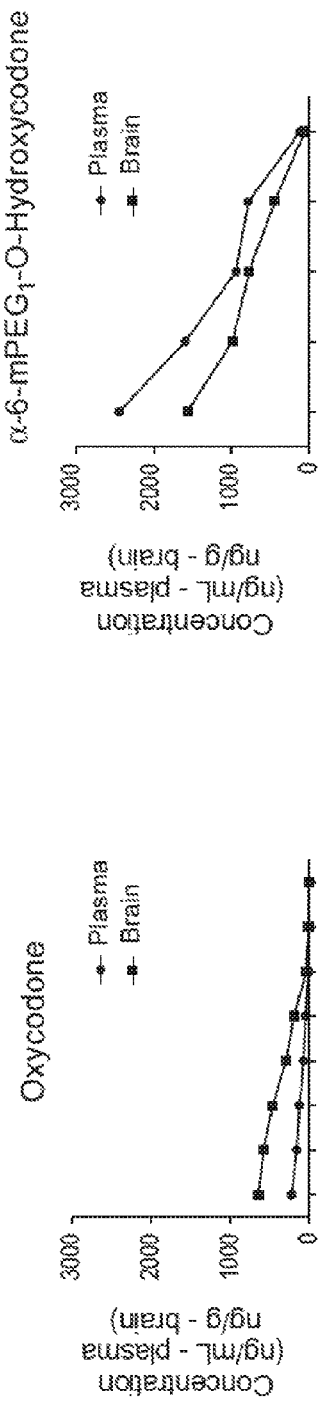
FIG. 19A
FIG. 19B
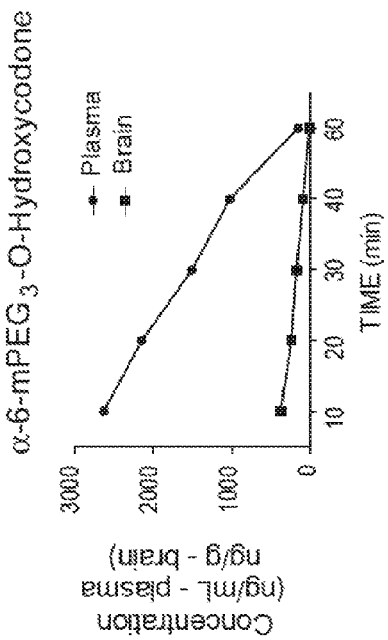
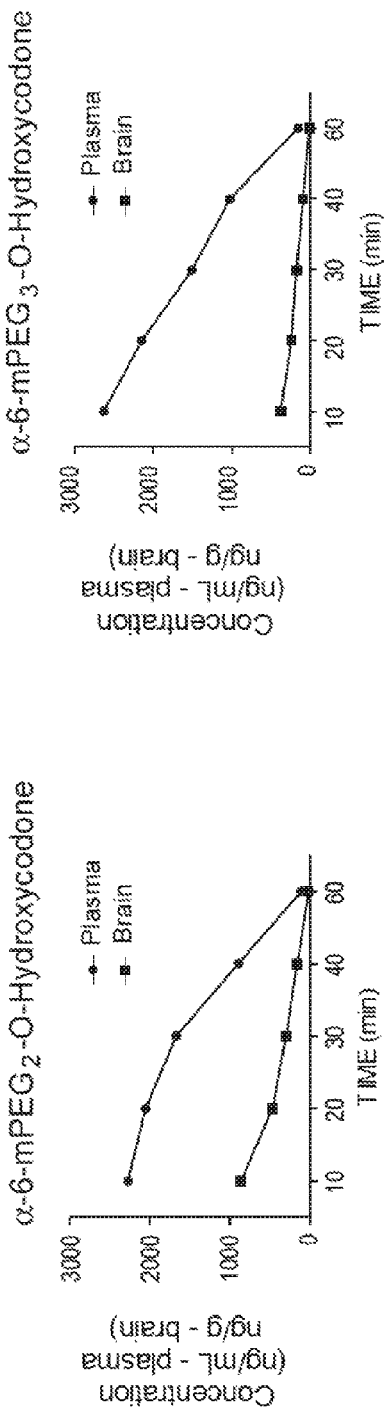
Fig. 19D
FIG. 19C

OLIGOMER-OPIOID AGONIST CONJUGATES

FIELD

This invention provides (among other things) chemically modified opioid agonists that possess certain advantages over opioid agonists lacking the chemical modification. The chemically modified opioid agonists described herein relate to and/or have application(s) in (among others) the fields of drug discovery, pharmacotherapy, physiology, organic chemistry and polymer chemistry.

BACKGROUND

Opioid agonists, such as morphine, have long been used to treat patients suffering from pain. Opioid agonists exert their analgesic and other pharmacological effects through interactions with opioid receptors, of which, there are three main classes: mu (μ) receptors, kappa (κ) receptors, and delta (δ) receptors. Most of the clinically used opioid agonists are relatively selective for mu receptors, although opioid agonists typically have agonist activity at other opioid receptors (particularly at increased concentrations).

Opioids exert their effects by selectively inhibiting the release of neurotransmitters, such as acetylcholine, norepinephrine, dopamine, serotonin, and substance P.

Pharmacologically, opioid agonists represent an important class of agents employed in the management of pain. Unfortunately, the use of opioid agonists is associated with the potential for abuse. In addition, oral administration of opioid agonists often results in significant first pass metabolism. Furthermore, administration of opioid agonists results in significant CNS-mediated effects, such as slowed breathing, which can result in death. Thus, a reduction of any one of these or other characteristics would enhance their desirability as therapeutic drugs.

The present disclosure seeks to address these and other needs in the art by providing (among other things) a conjugate of a water-soluble, non-peptidic oligomer and a opioid agonist.

SUMMARY

In one or more embodiments of the invention, a compound is provided, the compound comprising a residue of an opioid agonist covalently attached (preferably via a stable linkage) to a water-soluble, non-peptidic oligomer.

In one or more embodiments of the invention, a compound is provided, the compound comprising a residue of a kappa opioid agonist covalently attached (preferably via a stable linkage) to a water-soluble, non-peptidic oligomer [wherein it is understood that a kappa opioid agonist (i) is preferentially selective for kappa opioid receptors over both mu opioid receptors and delta opioid receptors within the same mammalian species, and (ii) will have agonist activity at the kappa receptor].

In one or more embodiments of the invention, a compound is provided, the compound comprising a residue of a mu opioid agonist covalently attached (preferably via a stable linkage) to a water-soluble, non-peptidic oligomer [wherein it is understood that a kappa opioid agonist (i) is preferentially selective for mu opioid receptors over both kappa opioid receptors and delta opioid receptors within the same mammalian species, and (ii) will have agonist activity at the mu receptor].

In one or more embodiments of the invention, a compound is provided, the compound comprising a residue of an opioid agonist covalently attached via a stable linkage to a water-soluble, non-peptidic oligomer, wherein the opioid agonist has a structure encompassed by the following formula:

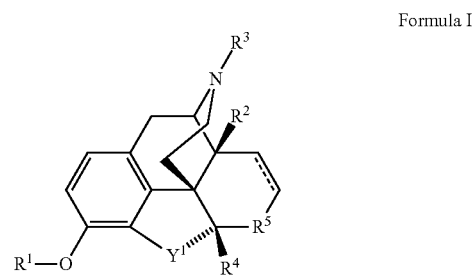

Formula I wherein:
$R^1$ is H or an organic radical [such as methyl, ethyl and —C(O)CH$_3$];
$R^2$ is H or OH;
$R^3$ is H or an organic radical;
$R^4$ is H or an organic radical;
the dotted line (" - - - ") represents an optional double bond;
$Y^1$ is O (oxygen) or S; and
$R^5$ is selected from the group consisting of

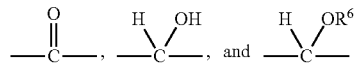

(without regard to stereochemistry), wherein $R^6$ is an organic radical [including —C(O)CH$_3$].

In one or more embodiments of the invention, a compound is provided, the compound comprising a residue of an opioid agonist covalently attached via a stable or degradable linkage to a water-soluble, non-peptidic oligomer, wherein the opioid agonist is selected from the group consisting of asimadoline, bremazocine, enadoline, ethylketocyclazocine, GR89,696, ICI204448, ICI197067, PD117,302, nalbuphine, pentazocine, quadazocine (WIN 44,441-3), salvinorin A, spiradoline, TRK-820, U50488, and U69593.

In one or more embodiments of the invention, a composition is provided, the composition comprising:
(i) a compound comprising a residue of an opioid agonist covalently attached via a stable linkage to a water-soluble, non-peptidic oligomer; and
(ii) optionally, a pharmaceutically acceptable excipient.

In one or more embodiments of the invention, a dosage form is provided, the dosage form comprising a compound comprising a residue of an opioid agonist covalently attached via a stable linkage to a water-soluble, non-peptidic oligomer.

In one or more embodiments of the invention, a method is provided, the method comprising covalently attaching a water-soluble, non-peptidic oligomer to an opioid agonist.

In one or more embodiments of the invention, a method is provided, the method comprising administering a compound comprising a residue of an opioid agonist covalently attached via a stable linkage to a water-soluble, non-peptidic oligomer.

In one or more embodiments of the invention, a method is provided, the method comprising binding (e.g., selectively binding) mu opioid receptors, wherein said binding is achieved by administering a compound comprising a residue of an opioid agonist covalently attached to a water-soluble, non-peptidic oligomer. In one or more embodiments of the invention, a method is provided, the method comprising binding (e.g., selectively binding) mu opioid receptors, wherein said binding is achieved by administering an effective amount of a compound comprising a residue of an opioid agonist covalently attached to a water-soluble, non-peptidic oligomer to a mammalian patient.

In one or more embodiments of the invention, a method is provided, the method comprising binding (e.g., selectively binding) kappa opioid receptors, wherein said binding is achieved by administering a compound comprising a residue of an opioid agonist covalently attached to a water-soluble, non-peptidic oligomer. In one or more embodiments of the invention, a method is provided, the method comprising binding (e.g., selectively binding) kappa opioid receptors, wherein said binding is achieved by administering an effective amount of a compound comprising a residue of an opioid agonist covalently attached to a water-soluble, non-peptidic oligomer to a mammalian patient.

These and other objects, aspects, embodiments and features of the invention will become more fully apparent when read in conjunction with the following detailed description.

BRIEF DESCRIPTION OF THE DRAWINGS

As shown in FIG. 1, binding affinity decreases as a function of PEG chain length at the mu and kappa opioid receptors, but not at the delta opioid receptors, thereby demonstrating that PEG conjugation differently affects binding at these opioid receptor subtypes.

FIG. 7 provides results for mPEG$_{1-5}$-O-hydroxycodone conjugates as well as for unconjugated parent molecule; FIG. 8 provides results for mPEG$_{1-5}$-O-morphine conjugates as well for unconjugated parent molecule; and FIG. 9 provides results for mPEG$_{2-5, 9}$-O-codeine conjugates as well as for the parent molecule. The presence of an asterisk by a data point indicates $p<0.05$ versus saline by ANOVA/Dunnett's.

FIG. 17A (morphine, n=0); FIG. 17B (n=1); FIG. 17C (n=2); FIG. 17D (n=3); FIG. 17E (n=4); FIG. 17F (n=5); FIG. 17G (n=6); FIG. 17H (n=7).

FIG. 18A (codeine, n=0); FIG. 18B (n=1); FIG. 18C (n=2); FIG. 18D (n=3); FIG. 18E (n=4); FIG. 18F (n=5); FIG. 18G (n=6); FIG. 18H (n=7).

FIGS. 19A-H illustrate brain and plasma concentrations of oxycodone and various mPEG$_n$-O-hydroxycodone conjugates over time following IV administration to rats as described in Example 27. FIG. 19A (oxycodone, n=0); FIG. 19B (n=1); FIG. 19C (n=2); FIG. 19D (n=3); FIG. 19E (n=4); FIG. 19F (n=5); FIG. 19G (n=6); FIG. 19H (n=7).

DETAILED DESCRIPTION

Figure 1:
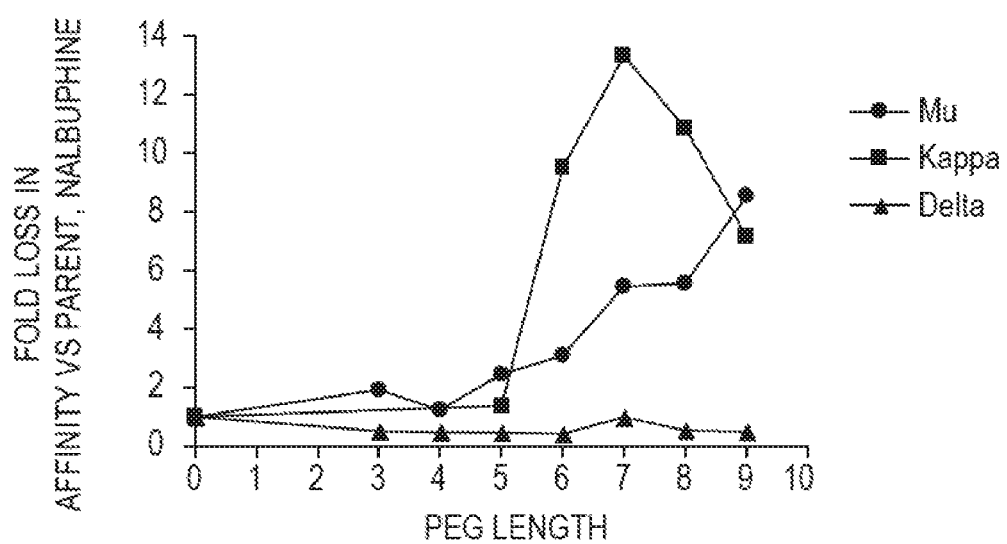
FIG. 1 is a graph showing the fold changes in binding affinity for mu, kappa, and delta receptors over parent molecule, nalbuphine, plotted as a function of PEG length for PEG-nalbuphine conjugates, as described in greater detail in Example 4.

As used in this specification, the singular forms "a," "an," and "the" include plural referents unless the context clearly dictates otherwise.

In describing and claiming the present invention, the following terminology will be used in accordance the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 2 to about 50 monomers, preferably from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" (also called an oligoethylene glycol) is one in which substantially all (and more preferably all) monomeric subunits are ethylene oxide subunits. The oligomer may, however, contain distinct end capping moieties or functional groups, e.g., for conjugation. Typically, PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether the terminal oxygen(s) has been displaced, e.g., during a synthetic transformation. For PEG oligomers, "n" varies from about 2 to 50, preferably from about 2 to about 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

An "end capping group" is generally a non-reactive carbon-containing group attached to a terminal oxygen of a PEG oligomer. Exemplary end capping groups comprise a $C_{1-5}$ alkyl group, such as methyl, ethyl and benzyl), as well as aryl, heteroaryl, cyclo, heterocyclo, and the like. For the purposes of the present invention, the preferred capping groups have relatively low molecular weights such as methyl or ethyl. The end-capping group can also comprise a detectable label. Such labels include, without limitation, fluorescers, chemiluminescers, moieties used in enzyme labeling, colorimetric labels (e.g., dyes), metal ions, and radioactive moieties.

"Branched", in reference to the geometry or overall structure of an oligomer, refers to an oligomer having two or more polymers representing distinct "arms" that extend from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under ordinary physiological conditions. The tendency of a bond to hydrolyze in water under ordinary physiological conditions will depend not only on the general type of linkage connecting two central atoms but also on the substituents attached to these central atoms. Such bonds are generally recognizable by those of ordinary skill in the art. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes under ordinary physiological conditions.

A "stable" linkage or bond refers to a chemical moiety or bond, typically a covalent bond, that is substantially stable in water, that is to say, does not undergo hydrolysis under ordinary physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under ordinary physiological conditions. Hydrolysis rates of representative chemical bonds can be found in most standard chemistry textbooks.

In the context of describing the consistency of oligomers in a given composition, "substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially comprising molecules having a single and definable number of monomers rather than several different numbers of monomers (i.e., an oligomer composition having three or more different oligomer sizes). A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a distribution and would possess a MW/Mn value of 1.0005, and more preferably, a MW/Mn value of 1.0000 if the oligomer were not attached to the residue of the opioid agonist. A composition comprised of monodisperse conjugates can include, however, one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the residue of the opioid agonist. A composition comprised of bimodal conjugates can include, however, one or more nonconjugate substances such as solvents, reagents, excipients, and so forth.

An "opioid agonist" is broadly used herein to refer to an organic, inorganic, or organometallic compound typically having a molecular weight of less than about 1000 Daltons (and typically less than 500 Daltons) and having some degree of activity as a mu and/or kappa agonist. Opioid agonists encompass oligopeptides and other biomolecules having a molecular weight of less than about 1000.

A "biological membrane" is any membrane, typically made from specialized cells or tissues, that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth. Unless the context clearly dictates otherwise, the term "biological membrane" does not include those membranes associated with the middle gastro-intestinal tract (e.g., stomach and small intestines).

A "biological membrane crossing rate," as used herein, provides a measure of a compound's ability to cross a biological membrane (such as the membrane associated with the blood-brain barrier). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known in the art, described herein and/or in the relevant literature, and/or can be determined by one of ordinary skill in the art.

A "reduced rate of metabolism" in reference to the present invention, refers to a measurable reduction in the rate of metabolism of a water-soluble oligomer-small molecule drug conjugate as compared to rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and must pass through the liver prior to reaching the systemic circulation. Because the liver is the primary site of drug metabolism or biotransformation, a substantial amount of drug can be metabolized before it ever reaches the systemic circulation. The degree of first pass metabolism, and thus, any reduction thereof, can be measured by a number of different approaches. For instance, animal blood samples can be collected at timed intervals and the plasma or serum analyzed by liquid chromatography/mass spectrometry for metabolite levels. Other techniques for measuring a "reduced rate of metabolism" associated with the first pass metabolism and other metabolic processes are known in the art, described herein and/or in the relevant literature, and/or can be determined by one of ordinary skill in the art. Preferably, a conjugate of the invention can provide a reduced rate of metabolism reduction satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to component that can be included in the compositions of the invention in order to provide for a composition that has an advantage (e.g., more suited for administration to a patient) over a composition lacking the component and that is recognized as not causing significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

An "aromatic-containing moiety" is a collection of atoms containing at least aryl and optionally one or more atoms. Suitable aromatic-containing moieties are described herein.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a threshold level of active agent and/or conjugate in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, typically, but not necessarily, in the form of a water-soluble oligomer-small molecule drug conjugate, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a residue of an opioid agonist covalently attached via a stable or degradable linkage to a water-soluble, non-peptidic oligomer.

In one or more embodiments of the invention, a compound is provided, the compound comprising a residue of an opioid agonist covalently attached via a stable or degradable linkage to a water-soluble, non-peptidic oligomer, wherein the opioid agonist has a structure encompassed by the following formula:

Formula I

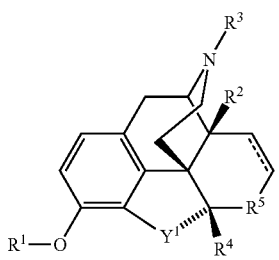

wherein:
R¹ is H or an organic radical [such as methyl, ethyl and —C(O)CH₃];
R² is H or OH;
R³ is H or an organic radical;
R⁴ is H or an organic radical;
the dotted line (" - - - ") represents an optional double bond;
Y¹ is O or S; and
R⁵ is selected from the group consisting of

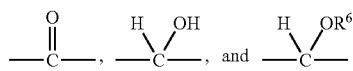

(without regard to stereochemistry), wherein R⁶ is an organic radical [including C(O)CH₃]. Exemplary R³ groups include lower alkyl such as methyl, ethyl, isopropyl, and the like, as well as the following:

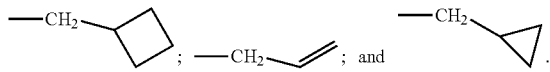

In one or more embodiments of the invention, a compound is provided, the compound comprising a residue of an opioid agonist covalently attached via a stable or degradable linkage to a water-soluble, non-peptidic oligomer, wherein the opioid agonist has a structure encompassed by the following formula:

Formula II

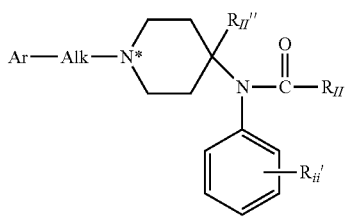

wherein:
N* is nitrogen;
Ar is selected from the group consisting of cyclohexyl, phenyl, halophenyl, methoxyphenyl, aminophenyl, pyridyl, furyl and thienyl;
Alk is selected from the group consisting of ethylene and propylene;
$R_{II}$ is selected from the group consisting of lower alkyl, lower alkoxy, dimethylamino, cyclopropyl, 1-pyrrolidyl, morpholino (preferably lower alkyl such as ethyl);

$R_{II}'$ is selected from the group consisting of hydrogen, methyl and methoxy; and
$R_{II}''$ is selected from the group consisting of hydrogen and an organic radical (preferably lower alkyl).

With respect to Formula II, it will be understood that, depending on the conditions, one or both of the amines—but more typically, the amine marked with an asterisk ("N*") in Formula II—can be protonated.

Examples of specific opioid agonists include those selected from the group consisting acetorphine, acetyldihydrocodeine, acetyldihydrocodeinone, acetylmorphinone, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydroxycodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol. In certain embodiments, the opioid agonist is selected from the group consisting of hydrocodone, morphine, hydromorphone, oxycodone, codeine, levorphanol, meperidine, methadone, oxymorphone, buprenorphine, fentanyl, dipipanone, heroin, tramadol, nalbuphine, etorphine, dihydroetorphine, butorphanol, levorphanol.

It is believed that an advantage of the compounds of the present invention is their ability to retain some degree of opioid agonist activity while also exhibiting a decrease in metabolism and/or resulting in a decrease of CNS-mediated effects associated with the corresponding opioid agonist in unconjugated form. Although not wishing to be bound by theory, it is believed that the oligomer-containing conjugates described herein—in contrast to the unconjugated "original" opioid agonist—are not metabolized as readily because the oligomer serves to reduce the overall affinity of the compound to substrates that can metabolize opioid agonists. In addition (and again, not wishing to be bound by theory), the extra size introduced by the oligomer—in contrast to the unconjugated "original" opioid agonist—reduces the ability of the compound to cross the blood-brain barrier.

Use of oligomers (e.g., from a monodisperse or bimodal composition of oligomers, in contrast to relatively impure compositions) to form the conjugates of the invention can advantageously alter certain properties associated with the corresponding small molecule drug. For instance, a conjugate of the invention, when administered by any of a number of suitable administration routes, such as parenteral, oral, transdermal, buccal, pulmonary, or nasal, exhibits reduced penetration across the blood-brain barrier. It is preferred that the conjugate exhibit slowed, minimal or effectively no crossing of the blood-brain barrier, while still crossing the gastro-intestinal (GI) walls and into the systemic circulation if oral delivery is intended. Moreover, the conjugates of the invention maintain a degree of bioactivity as well as bioavailability in their conjugated form in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability can be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses can be conducted, for example, by contract research organizations such as Absorption Systems, Exton, Pa.). More specifically, in the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble, non-peptidic oligomer-small molecule drug conjugate exhibits a blood-brain barrier crossing rate that is reduced as compared to the crossing rate of the small molecule drug not attached to the water-soluble, non-peptidic oligomer. Preferred exemplary reductions in blood-brain barrier crossing rates for the compounds described herein include reductions of: at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a conjugate is at least about 20%.

As indicated above, the compounds of the invention include a residue of an opioid agonist. Assays for determining whether a given compound (regardless of whether the compound is in conjugated form or not) can act as an agonist on a mu receptor or a kappa receptors are described infra.

In some instances, opioid agonists can be obtained from commercial sources. In addition, opioid agonists can be obtained through chemical synthesis. Synthetic approaches for preparing opioid agonists are described in the literature and in, for example, U.S. Pat. Nos. 2,628,962, 2,654,756, 2,649,454, and 2,806,033.

Each of these (and other) opioid agonists can be covalently attached (either directly or through one or more atoms) to a water-soluble, non-peptidic oligomer.

Small molecule drugs useful in the invention generally have a molecular weight of less than 1000 Da. Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The opioid agonist for coupling to a water-soluble, non-peptidic oligomer possesses a free hydroxyl, carboxyl, thio, amino group, or the like (i.e., "handle") suitable for covalent attachment to the oligomer. In addition, the opioid agonist can be modified by introduction of a reactive group, preferably by conversion of one of its existing functional groups to a functional group suitable for formation of a stable covalent linkage between the oligomer and the drug.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, it can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble, non-peptidic oligomer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the opioid agonist (in contrast to the step-wise addition of one or more monomers to effectively "grow" the oligomer onto the opioid agonist), it is preferred that the composition containing an activated form of the water-soluble, non-peptidic oligomer be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. Most preferably, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble, non-peptidic polymer is attached to the opioid agonist) may be a single bond, a single atom, such as an oxygen atom or a sulfur atom, two atoms, or a number of atoms. A spacer moiety is typically but is not necessarily linear in nature. The spacer moiety, "X" is preferably hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the spacer moiety linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) spacer groups, as described further below.

More specifically, in selected embodiments, a spacer moiety, X, may be any of the following: "-" (i.e., a covalent bond, that may be stable or degradable, between the residue of the small molecule opioid agonist and the water-soluble, non-peptidic oligomer), —C(O)O—, —OC(O)—, —CH$_2$—C(O)O—, —CH$_2$—OC(O)—, —C(O)O—CH$_2$—, —OC(O)—CH$_2$, —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a spacer moiety when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or one or more monomers when it is desired to "grow" the oligomer onto the opioid agonist) with a corresponding functional group within the opioid agonist. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, the terminus of the water-soluble, non-peptidic oligomer not bearing a functional group is capped to render it unreactive. When the oligomer does include a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(═O)O-Q, where Q is preferably selected from N-succinimide, N-sulfosuccinimide, N-phthalimide, N-glutarimide, N-tetrahydrophthalimide, N-norbomene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N═C═O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the opioid agonist may not have a functional group suited for conjugation. In this instance, it is possible to modify the "original" opioid agonist so that it does have the desired functional group. For example, if the opioid agonist has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule opioid agonist bearing a carboxyl group wherein the carboxyl group-bearing small molecule opioid agonist is coupled to an amino-terminated oligomeric ethylene glycol, to provide a conjugate having an amide group covalently linking the small molecule opioid agonist to the oligomer. This can be performed, for example, by combining the carboxyl group-bearing small molecule opioid agonist with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule opioid agonist bearing a hydroxyl group wherein the hydroxyl group-bearing small molecule opioid agonist is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule opioid agonist bearing a ketone group by first reducing the ketone group to form the corresponding hydroxyl group. Thereafter, the small molecule opioid agonist now bearing a hydroxyl group can be coupled as described herein.

In still another instance, it is possible to prepare a conjugate of a small molecule opioid agonist bearing an amine group. In one approach, the amine group-bearing small molecule opioid agonist and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule opioid agonist and the carbonyl carbon of the aldehyde-bearing oligomer.

In another approach for preparing a conjugate of a small molecule opioid agonist bearing an amine group, a carboxylic acid-bearing oligomer and the amine group-bearing small molecule opioid agonist are combined, typically in the presence of a coupling reagent (e.g., DCC). The result is an amide linkage formed between the amine group of the amine group-containing small molecule opioid agonist and the carbonyl of the carboxylic acid-bearing oligomer.

Exemplary conjugates of the opioid agonists of Formula I include those having the following structure:

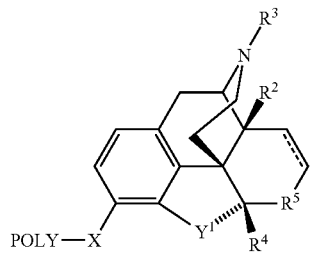

Formula I-Ca wherein each of R$^2$, R$^3$, R$^4$, the dotted line (" - - - "), Y$^1$ and R$^5$ is as previously defined with respect to Formula I, X is a spacer moiety and POLY is a water-soluble, non-peptidic oligomer.

Additional exemplary conjugates of the opioid agonists of Formula I include those having the following structure:

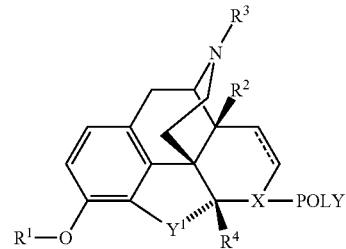

Formula I-Cd wherein each of $R^1$, $R^2$, $R^3$, $R^4$, the dotted line ("- - -"), and $Y^1$ is as previously defined with respect to Formula I, X is a spacer moiety and POLY is a water-soluble, non-peptidic oligomer.

Further additional exemplary conjugates of the opioid agonists of Formula I include those having the following structure:

Formula I-Cc

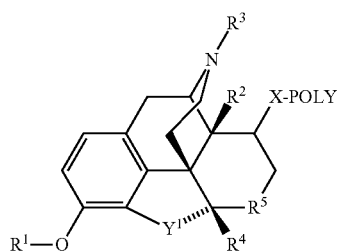

wherein each of $R^1$, $R^2$, $R^3$, $R^4$, $Y^1$ and $R^5$ is as previously defined with respect to Formula I, X is a spacer moiety and POLY is a water-soluble, non-peptidic oligomer.

Still further exemplary conjugates of the opioid agonists of Formula I include those having the following structure:

Formula I-Cd

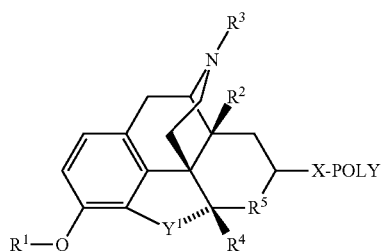

wherein each of $R^1$, $R^2$, $R^3$, $R^4$, $Y^1$ and $R^5$ is as previously defined with respect to Formula I, X is a spacer moiety and POLY is a water-soluble, non-peptidic oligomer.

Additional exemplary conjugates of the opioid agonists of Formula I include those having the following structure:

Formula I-Ce

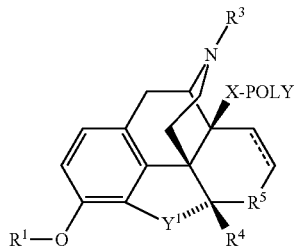

wherein each of $R^1$, $R^3$, $R^4$, the dotted line ("- - -"), $Y^1$ and $R^5$ is as previously defined with respect to Formula I, X is a spacer moiety and POLY is a water-soluble, non-peptidic oligomer.

Additional exemplary conjugates are encompassed by the following formulae:

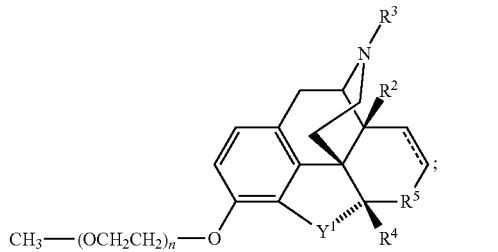

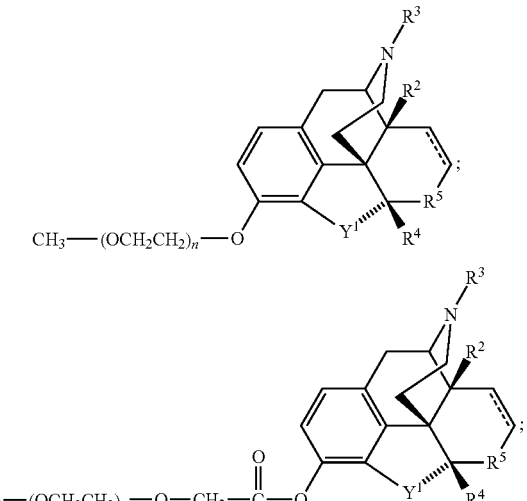

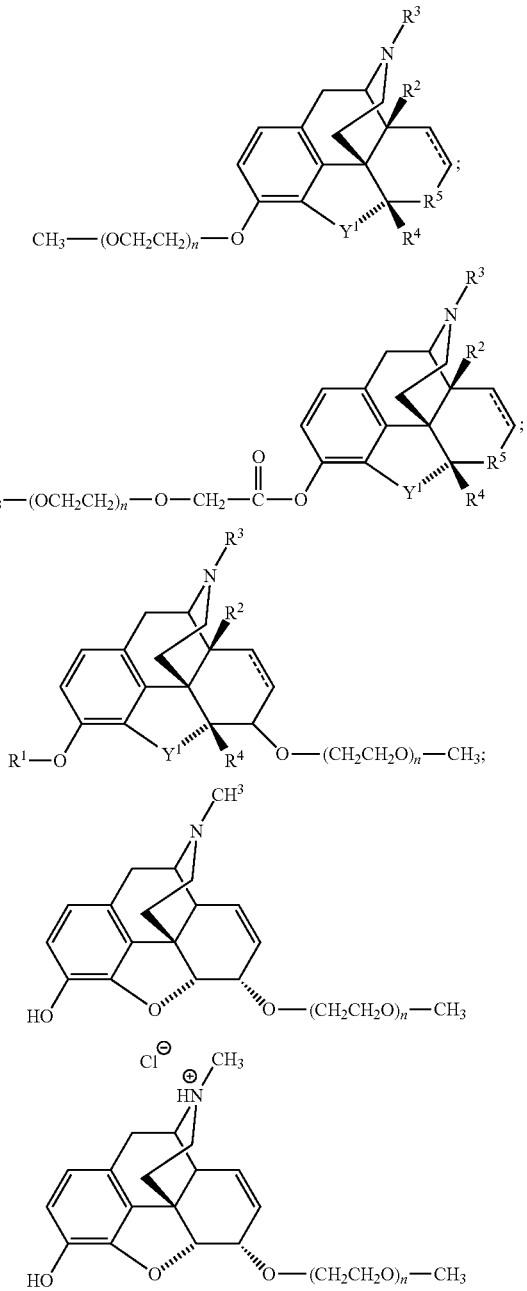

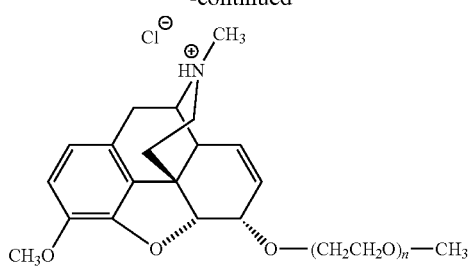
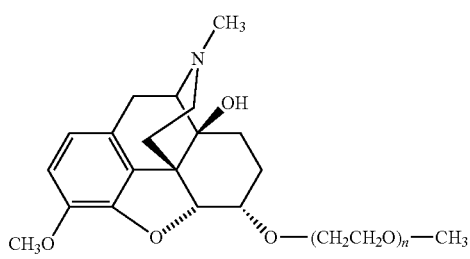
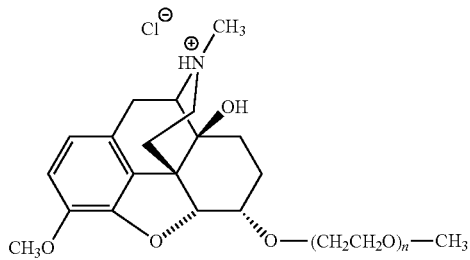
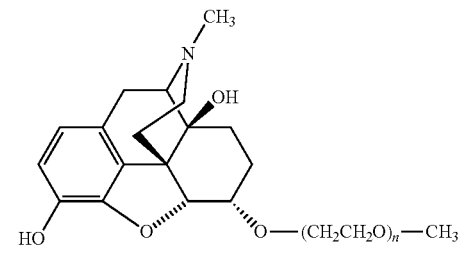
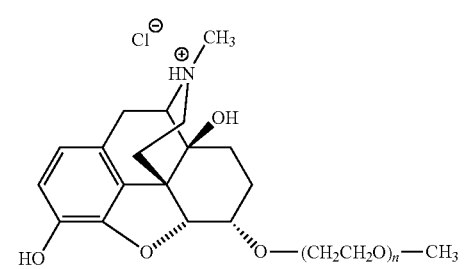
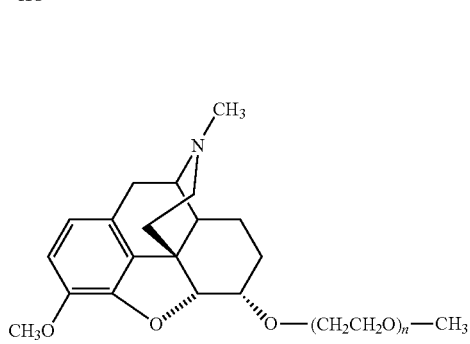
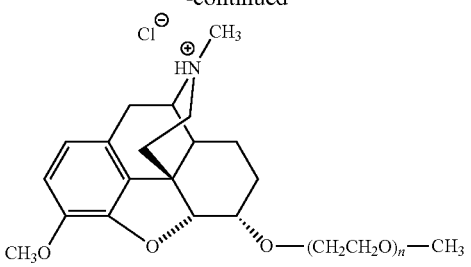
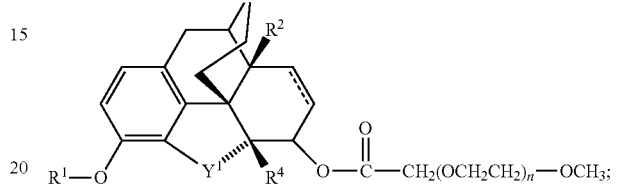
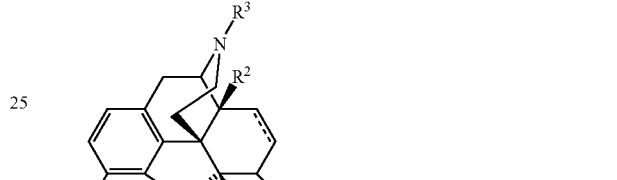
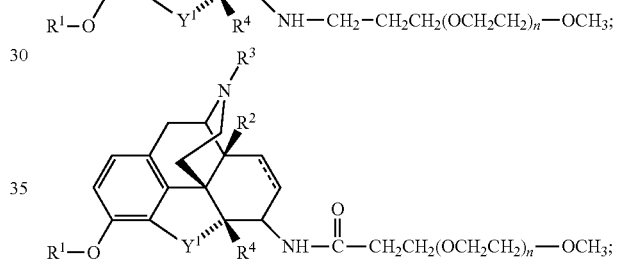
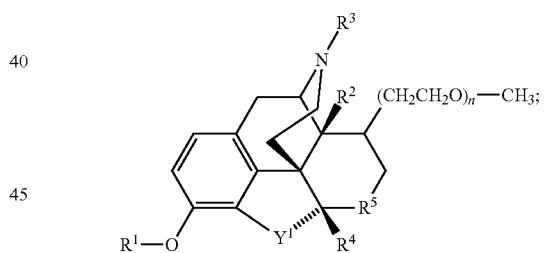
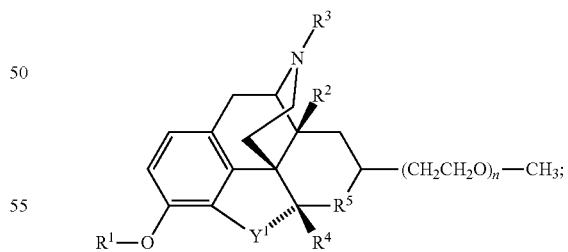
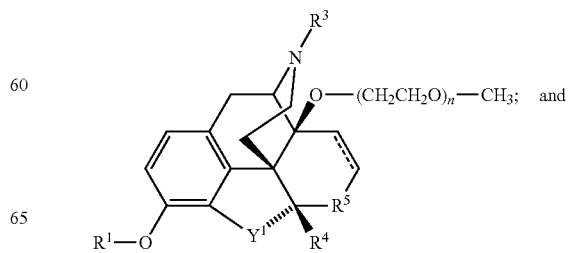

-continued

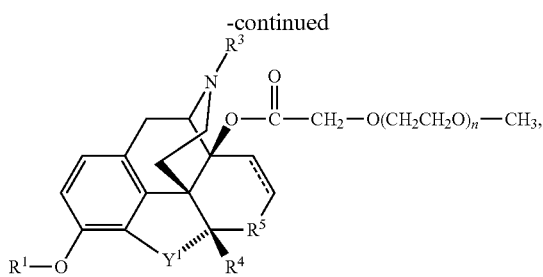

wherein, when present, each of $R^1$, $R^2$, $R^3$, $R^4$, the dotted line ("- - -"), $Y^1$ and $R^5$ is as previously defined with respect to Formula I, and the variable "n" is an integer from 1 to 30.

Exemplary conjugates of the opioid agonists of Formula II include those having the following structure:

Formula II-Ca

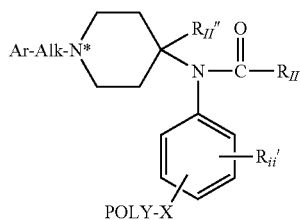

wherein:
N* is nitrogen;
Ar is selected from the group consisting of cyclohexyl, phenyl, halophenyl, methoxyphenyl, aminophenyl, pyridyl, furyl and thienyl;
Alk is selected from the group consisting of ethylene and propylene;
$R_{II}$ is selected from the group consisting of lower alkyl, lower alkoxy, dimethylamino, cyclopropyl, 1-pyrrolidyl, morpholino (preferably lower alkyl such as ethyl);
$R_{II}'$ is selected from the group consisting of hydrogen, methyl and methoxy;
$R_{II}''$ is selected from the group consisting of hydrogen and an organic radical (preferably lower alkyl);
X is a linker (e.g., a covalent bond "-" or one or more atoms); and
POLY is a water-soluble, non-peptidic oligomer.

With respect to Formula II-Ca, it will be understood that, depending on the conditions, one or both of the amines—but more typically, the amine marked with an asterisk ("N*") in Formula II-Ca—can be protonated.

Additional exemplary conjugates of the opioid agonists of Formula II include those having the following structure:

Formula II-Cb

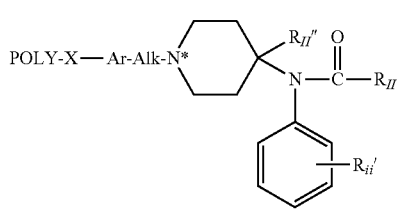

wherein:
N* is nitrogen;
Ar is selected from the group consisting of cyclohexyl, phenyl, halophenyl, methoxyphenyl, aminophenyl, pyridyl, furyl and thienyl;
Alk is selected from the group consisting of ethylene and propylene;
$R_{II}$ is selected from the group consisting of lower alkyl, lower alkoxy, dimethylamino, cyclopropyl, 1-pyrrolidyl, morpholino (preferably lower alkyl such as ethyl);
$R_{II}'$ is selected from the group consisting of hydrogen, methyl and methoxy;
$R_{II}''$ is selected from the group consisting of hydrogen and an organic radical (preferably lower alkyl);
X is a linker (e.g., a covalent bond "-" or one or more atoms); and
POLY is a water-soluble, non-peptidic oligomer.

With respect to Formula II-Cb, it will be understood that, depending on the conditions, one or both of the amines—but more typically, the amine marked with an asterisk ("N*") in Formula II-Cb—can be protonated.

Additional exemplary conjugates of the opioid agonists of Formula II include those having the following structure:

Formula II-Cc

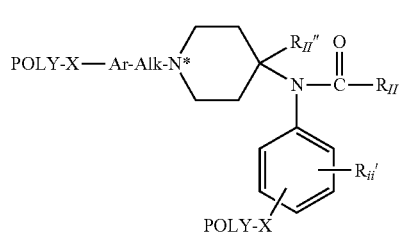

wherein:
N* is nitrogen;
Ar is selected from the group consisting of cyclohexyl, phenyl, halophenyl, methoxyphenyl, aminophenyl, pyridyl, furyl and thienyl;
Alk is selected from the group consisting of ethylene and propylene;
$R_I$ is selected from the group consisting of lower alkyl, lower alkoxy, dimethylamino, cyclopropyl, 1-pyrrolidyl, morpholino (preferably lower alkyl such as ethyl);
$R_{II}'$ is selected from the group consisting of hydrogen, methyl and methoxy;
$R_{II}''$ is selected from the group consisting of hydrogen and an organic radical (preferably lower alkyl);
each X is independently a linker (e.g., a covalent bond "-" or one or more atoms); and
each POLY is independently a water-soluble, non-peptidic oligomer.

With respect to Formula II-Cc, it will be understood that, depending on the conditions, one or both of the amines—but more typically, the amine marked with an asterisk ("N*") in Formula II-Cc—can be protonated.

Additional exemplary conjugates are encompassed by the following formulae:

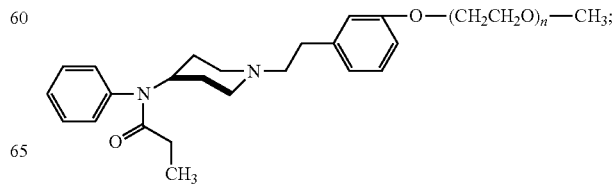

-continued

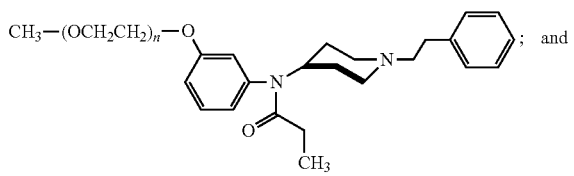

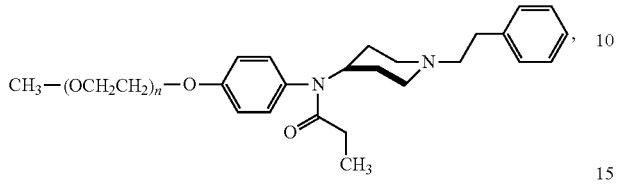

wherein the variable "n" is an integer from 1 to 30.

Additional conjugates include those provided below:

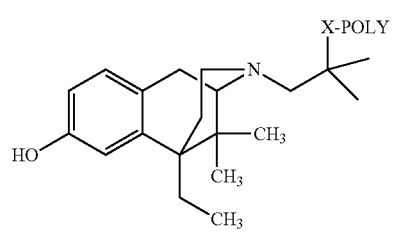

(exemplary bremazocine conjugate)

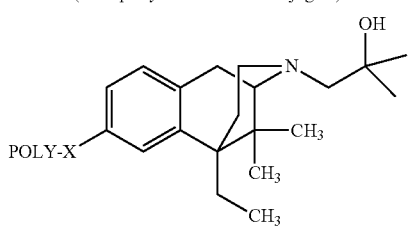

(exemplary bremazocine conjugate)

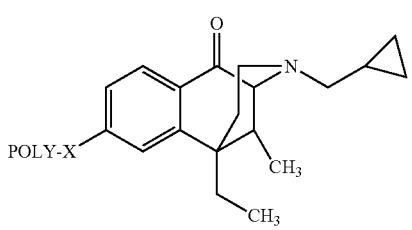

(exemplary ethylketocyclazocine conjugate)

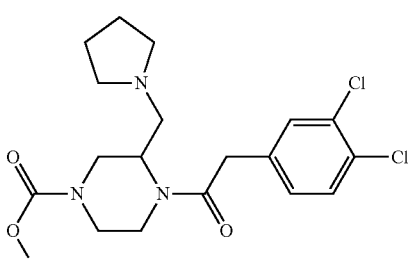

(exemplary GR89,696 conjugate)

-continued

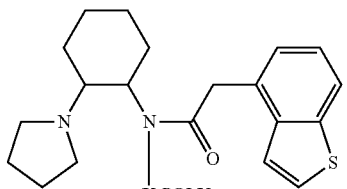

(exemplary PD117,302 conjugate)

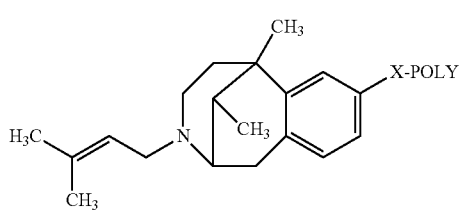

(exemplary pentazocine conjugate)

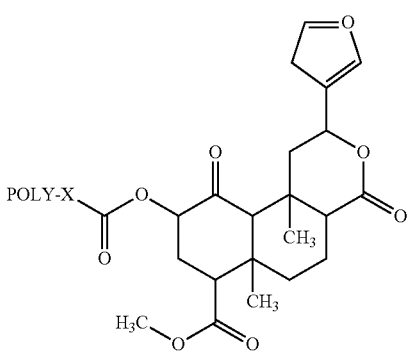

(exemplary salvinorin A conjugate)

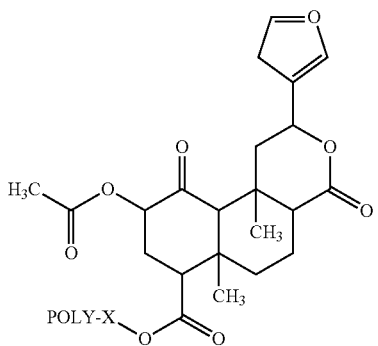

(exemplary salvinorin A conjugate)

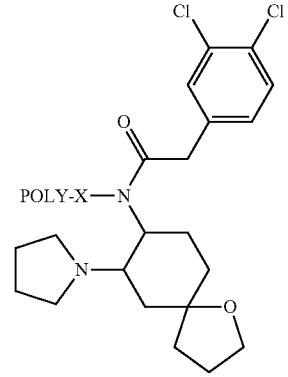

(exemplary spiradoline conjugate)

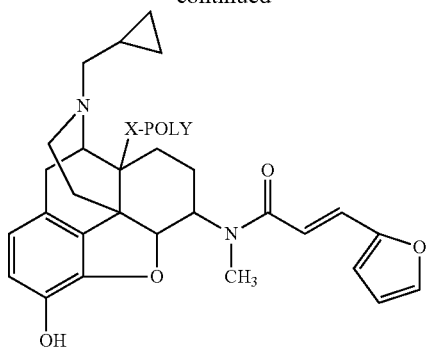

(exemplary TRK-820 conjugate)

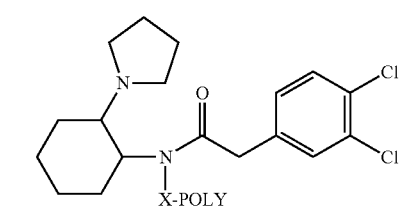

(exemplary U50488 conjugate)

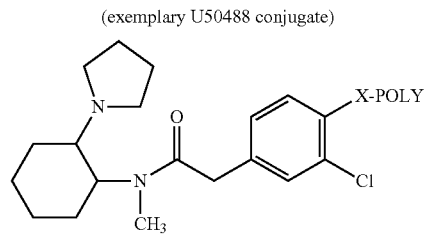

(exemplary U50488 conjugate)

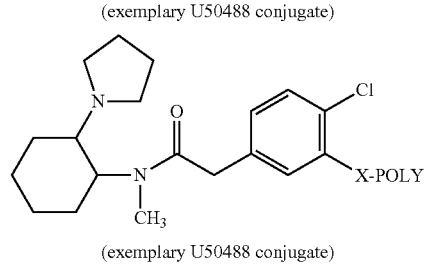

(exemplary U50488 conjugate)

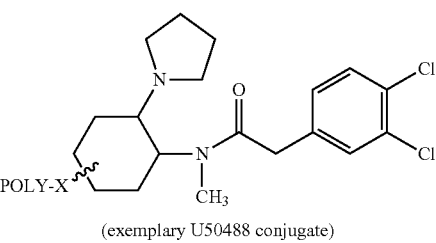

(exemplary U50488 conjugate)

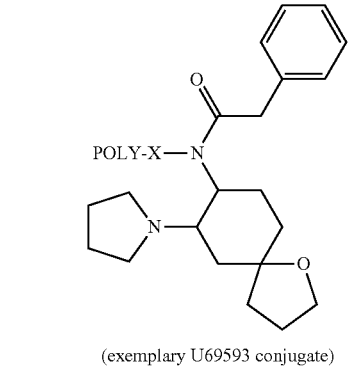

(exemplary U69593 conjugate)

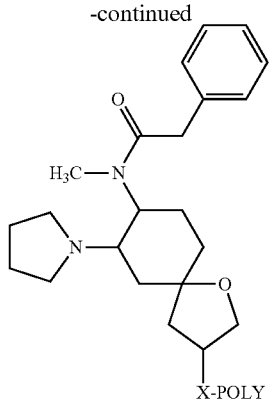

(exemplary U69593 conjugate)

wherein, for each of the above conjugates, X is a linker (e.g., a covalent bond "-" or one or more atoms) and POLY is a water-soluble, non-peptidic oligomer.

An additional conjugate is provided below:

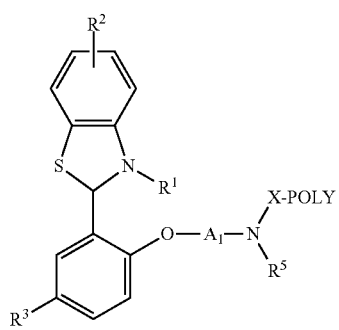

wherein:

$R^1$ is acyl $R^2$ is selected from the group consisting of hydrogen, halogen, unsubstituted alkyl and alkyl substituted by halogen;

$R^3$ is selected from the group consisting of halogen and alkoxy;

$R^5$ is selected from the group consisting of hydroxyl, ester, alkoxy, and alkoxyalkyl;

$A_1$ is alkylene;

X is a linker; and

POLY is a water-soluble, non-peptidic oligomer.

The conjugates of the invention can exhibit a reduced blood-brain barrier crossing rate. Moreover, the conjugates maintain at least about 5%, 10%, 20%, 30%, 40%, 50%, 60%, 70%, or more of the bioactivity of the unmodified parent small molecule drug.

While it is believed that the full scope of the conjugates disclosed herein has been described, an optimally sized oligomer can be determined as follows.

First, an oligomer obtained from a monodisperse or bimodal water soluble oligomer is conjugated to the small molecule drug. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results are compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible, and allows one to effectively tailor the properties of the resulting conjugate. By making small, incremental changes in oligomer size, and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the opioid agonist or the conjugate of an opioid agonist and a water-soluble non-peptidic oligomer has activity as mu opioid receptor agonist, it is possible to test such a compound. For example, $K_D$ (binding affinity) and $B_{max}$ (receptor number) can be determined using an approach modified from that described in Malatynska et al. (1995) NeuroReport 6:613-616. Briefly, human mu receptors can be recombinantly expressed in Chinese hamster ovary cells. The radioligand [$^3$H]-diprenorphine (30-50 Ci/mmol) with a final ligand concentration of [0.3 nM] can be used. Naloxone is used as a non-specific determinate [3.0 nM], a reference compound and positive control. Reactions are carried out in 50 mM TRIS-HCl (pH 7.4) containing 5 mM MgCl$_2$, at 25° C. for 150 minutes. The reaction is terminated by rapid vacuum filtration onto glass fiber filters. Radioactivity trapped onto filters is determined and compared to control values in order to ascertain any interactions of test compound with the cloned mu binding site.

Similar testing can be performed for kappa opioid receptor agonist. See, for example, Lahti et al. (1985) Eur. Jml. Pharmac. 109:281-284; Rothman et al. (1992) Peptides 13:977-987; Kinouchi et al. (1991) Eur. Jml. Pharmac. 207:135-141. Briefly, human kappa receptors can be obtained from guinea pig cerebellar membranes. The radioligand [$^3$H]-U-69593 (40-60 Ci/mmol) with a final ligand concentration of [0.75 nM] can be used. U-69593 is used as a non-specific determinate [1.0 µM], a reference compound and positive control. Reactions are carried out in 50 mM HEPES (pH 7.4) at 30° C. for 120 minutes. The reaction is terminated by rapid vacuum filtration onto glass fiber filters. Radioactivity trapped onto filters is determined and compared to control values in order to ascertain any interactions of test compound with the cloned kappa binding site.

The conjugates described herein include not only the conjugates themselves, but the conjugates in the form of a pharmaceutically acceptable salt as well. A conjugate as described herein can possess a sufficiently acidic group, a sufficiently basic group, or both functional groups, and, accordingly, react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (*theobroma* oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

Although useful in reducing many types of metabolism (including both Phase I and Phase II metabolism) can be reduced, the conjugates are particularly useful when the small molecule drug is metabolized by a hepatic enzyme (e.g., one or more of the cytochrome P450 isoforms) and/or by one or more intestinal enzymes.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by a NMR spectrometer manufactured by Bruker (MHz≥200). A list of certain compounds as well as the source of the compounds is provided below.

Example 1

Preparation of an Oligomer-Nalbuphine Conjugates—"Approach A"

PEG-Nalbuphine was prepared using a first approach. Schematically, the approach followed for this example is shown below.

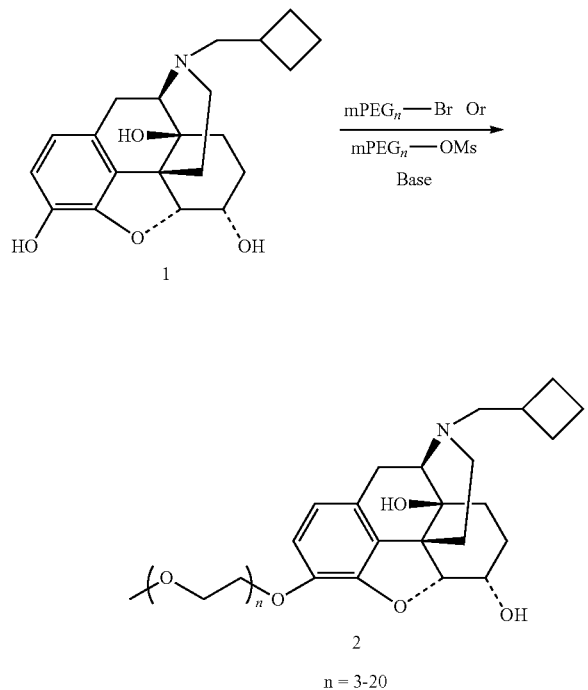

Desalting of Nalbuphine Hydrochloride Dihydrate

Nalbuphine hydrochloride dihydrate (600 mg, from Sigma) was dissolved in water (100 mL). Saturated aqueous $K_2CO_3$ was added and then adjusted the pH to 9.3 with 1 N HCl solution, saturated with sodium chloride. The solution was extracted with dichloromethane (5×25 mL). The combined organic solution was washed with brine (100 mL), dried over $Na_2SO_4$, concentrated to dryness and dried under high vacuum to yield nalbuphine (483.4 mg, 97% recovery). The product was confirmed by $^1$H-NMR in $CDCl_3$.

Synthesis of 3-O-mPEG$_3$-Nalbuphine (2) (n=3)

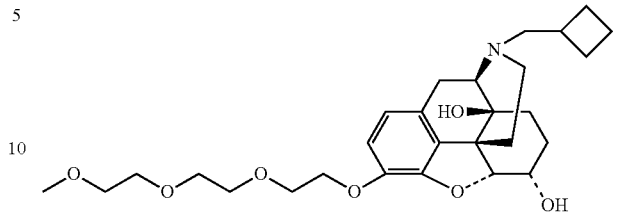

Nalbuphine (28.5 mg, 0.08 mmol) was dissolved in a mixture of acetone (2 mL) and toluene (1.5 mL). Potassium carbonate (21 mg, 0.15 mmol) was added, followed by an addition of mPEG$_3$-Br (44.5 mg, 0.20 mmol) at room temperature. The resulting mixture was stirred at room temperature for 27.5 hours. More potassium carbonate (24 mg, 0.17 mmol) was added. The mixture was heated with CEM microwave such that 60° C. for 20 minutes was achieved, and then such that 100° C. for 30 minutes was achieved. DMF (0.2 mL) was added. The mixture was heated with microwave at 60° C. for 20 minutes, at 100° C. for 30 minutes. The reaction was concentrated to remove the organic solvents, the residue was mixed with water (10 mL), extracted with dichloromethane (4×15 mL). The combined organic solution was washed with brine, dried over $Na_2SO_4$, concentrated. The crude product was checked with HPLC and LC-MS. The residue was mixed again with water (10 mL), adjusted the pH to 2.3 with 1N HCl, washed with dichloromethane (2×15 mL). The aqueous solution was adjusted to pH 10.4 with 0.2 N NaOH, extracted with dichloromethane (4×15 mL). The combined organic solution was washed with brine, dried over $Na_2SO_4$, concentrated. The residue was purified by Biotage flash column chromatography with 0-10% MeOH in dichloromethane resulting in the desired product 3-O-mPEG$_3$-nalbuphine (2) (n=3) (32.7 mg) in 81% yield. The product was confirmed by $^1$H-NMR, LC-MS.

Synthesis of 3-O-mPEG$_4$-Nalbuphine (2) (n=4)

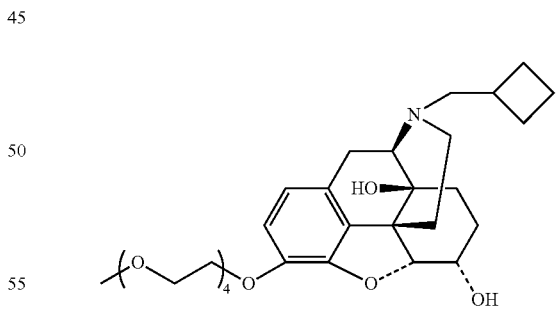

A mixture of nalbuphine (96 mg, 0.27 mmol) and mPEG$_4$-OMs (131 mg, 0.46 mmol) in acetone (8 mL) in the presence of potassium carbonate (113 mg, 0.82 mmol) was heated to reflux for 16 hours, cooled to room temperature, filtered and the solid was washed with acetone and DCM. The solution was collected and concentrated to dryness. The residue was purified by Biotage automatic flash column chromatography with 0-10% MeOH in dichloromethane to result in the product 3-O-mPEG$_4$-nalbuphine 2 (n=4) (109 mg) in 74% yield. The product was confirmed by $^1$H-NMR, LC-MS.

Synthesis of 3-O-mPEG$_5$-Nalbuphine (2) (n=5)

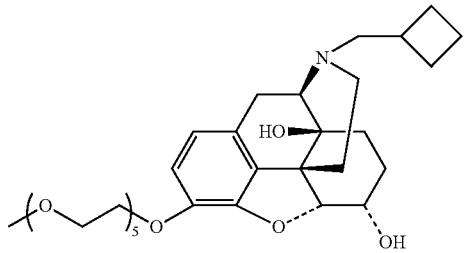

A mixture of nalbuphine (78.3 mg, 0.22 mmol) and mPEG$_5$-OMs (118 mg, 0.36 mmol) in acetone (8 mL) in the presence of potassium carbonate (93 mg, 0.67 mmol) was heated to reflux for 16 hours, cooled to room temperature, filtered and the solid was washed with acetone and DCM. The solution was collected and concentrated to dryness. The residue was purified by Biotage automatic flash column chromatography with 0-10% MeOH in dichloromethane to result in the product 3-O-mPEG$_5$-nalbuphine (2) (n=5) (101 mg) in 76% yield. The product was confirmed by $^1$H-NMR, LC-MS.

Synthesis of 3-O-mPEG$_6$-Nalbuphine (2) (n=6)

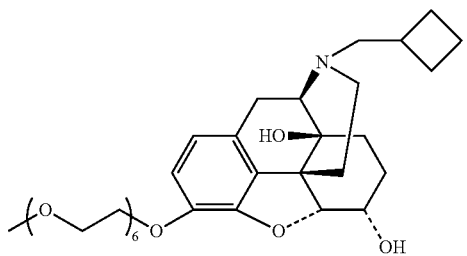

A mixture of nalbuphine (89.6 mg, 0.25 mmol) and mPEG$_6$-OMs (164 mg, 0.44 mmol) in acetone (8 mL) in the presence of potassium carbonate (98 mg, 0.71 mmol) was heated to reflux for 18 hours, cooled to room temperature, filtered and the solid washed with acetone and DCM. The solution was collected and concentrated to dryness. The residue was purified by Biotage automatic flash column chromatography with 0-10% MeOH in dichloromethane to result in the product 3-O-mPEG$_6$-nalbuphine (2) (n=6) (144 mg) in 91% yield. The product was confirmed by $^1$H-NMR, LC-MS.

Synthesis of 3-O-mPEG$_7$-Nalbuphine (2) (n=7)

A mixture of nalbuphine (67 mg, 0.19 mmol) and mPEG$_7$-Br (131 mg, 0.33 mmol) in acetone (10 mL) in presence of potassium carbonate (67 mg, 0.49 mmol) was heated to reflux for 6 hours, cooled to room temperature, filtered and the solid washed and dichloromethane. The solution was concentrated to dryness. The residue was purified by Biotage automatic flash column chromatography with 2-10% MeOH in dichloromethane to result in the product 3-O-mPEG$_7$-nalbuphine (2) (n=7) (40.6 mg). The product was confirmed by $^1$H-NMR, LC-MS.

Synthesis of 3-O-mPEG$_8$-Nalbuphine (2) (n=8)

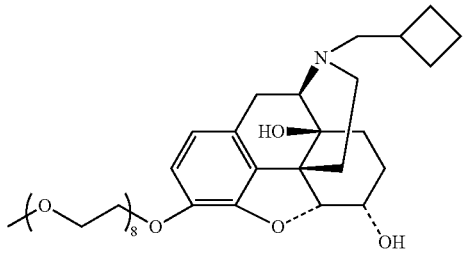

A mixture of nalbuphine (60 mg, 0.17 mmol) and mPEG$_8$-Br (105.7 mg, 0.24 mmol) in the presence of potassium carbonate (40.8 mg, 0.30 mmol) in toluene/DMF (3 mL/0.3 mL) was heated with CEM microwave such that 100° C. for 30 minutes was achieved. Then acetone (1 mL) was added. After the mixture was heated with CEM microwave such that 100° C. for 90 minutes was achieved, more of K$_2$CO$_3$ (31 mg, 0.22 mmol) and mPEG$_8$-Br (100 mg, 0.22 mmol) were added. The mixture was heated with CEM microwave such that 100° C. for 60 minutes was achieved. mPEG$_8$-Br (95 mg, 0.21 mmol) was added again. The mixture was heated again with CEM microwave such that 100° C. for 30 minutes was achieved. The reaction mixture was concentrated under reduce pressure. The residue was mixed with water (2 mL) and brine (10 mL). The pH of the solution was adjusted to 1.56 with 1 N HCl, extracted with dichloromethane (3×20 mL). The combined organic solution was dried with Na$_2$SO$_4$, concentrated to yield residue I (a mixture of the desired product and precursor material). The aqueous solution was changed to pH 10.13 with 0.2 N NaOH, extracted with dichloromethane (4×15 mL). The organic solution was washed with brine, dried over Na$_2$SO$_4$, concentrated to result in residue II (19.4 mg), which contained the product and the starting material nalbuphine. The residue I was purified by Biotage automatic flash column chromatography with 2-10% MeOH in dichloromethane to result in the product 3-O-mPEG$_8$-nalbuphine (2) (n=8) (44.6 mg). The product was confirmed by 1H-NMR, LC-MS.

Example 2

Preparation of an Oligomer-Nalbuphine Conjugates—"Approach B"

PEG-Nalbuphine was prepared using a second approach. Schematically, the approach followed for this example is shown below.

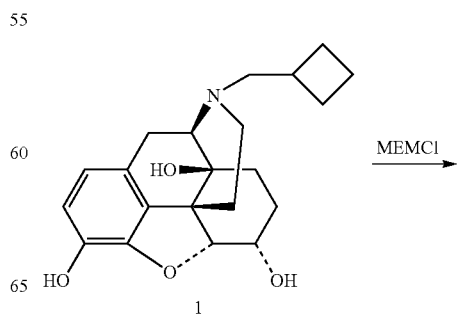

Synthesis of 3-O-MEM-Nalbuphine (3)

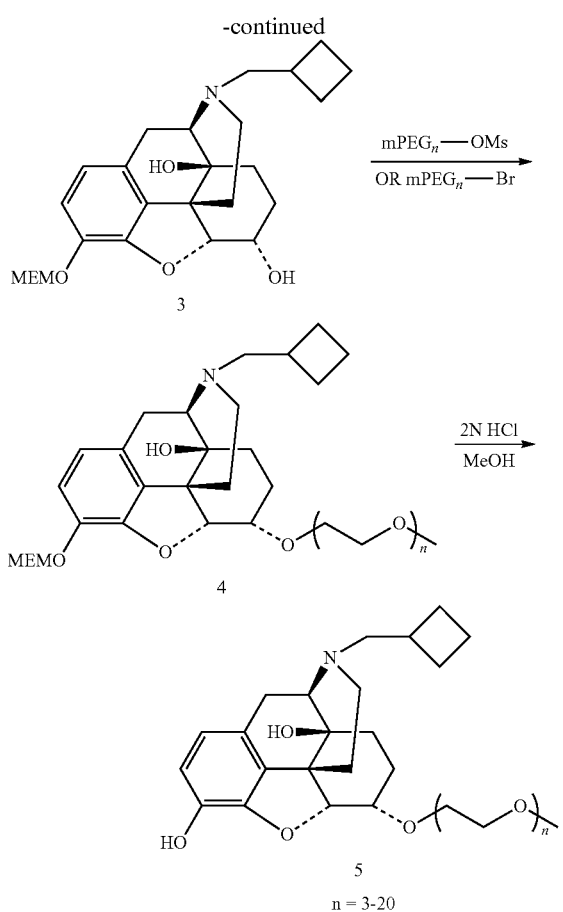

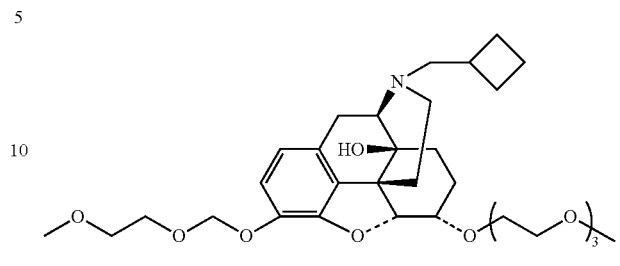

Nalbuphine (321.9 mg, 0.9 mmol) was dissolved in acetone/toluene (19 mL/8 mL). Then potassium carbonate (338 mg, 2.45 mmol) was added, followed by an addition of MEMCl (160 μL, 1.41 mmol). The resulting mixture was stirred at room temperature for 21 hours MeOH (0.3 mL) was added to quench the reaction. The reaction mixture was concentrated under reduced pressure to dryness. The residue was mixed with water (5 mL) and brine (15 mL), extracted with dichloromethane (3×15 mL). The combined organic solution was washed with brine, dried over Na$_2$SO$_4$, concentrated. The residue was separated by Biotage automatic flash column chromatography with 2-10% MeOH in dichloromethane to result in the product 3-O-MEM-nalbuphine (3) (341 mg) and the starting material nalbuphine (19.3 mg). The product was confirmed by $^1$H-NMR, LC-MS.

Synthesis of 6-O-mPEG$_3$-3-O-MEM-Nalbuphine (4) (n=3)

A 20-mL vial was placed with 3-O-MEM-nalbuphine (3) (85 mg, 0.19 mmol) and toluene (15 mL). The mixture was concentrated to remove 7 mL of toluene. Anhydrous DMF (0.2 mL) was added. The vial was flashed with nitrogen. NaH (60% dispersion in mineral oil, 21 mg, 0.53 mmol) was added, followed by an addition of mPEG$_3$-OMs (94 mg, 0.39 mmol). After the resulting mixture was heated at 45° C. for 22.5 hours, more of NaH (22 mg, 0.55 mmol) was added. The mixture was heated at 45° C. for another six hours, NaH (24 mg) was added and the mixture was heated at 45° C. for another 19 hours. When the mixture was cooled to room temperature, saturated NaCl aqueous solution (1 mL) was added to quench the reaction. The mixture was diluted with water (10 mL), extracted with EtOAc (4×15 mL). The combined organic solution was washed with brine, dried over Na$_2$SO$_4$, concentrated. The residue was separated by Biotage automatic flash column chromatography with 0-10% MeOH in dichloromethane to result in the product 6-O-mPEG$_3$-3-O-MEM-nalbuphine (4) (n=3) (79.4 mg) in 71% yield. The product was confirmed by $^1$H-NMR, LC-MS.

Synthesis of 6-O-mPEG$_3$-Nalbuphine (5) (n=3)

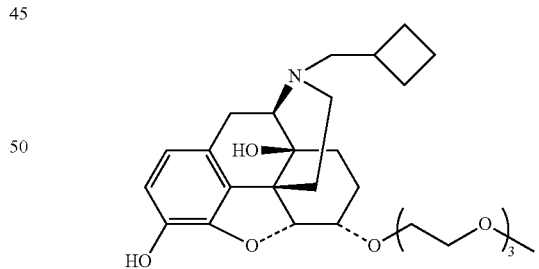

6-O-mPEG$_3$-3-O-MEM-nalbuphine (4) (79.4 mg) was stirred in 2 M HCl in methanol at room temperature for six hours. The mixture was diluted with water (5 mL), and concentrated to removed the methanol. The aqueous solution was washed with dichloromethane (5 mL), and the pH of the solution was adjusted to 9.35 with 0.2 N NaOH and solid NaHCO$_3$, extracted with dichloromethane (4×30 mL). The combined organic solution was washed with brine, dried over Na$_2$SO$_4$, concentrated to result in the product 6-O-mPEG$_3$-nalbuphine (5) (n=3) (62.5 mg) in 93% yield. The product was confirmed by $^1$H-NMR, LC-MS.

Synthesis of 6-O-mPEG$_4$-3-O-MEM-Nalbuphine (4) (n=4)

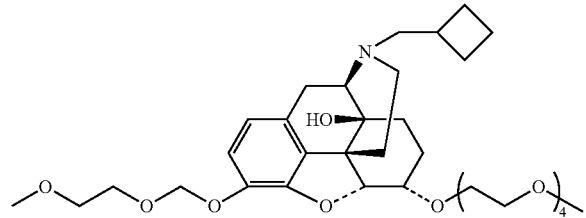

A 50-mL round-flask was placed with 3-O-MEM-nalbuphine (3) (133.8 mg, 0.3 mmol) and mPEG$_4$-OMs (145 mg, 0.51 mmol) and toluene (20 mL). The mixture was concentrated to remove about 12 mL of toluene. Anhydrous DMF (0.2 mL) was added. NaH (60% dispersion in mineral oil, 61 mg, 1.52 mmol) was added. After the resulting mixture was heated at 45° C. for 21.5 hours, more of NaH (30 mg, 0.75 mmol) was added. The mixture was heated at 45° C. for another five hours. When the mixture was cooled to room temperature, saturated NaCl aqueous solution (1 mL) was added to quench the reaction. The mixture was diluted with water (15 mL), and extracted with EtOAc (4×15 mL). The combined organic solution was washed with brine, dried over Na$_2$SO$_4$, concentrated. The residue was separated by Biotage automatic flash column chromatography on silica gel with 0-10% MeOH in dichloromethane to result in the product 6-O-mPEG$_4$-3-O-MEM-nalbuphine (4) (n=4) (214.4 mg). The $^1$H-NMR showed some mPEG$_4$-OMs in the product. No attempt was made for further purification. The product was confirmed by $^1$H-NMR, LC-MS.

Synthesis of 6-O-mPEG$_4$-Nalbuphine (5) (n=4)

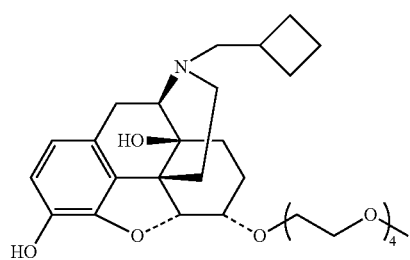

6-O-mPEG$_4$-3-O-MEM-nalbuphine (4) (214.4 mg) was stirred in 2 M HCl in methanol (30 mL) at room temperature for 6 hours. The mixture was diluted with water (5 mL), and concentrated to removed the methanol. The aqueous solution was adjusted to 9.17 with 1 N NaOH, extracted with dichloromethane (4×25 mL). The combined organic solution was washed with brine, dried over Na$_2$SO$_4$, and concentrated. The residue was purified by flash column chromatography on silica gel using 3-8% MeOH/DCM (Biotage) to result in the pure product 6-O-mPEG$_4$-nalbuphine (5) (n=4) (90.7 mg), along with some impure product. The product was confirmed by $^1$H-NMR, LC-MS. The impure part was dissolved in DCM (~1.5 mL). 1 N HCl in ether (20 mL) was added, centrifuged. The residue was collected and redissolved in DCM (25 mL). The DCM solution was washed with aq. 5% NaHCO$_3$ (20 mL), brine (2×30 mL), dried over Na$_2$SO$_4$, concentrated to afford another part pure product (24.8 mg).

Synthesis of 6-O-mPEG$_5$-3-O-MEM-Nalbuphine (4) (n=5)

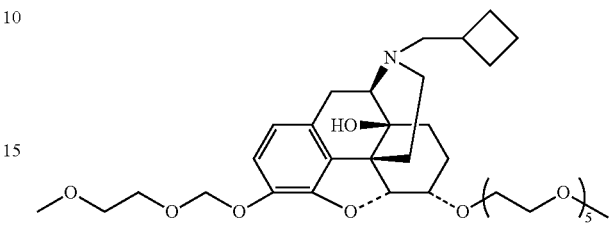

A 50-mL round-flask was placed with 3-O-MEM-nalbuphine (3) (103.9 mg, 0.23 mmol), mPEG$_5$-OMs (151 mg, 0.46 mmol) and toluene (38 mL). The mixture was concentrated to remove about 20 mL of toluene. Anhydrous DMF (0.5 mL) was added. NaH (60% dispersion in mineral oil, 102 mg, 2.55 mmol) was added. After the resulting mixture was heated at 45° C. for 18 hours, more of NaH (105 mg) was added. The mixture was heated at 45° C. for another 5.5 hours. NaH (87 mg) was added and the mixture was heated at 45° C. for another 17.5 hours. When the mixture was cooled to room temperature, saturated NaCl aqueous solution (3 mL) was added to quench the reaction. The mixture was diluted with water (10 mL), extracted with EtOAc (4×20 mL). The combined organic solution was washed with brine, dried over Na$_2$SO$_4$, concentrated. The residue was separated by Biotage automatic flash column chromatography on silica gel with 3-8% MeOH in dichloromethane to result in the product 6-O-mPEG$_5$-3-O-MEM-nalbuphine (4) (n=5).

Synthesis of 6-O-mPEG$_5$-Nalbuphine (5) (n=5)

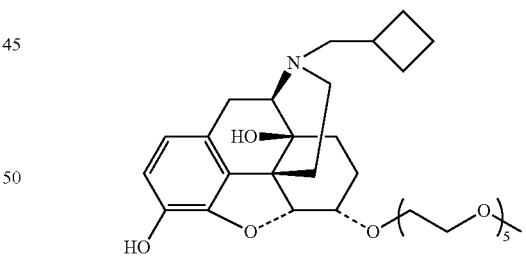

The above 6-O-mPEG$_5$-3-O-MEM-nalbuphine (4) was stirred in 2 M HCl in methanol (30 mL) at room temperature for 2.5 hour. The mixture was diluted with water (5 mL), concentrated to removed the methanol. The aqueous solution was adjusted to 9.19 with 1 N NaOH, extracted with dichloromethane (4×15 mL). The combined organic solution was washed with brine, dried over Na$_2$SO$_4$, concentrated. After purification with flash column chromatography on silica, mPEG$_5$-OMs was observed in $^1$H-NMR. The residue was dissolved in DCM (~1 mL). 1 N HCl in ether (18 mL) was added, centrifuged. The residue was collected and redissolved in DCM (25 mL). The DCM solution was washed with aq. 5% NaHCO$_3$ (2×20 mL), brine (2×30 mL), dried over Na$_2$SO$_4$, concentrated. The residue was separated by Biotage automatically flash column chromatography on silica gel with 4-8% MeOH in dichloromethane to result in the product 6-O-mPEG$_5$-nalbuphine (5) (n=5) (55 mg).

Synthesis of 6-O-mPEG$_6$-3-O-MEM-Nalbuphine (4) (n=6)

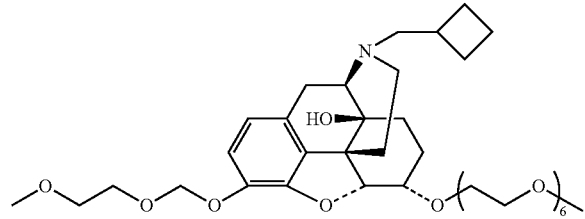

3-O-MEM-nalbuphine (3) (77.6 mg, 0.17 mmol) and mPEG$_6$-OMs (199 mg, 0.53 mmol) was dissolved in toluene (20 mL). The mixture was concentrated to remove about 12 mL of toluene. Anhydrous DMF (0.2 mL) was added, followed by an addition of NaH (60% dispersion in mineral oil, 41 mg, 1.03 mmol). After the resulting mixture was heated at 45° C. for 23 hours, more of NaH (46 mg) was added. The mixture was heated at 45° C. for another 24 hours. When the mixture was cooled to room temperature, saturated NaCl aqueous solution (5 mL) was added to quench the reaction. The mixture was diluted with water (10 mL), extracted with EtOAc (4×15 mL). The combined organic solution was washed with brine, dried over Na$_2$SO$_4$, concentrated. The residue was directly used for the next step.

Synthesis of 6-O-mPEG$_6$-Nalbuphine (5) (n=6)

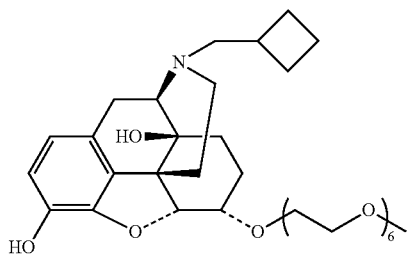

The above 6-O-mPEG$_6$-3-O-MEM-nalbuphine (4) was stirred in 2 M HCl in methanol (30 mL) at room temperature for 20 hours. The mixture was diluted with water (5 mL), concentrated to removed the methanol. The aqueous solution was adjusted to 9.30 with 1 N NaOH, extracted with dichloromethane (5×20 mL). The combined organic solution was washed with brine, dried over Na$_2$SO$_4$, concentrated. The residue was dissolved in DCM (~1 mL). 1 N HCl in ether (20 mL) was added, centrifuged. The residue was collected and redissolved in DCM (40 mL). The DCM solution was washed with aq. 5% NaHCO$_3$ (2×20 mL), water (30 mL), brine (2×30 mL), dried over Na$_2$SO$_4$, concentrated to result in the product 6-O-mPEG$_6$-nalbuphine (5) (n=6) (68 mg).

Synthesis of 6-O-mPEG$_7$-3-O-MEM-Nalbuphine (4, n=7)

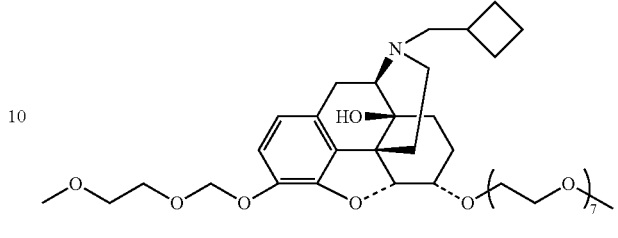

A 50-mL round-flask was placed with 3-O-MEM-nalbuphine (3) (82.8 mg, 0.186 mmol), mPEG$_7$-Br (151 mg, 0.46 mmol) and toluene (15 mL). The mixture was concentrated to remove about 9 mL of toluene. Anhydrous DMF (0.2 mL) was added. NaH (60% dispersion in mineral oil, 50 mg, 1.25 mmol) was added. After the resulting mixture was heated at 45° C. for 22.5 hours, more of NaH (38 mg, 0.94 mmol) was added. The mixture was heated at 45° C. for another 5 hours. When the mixture was cooled to room temperature, saturated NaCl aqueous solution (5 mL) was added to quench the reaction. The mixture was diluted with water (10 mL), and extracted with EtOAc (4×10 mL). The combined organic solution was washed with brine, dried over Na$_2$SO$_4$, concentrated. The residue was directly used for the next step.

Synthesis of 6-O-mPEG$_7$-Nalbuphine (5) (n=7)

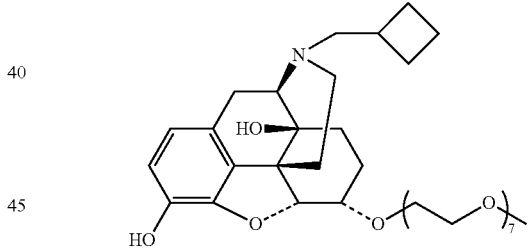

The above 6-O-mPEG$_7$-3-O-MEM-nalbuphine (4) was stirred in 2 M HCl in methanol (20 mL) at room temperature for 20 hours. The mixture was diluted with water, and concentrated to remove the methanol. The aqueous solution was adjusted to 9.30 with NaHCO$_3$ and 0.2 N NaOH, extracted with dichloromethane (4×20 mL). The combined organic solution was washed with brine, dried over Na$_2$SO$_4$, concentrated. The residue was purified with flash column chromatography on silica gel and washed with DCM at acidic condition, adjusted the pH to 9.35, extracted with DCM. The product was still contaminated with small PEG. The residue was dissolved in DCM (~2 mL). 1 N HCl in ether (10 mL) was added, centrifuged. The residue was collected and redissolved in DCM (10 mL). The DCM solution was washed with aq. 5% NaHCO$_3$, brine, dried over Na$_2$SO$_4$, concentrated to result in the product 6-O-mPEG$_7$-nalbuphine (5) (n=7) (49 mg).

Synthesis of 6-O-mPEG$_8$-3-O-MEM-Nalbuphine (4) (n=8)

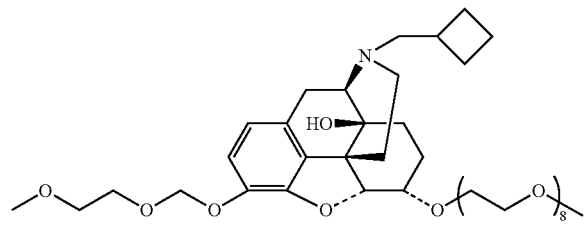

A 50-mL round-flask was placed with 3-O-MEM-nalbuphine (3) (80.5 mg, 0.181 mmol), mPEG$_8$-Br (250 mg, 0.56 mmol) and toluene (15 mL). The mixture was concentrated to remove about 6 mL of toluene. Anhydrous DMF (0.2 mL) was added. NaH (60% dispersion in mineral oil, 49 mg, 1.23 mmol) was added. The resulting mixture was heated at 45° C. for 23 hours, the mixture was cooled to room temperature, saturated NaCl aqueous solution (5 mL) and water (10 mL) was added to quench the reaction. The mixture was extracted with EtOAc (4×20 mL). The combined organic solution was washed with brine, dried over Na$_2$SO$_4$, concentrated. The residue was directly used for the next step.

Synthesis of 6-O-mPEG$_8$-Nalbuphine (5) (n=8)

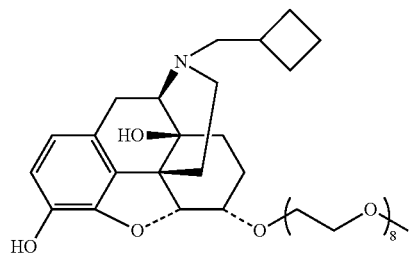

The above 6-O-mPEG$_8$-3-O-MEM-nalbuphine (4) was stirred in 2 M HCl in methanol (20 mL) at room temperature for 17 hours. The mixture was diluted with water, concentrated to remove the methanol. The aqueous solution was adjusted to 9.32 with NaHCO$_3$ and 0.2 N NaOH, extracted with dichloromethane (4×20 mL). The combined organic solution was washed with brine, dried over Na$_2$SO$_4$, concentrated. The residue was dissolved in DCM (~1 mL). 1 N HCl in ether (20 mL) was added, centrifuged. The residue was collected and redissolved in DCM (30 mL). The DCM solution was washed with aq. 5% NaHCO$_3$ (60 mL), water (30 mL), brine (30 mL), dried over Na$_2$SO$_4$, concentrated. The residue was purified with flash column chromatography on silica gel using 0-10% methanol in dichloromethane to result in the product 6-O-mPEG$_8$-nalbuphine (5) (n=8) (78.4 mg).

Synthesis of 6-O-mPEG$_9$-3-O-MEM-Nalbuphine (4) (n=9)

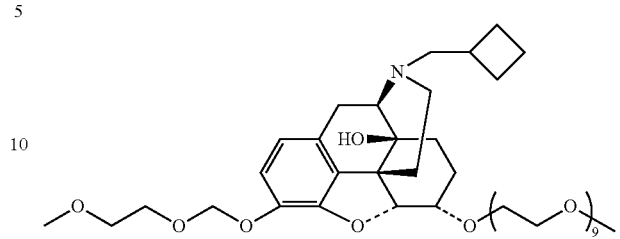

A 50-mL round-flask was placed with 3-O-MEM-nalbuphine (3) (120 mg, 0.27 mmol), mPEG$_9$-OMs (245 mg, 0.48 mmol) and toluene (20 mL). The mixture was concentrated to remove about 10 mL of toluene. NaH (60% dispersion in mineral oil, 63 mg, 1.57 mmol) was added, followed by an addition of anhydrous DMF (0.5 mL). The resulting mixture was heated at 45° C. for 17 hours. More of NaH (60% dispersion in mineral oil, 60 mg) was added based on the HPLC results, and then the mixture was heated at 45° C. for another 5.5 hours. The mixture was cooled to room temperature, saturated NaCl aqueous solution (2 mL) and water (15 mL) was added to quench the reaction. The mixture was extracted with EtOAc (4×20 mL). The combined organic solution was washed with brine, dried over Na$_2$SO$_4$, concentrated. The residue was purified by flash column chromatography on silica gel using 3-8% methanol in dichloromethane (biotage) to afford the product 6-O-mPEG$_9$-3-MEM-O-nalbuphine (207 mg) in 90% yield.

Synthesis of 6-O-mPEG$_9$-Nalbuphine (5) (n=9)

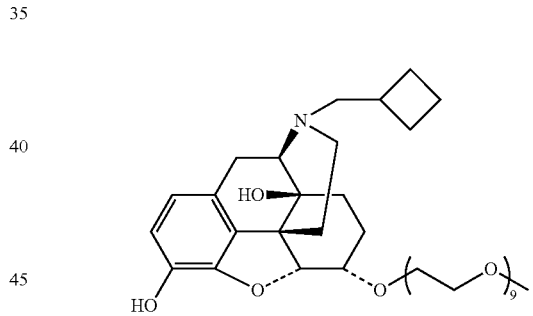

The above 6-O-mPEG$_9$-3-O-MEM-nalbuphine (4) (207 mg, 0.24 mmol) was stirred in 2 M HCl in methanol (33 mL) at room temperature for 17 hours. The mixture was diluted with water, and concentrated to remove the methanol. The aqueous solution was adjusted to 9.16 with 1 N NaOH, and extracted with dichloromethane (4×25 mL). The combined organic solution was washed with brine, dried over Na$_2$SO$_4$, concentrated. The residue was purified with flash column chromatography on silica gel using 3-8% methanol in dichloromethane to result in the product 6-O-mPEG$_9$-nalbuphine (4) (n=9) (129.3 mg) in 70% yield.

Example 3

Preparation of an Oligomer-Nalbuphine Conjugates—"Approach C"

PEG-Nalbuphine was prepared using a third approach. Schematically, the approach followed for this example is shown below.

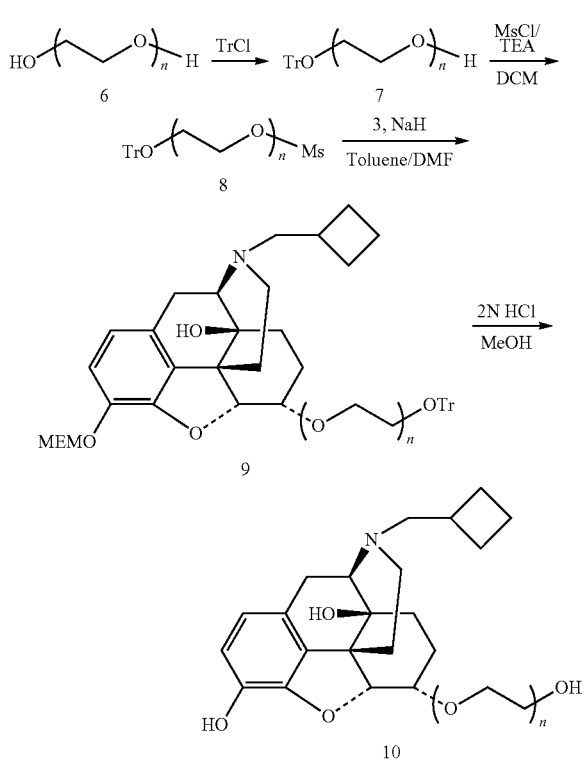

Synthesis of TrO-PEG$_5$-OH (7) (n=5)

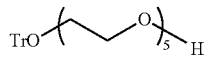

PEG$_5$-di-OH (6) (n=5) (5.88 g, 24.19 mmol) was dissolved in toluene (30 mL), and concentrated to remove toluene under reduced pressure. The residue was dried under high vacuum. Anhydrous DMF (40 mL) was added, followed by an addition of DMAP (0.91 g, 7.29 mmol) and TrCl (trityl chloride) (1.66 g, 5.84 mmol). The resulting mixture was heated at 50° C. for 22 hours. The reaction was concentrated to remove the solvents (high vacuum, 50° C.). The residue was mixed with water, and extracted with EtOAc (3×25 mL). The combined organic solution was washed with brine, dried over Na$_2$CO$_3$, concentrated. The residue was purified with flash column chromatography on silica gel to result in 1.29 g of product in 46% yield. The product was confirmed with $^1$H-NMR in CDCl$_3$.

Synthesis of TrO-PEG$_n$-OH (7) (n=Various)

Following a similar procedure for the preparation of TrO-PEG$_5$-OH, other TrO-PEG$_n$-OH were synthesized from the corresponding PEG$_n$-di-OH.

Synthesis of TrO-PEG$_5$-OMs (8) (n=5)

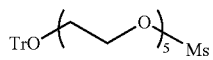

Methanesulfonyl chloride (0.35 mL, 4.48 mmol) was added dropwise to a stirred solution of TrO-PEG$_5$-OH (8) (n=5) (1.29 g, 2.68 mmol) and triethylamine (0.9 mL, 6.46 mmol) in dichloromethane (15 mL) at 0° C. After the addition, the resulting solution was stirred at room temperature for 16.5 hours. Water was added to quench the reaction. The organic phase was separated and the aqueous solution was extracted with dichloromethane (10 mL). The combined organic solution was washed with brine (3×30 mL), dried over Na$_2$SO$_4$ and concentrated to afford the product as oil (1.16 g) in 78% yield. The product (8) (n=5) was confirmed with $^1$H-NMR in CDCl$_3$.

Synthesis of TrO-PEG$_n$-OMs (8) (n=Various)

Following a similar procedure for the preparation of TrO-PEG$_5$-OMs, other TrO-PEG$_n$-OMs were synthesized from the corresponding TrO-PEG$_n$-OH.

Synthesis of 3-O-MEM-6-O-TrO-PEG$_4$-nalbuphine (9) (n=4)

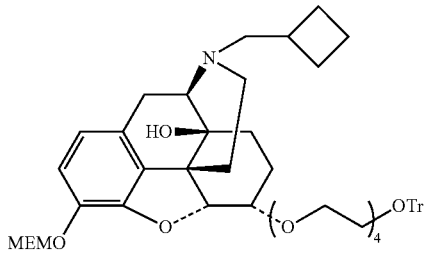

A round-flask was placed with 3-O-MEM-nalbuphine (3) (120 mg, 0.27 mmol) [previously prepared in accordance with the synthesis of compound (3) provided in Example 2], TrO-PEG$_4$-OMs (8) (n=4) (143.4 mg, 0.28 mmol) and toluene (40 mL). The mixture was concentrated to remove about 30 mL of toluene. NaH (60% dispersion in mineral oil, 150 mg, 3.75 mmol) was added, followed by an addition of anhydrous DMF (0.2 mL). The resulting mixture was heated at 45° C. for 4.5 hours. More of NaH (60% dispersion in mineral oil, 146 mg) was added, and the mixture was stirred at 45° C. for another 18 hours. The mixture was cooled to room temperature, was saturated with NaCl aqueous solution (2 mL), and water (15 mL) was added to quench the reaction. The mixture was extracted with EtOAc (4×20 mL). The combined organic solution was washed with brine, dried over Na$_2$SO$_4$, and concentrated. The residue was purified by flash column chromatography on silica gel using 0-10% methanol in dichloromethane (Biotage) to afford the product 3-O-MEM-6-O-TrO-PEG$_4$-nalbuphine (9) (n=4) (~150 mg).

Synthesis of 6-O—HO-PEG$_4$-Nalbuphine (10) (n=4)

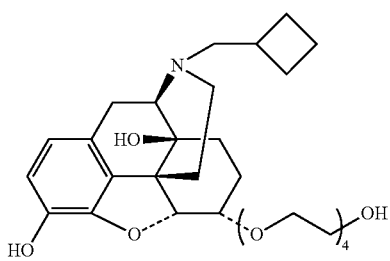

The above 6-O-TrO-PEG$_4$-3-O-MEM-nalbuphine (9) (n=4) (150 mg) was stirred in 2 M HCl in methanol (12 mL) at room temperature for one day. The mixture was diluted with water, and concentrated to remove the methanol. The aqueous solution was adjusted to PH 9.08 with NaOH, and extracted with EtOAc (3×20 mL). The combined organic solution was washed with brine, dried over Na$_2$SO$_4$, and concentrated. The residue was purified with flash column chromatography on silica gel to result in the product 6-O—OH-PEG$_4$-nalbuphine (10) (n=4) (26.9 mg). The product was analyzed with $^1$H-NMR, LC-Ms, HPLC.

Synthesis of 3-O-MEM-6-O-TrO-PEG$_5$-nalbuphine (9) (n=5)

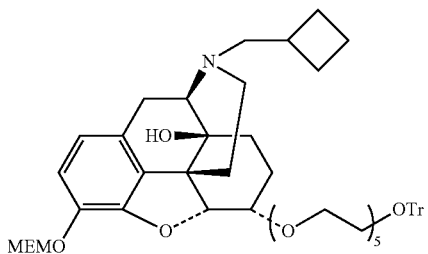

A round-flask was placed with 3-O-MEM-nalbuphine (3) (318 mg, 0.71 mmol) [previously prepared in accordance with the synthesis of compound (3) provided in Example 2], TrO-PEG$_5$-OMs (8) (n=5) (518.5 mg, 0.93 mmol) and toluene (100 mL). The mixture was concentrated to remove about 75 mL of toluene. NaH (60% dispersion in mineral oil, 313 mg, 7.8 mmol) was added, followed by an addition of anhydrous DMF (1.0 mL). The resulting mixture was stirred at room temperature for 30 minutes, and then at 60° C. for 19.5 hours. The mixture was cooled to room temperature, was saturated with NaCl aqueous solution (5 mL), and water (5 mL) was added to quench the reaction. The organic phase was separated and the aqueous was extracted with EtOAc. The combined organic solution was washed with brine, dried over Na$_2$SO$_4$, concentrated. The residue was purified by flash column chromatography on silica gel using 0-10% methanol in dichloromethane (Biotage) to afford the product 3-O-MEM-6-O-TrO-PEG$_5$-nalbuphine (718 mg). The product (9) (n=5) was impure, was used for the next step without further purification.

Synthesis of 6-O—HO-PEG$_5$-Nalbuphine (10) (n=5)

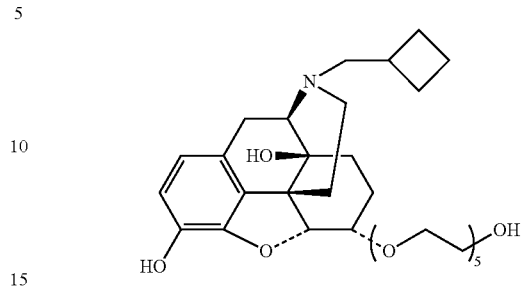

The above 6-O-TrO-PEG$_5$-3-O-MEM-nalbuphine (9) (n=5) (718 mg) was stirred in 2 M HCl in methanol (30 mL) at room temperature for 19 hours. The mixture was diluted with water, and concentrated to remove the methanol. The aqueous solution was adjusted to PH 9.16 with NaOH, extracted with DCM (3×20 mL). The combined organic solution was washed with brine, dried over Na$_2$SO$_4$, and concentrated. The residue was purified twice with flash column chromatography on silica gel to afford very pure product 6-O—HO-PEG$_5$-nalbuphine 10 (n=5) (139 mg) and less pure product (48 mg). The product was analyzed with $^1$H-NMR, LC-Ms, HPLC.

Example 4

Receptor Binding of PEG-Nalbuphine Conjugates

Using conventional receptor binding assay techniques, several molecules were assayed to determine binding activity at kappa, mu and delta opioid subtypes of opioid receptors.

Briefly, the receptor binding affinity of the nalbuphine and PEG-nalbuphine conjugates was measured using radioligand binding assays in CHO cells that heterologously express the recombinant human mu, delta or the kappa opioid receptor. Cells were plated in 24 well plates at a density of 0.2-0.3*10$^6$ cells/well and washed with assay buffer containing 50 mM Tris.HCl and 5 mM MgCl$_2$ (pH 7.4). Competition binding assays were conducted in whole cells incubated with increasing concentrations of test compounds in the presence of appropriate concentration of radioligand. 0.5 nM $^3$H Naloxone, 0.5 nM $^3$H Diprenorphine and 0.5 nM $^3$H DPDPE were used as the competing radioligands for mu, kappa and delta receptors respectively. Incubations were carried out for two hours at room temperature using triplicate wells at each concentration. At the end of the incubation, cells were washed with 50 mM Tris HCl (pH 8.0), solubilized with NaOH and bound radioactivity was measured using a scintillation counter.

Specific binding is determined by subtraction of the cpm bound in the presence of 50-100× excess of cold ligand. Binding data assays were analyzed using GraphPad Prism 4.0 and IC50 is generated by non-linear regression from dose-response curves. Ki values were calculated using the Cheng Prusoff equation using the Kd values from saturation isotherms as follows: Ki=IC50/(1+[Ligand]/Kd).

PEG conjugates of nalbuphine retain binding affinity to opioid receptors. Table 1 shows the binding affinity (Ki, in nM) for PEG conjugates of nalbuphine at the mu, delta and kappa opioid receptors. The loss in binding affinity following PEG conjugation is less than 15-fold that of parent nalbuphine at all three receptor subtypes. See Table 1. PEG conjugation results in a 10-15 fold loss in binding affinity at the mu and kappa opioid receptors, but not at the delta opioid receptors. Binding affinity at the delta opioid receptor is comparable, or even greater in some cases, than that of parent nalbuphine. See FIG. 1. The differential change in binding affinity at the three opioid receptor subtypes implies that the receptor selectivity of the nalbuphine conjugates is altered compared to the parent nalbuphine.

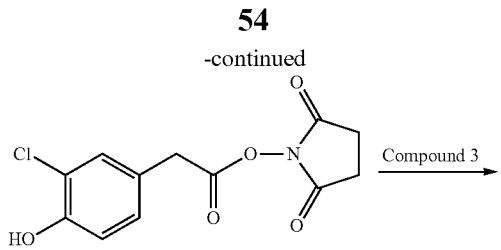

TABLE 1

| Molecule | Ki at KAPPA receptors (nM) | Fold vs Nalbuphine at KAPPA | Ki at MU Receptors (nM) | Fold vs Nalbuphine At MU | Ki at DELTA Receptors (nM) | Fold vs Nalbuphine At DELTA |
|---|---|---|---|---|---|---|
| Nalbuphine | 25.95 | 1 | 14.31 | 1 | 318.85 | 1 |
| 3-O-mPEG$_n$-Nalbuphine* | — | — | — | — | — | — |
| 6-O-mPEG$_3$-Nalbuphine | 218.1 | 8.40 | 27.41 | 1.92 | 163.30 | 0.51 |
| 6-O-mPEG$_4$-Nalbuphine |  |  | 17.54 | 1.23 | 148.90 | 0.47 |
| 6-O-mPEG$_5$-Nalbuphine | 35.56 | 1.37 | 35.09 | 2.45 | 147.70 | 0.46 |
| 6-O-mPEG$_6$-Nalbuphine | 246.9 | 9.51 | 44.28 | 3.09 | 130.00 | 0.41 |
| 6-O-mPEG$_7$-Nalbuphine | 346.1 | 13.34 | 77.94 | 5.45 | 313.80 | 0.98 |
| 6-O-mPEG$_8$-Nalbuphine | 282.2 | 10.87 | 79.55 | 5.56 | 167.50 | 0.53 |
| 6-O-mPEG$_9$-Nalbuphine | 186.1 | 7.17 | 122.30 | 8.55 | 157.70 | 0.49 |

*The "3-O-mPEG$_n$-nalbuphine" series of molecules prepared in Example 1 showed no detectable binding activity; molecules wherein a water-soluble, non-peptidic oligomer is covalently attached at the 3-O position are believed to have value when, for example, the covalent linkage is a degradable form of linkage. Some binding activity values in the above table have been replaced with values obtained under further optimized assay conditions. Although the original values are believed to be reliable and useful, they have been replaced here in the interest of brevity.

Example 5

Preparation of U50488 Conjugates

PEG-U50488 can be prepared following the approaches schematically shown below.

Example 5a: Synthesis of mPEG$_n$-O-U50488 Conjugates

Following the general schematic provided below, mPEG$_n$-O-U504488 conjugates can be prepared.

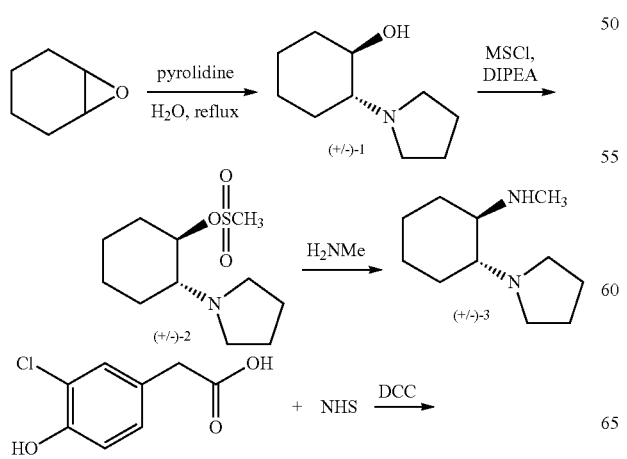

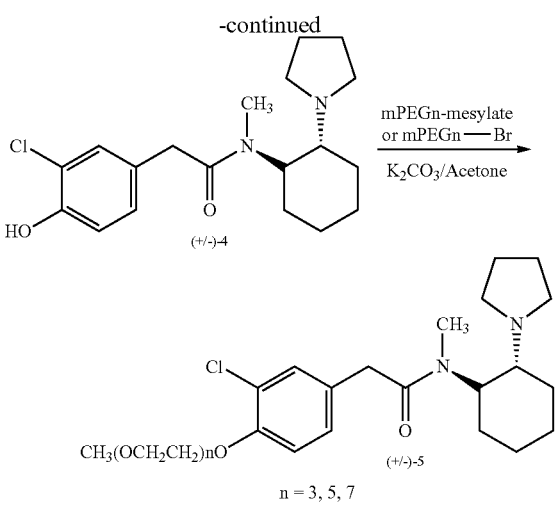

(+/−)-trans-2-(Pyrrolidin-1-yl)cyclohexanol ((+/−)-1): Pyrrolidine (4.26 g, 60 mmol) was added to a solution of cyclohexene oxide (1.96 g, 20 mmol) in H$_2$O (6 mL), and the resulting mixture was heated at 90° C. for 16 hours. After cooling, the solvent was removed under reduced pressure and the resulting residue was extracted with DCM (10 mL×3). The organic phases were combined and dried with anhydrous Na$_2$SO$_4$. After removing the Na$_2$SO$_4$ by filtration, the solvent was evaporated and the material dried under vacuum to afford the desired compound (+/−)-1 (3.3 g, 19.5 mmol, yield 98%). $^1$H NMR (CDCl$_3$) δ 4.06 (s, 1H), 3.45-3.30 (m, 1H), 2.75-2.63 (m, 2H), 2.62-2.50 (m, 2H), 2.51-2.42 (m, 1H), 1.90-1.58 (m, 8H), 1.45-1.15 (m, 4H).

(+/−)-trans-N-Methyl-2-(pyrrolidin-1-yl)cyclohexanamine ((+/−)-2): To a solution of compound (+/−)-1 (1.01 g, 6 mmol) and TEA (0.98 mL, 7 mmol) in DCM (20 mL) was added methanesulfonyl chloride (0.51 mL, 6.6 mmol) dropwise. The reaction mixture was stirred for 2 h at room temperature. The solvent was removed under reduced pressure, and 5 mL methylamine (40% in H$_2$O) was added at room temperature. The solution was stirred at room temperature for an additional 16 h. The reaction mixture was then added to DCM (50 mL) and washed with sat. NaHCO$_3$ solution (2×25 mL). The organic phases were combined and dried with anhydrous Na$_2$SO$_4$. After removing the Na$_2$SO$_4$ by filtration, the solvent was removed and the material dried under vacuum to afford the desired compound (+/−)-2 (1.0 g, 5.5 mmol, yield 91%). $^1$H NMR (CDCl$_3$) δ 2.61 (s, 1H), 2.49-2.30 (m, 6H), 2.29 (s, 3H), 2.09-1.96 (m, 2H), 1.67-1.52 (m, 7H), 1.11-1.02 (m, 3H).

(+/−)-N-methyl-N-[2-(pyrrolidin-1-yl)cyclohexyl]-2-(3-chloro-4-hydroxyphenyl)acetamide ((+/−)-4): 3-Chloro-4-hydroxyphenylacetic acid (186 mg, 1 mmol) and NHS (115 mg, 3 mmol) were dissolved in DCM (20 mL). Then DCC (1.1 mmol) was added into the solution and the reaction mixture was stirred at room temperature for 16 h during which a precipitate was formed. After the precipitate was removed by filtration, the resulting filtrate was mixed with compound (+/−)3 (182 mg, 1 mmol). The resulting solution was stirred at room temperature overnight. The solvent was removed under reduced pressure and the resulting residue was subjected to flash chromatography purification (MeOH/DCM=2%~18%) to give the desired product (+/−)-4 (120 mg, 0.34 mmol, yield 34%). $^1$H NMR (CDCl$_3$) δ 7.12 (s, 1H), 7.00-6.86 (m, 2H), 4.56 (s, 1H), 3.66-3.61 (m, 2H), 3.09-2.85 (m, 6H), 2.85 (s, 3H), 1.71-1.45 (m, 8H), 1.44-1.11 (m 4H). LC/MS 351.1 [M+H]$^+$.

(+/−)-N-methyl-N-[2-(pyrrolidin-1-yl)cyclohexyl]-2-(3-chloro-4-methoxy-tri(ethylene glycol)phenyl)acetamide ((+/−)-5a): Compound (+/−)-4 (50 mg, 0.14 mmol), methoxy tri(ethylene glycol) methanesulfonate (48.4 mg, 0.2 mmol) and anhydrous K$_2$CO$_3$ (70 mg, 0.5 mmol) were added to acetone (10 mL). The resulting mixture was stirred under reflux for 16 h. The solid was removed by filtration and the solvent was evaporated under reduced pressure. The resulting residue was subjected to flash chromatography purification (MeOH/DCM=2%~15%) to give the desired compound (+/−)-5a (30 mg, 0.06 mmol, yield 43%). $^1$H NMR (CDCl$_3$) δ 7.31 (s, 1H), 7.18 (d, 1H), 7.06 (d, 1H), 4.61-4.51 (m 1H), 4.19 (t, 2H), 3.90 (t, 2H), 3.76-3.44 (m, 10H), 3.36 (s, 3H), 2.95-2.83 (m, 6H), 2.11-1.19 (m, 12H). LC/MS 497.2 [M+H]$^+$ (+/−)-N-methyl-N-[2-(pyrrolidin-1-yl)cyclohexyl]-2-(3-chloro-4-methoxy-penta(ethylene glycol)phenyl)acetamide ((+/−)-5b): Compound (+/−)-4 (80 mg, 0.23 mmol), methoxy penta(ethylene glycol) methanesulfonate (108.9 mg, 0.33 mmol) and anhydrous K$_2$CO$_3$ (112 mg, 0.8 mmol) were added to acetone (15 mL). The mixture was stirred under reflux for 16 h. The solid was removed by filtration and the solvent was evaporated under reduced pressure. The resulting residue was subjected to flash chromatography purification (MeOH/DCM=2%~15%) to give the desired compound (+/−)-5a (60 mg, 0.10 mmol, yield 45%). $^1$H NMR (CDCl$_3$) δ 7.25 (s, 1H), 7.10 (d, 1H), 6.85 (d, 1H), 4.55-4.45 (m 1H), 4.14 (t, 2H), 3.87 (t, 2H), 3.81-3.42 (m, 18H), 3.37 (s, 3H), 2.90-2.35 (m, 6H), 2.09-1.15 (m, 12H). LC/MS 585.3 [M+H]$^+$.

(+/−)-N-methyl-N-[2-(pyrrolidin-1-yl)cyclohexyl]-2-(3-chloro-4-methoxy-hexa(ethylene glycol)phenyl)acetamide ((+/−)-5c): Compound (+/−)-4 (50 mg, 0.23 mmol), methoxy hexa(ethylene glycol) methanesulfonate (150 mg, 0.37 mmol) and anhydrous K$_2$CO$_3$ (112 mg, 0.8 mmol) were added to acetone (15 mL). The mixture was stirred under reflux for 16 h. The solid was removed by filtration and the solvent was evaporated under reduced pressure. The resulting residue was subjected to flash chromatography purification (MeOH/DCM=2%~15%) to give the desired compound (+/−)-5c (61 mg, 0.09 mmol, yield 39%). $^1$H NMR (CDCl$_3$) δ 7.27 (s, 1H), 7.16 (d, 1H), 6.88 (d, 1H), 4.72-4.51 (m 1H), 4.16 (t, 2H), 3.89 (t, 2H), 3.79-3.49 (m, 26H), 3.38 (s, 3H), 3.18-2.53 (m, 6H), 2.10-1.12 (m, 12H). LC/MS 673.4 [M+H]$^+$.

Example 5B: Synthesis of di-mPEG$_n$-CH$_2$—U50488 Conjugates

Following the general schematic provided below, di-mPEG$_n$-CH$_2$—U504488 conjugates can be prepared.

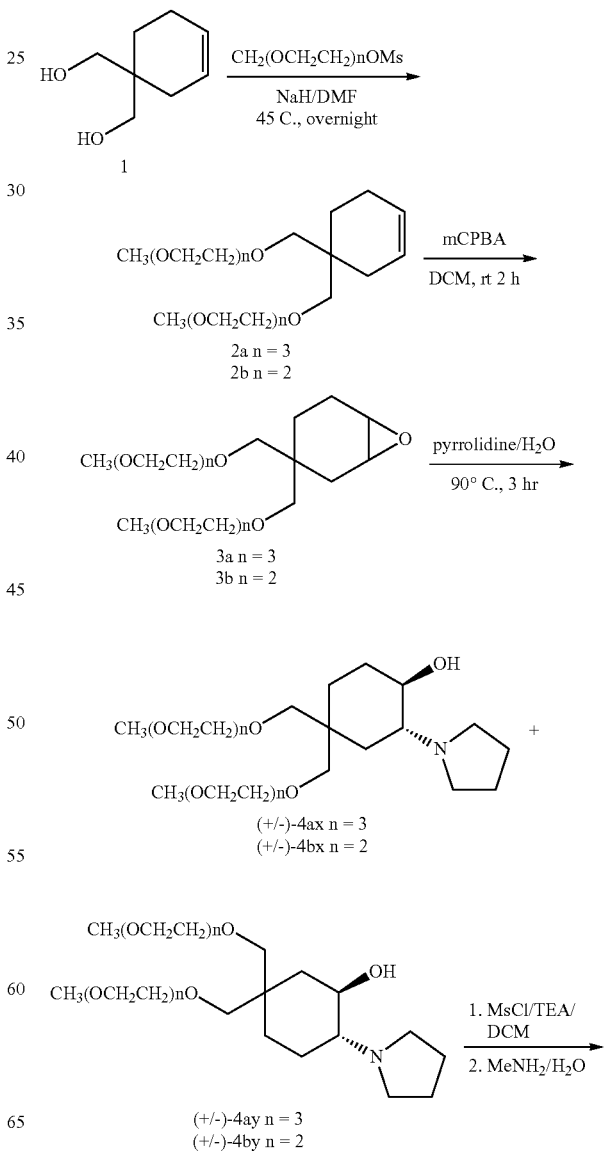

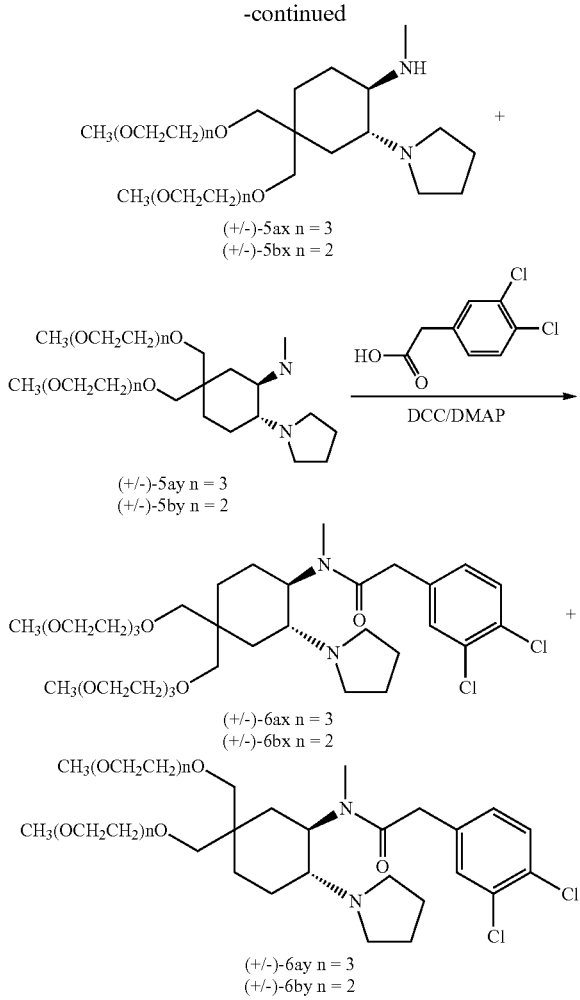

3-Cyclohexene 1,1-dimethanol methoxy tri(ethylene glycol) ether (2a) : 3-Cyclohexene 1,1-dimethanol 1 (284 mg, 2 mmol) was dissolved in anhydrous DMF (6 mL). At room temperature, NaH (60% in mineral oil, 320 mg, 8 mmol) was added and the solution was stirred for an additional for 10 minutes. Methoxy tri(ethylene glycol) mesylate (1.21 g, 5 mmol) was added to the solution. The reaction solution was stirred at 45° C. for 18 h and then saturated NH$_4$Cl solution (30 mL) was added to the solution. The solution was extracted with EtOAc (20 mL×2). The organic phases were combined, dried with Na$_2$SO$_4$, filtered and the solvent removed under reduced pressure to give compound 2a (850 mg, 1.96 mmol, 98% yield). $^1$H NMR (CDCl$_3$) δ 5.62-5.58 (m, 2H), 3.66-3.51 (m, 24H), 3.38 (s, 6H), 3.34 (d, 2H), 3.25 (d, 2H), 2.01 (m, 2H), 1.87 (m, 2H), 1.52 (t, 2H). LC/MS 435 [M+H]$^+$, 452 [M+NH$_4$]$^+$, 457 [M+Na]$^+$. ]3-Cyclohexene 1,1-dimethanol methoxy di(ethylene glycol) ether (2b): 3-Cyclohexene 1,1-dimethanol (426 mg, 3 mmol) 1 was dissolved in anhydrous DMF (9 mL). At room temperature, NaH (60% in mineral oil, 480 mg, 12 mmol) was added and the solution was stirred for an additional 10 minutes. Methoxy di(ethylene glycol) mesylate (1.5 g, 7.5 mmol) was added to the solution. The reaction solution was stirred at 45° C. for 18 h and then saturated NH$_4$Cl solution (30 mL) was added to the solution. The solution was extracted with EtOAc (20 mL×2). The organic phases were combined, dried with Na$_2$SO$_4$, filtered, and the solvent removed under reduced pressure to give compound 2b (1.18 g, 2.9 mmol, 98% yield). $^1$H NMR (CDCl$_3$) δ 5.64-5.56 (m, 2H), 3.66-3.54 (m, 16H), 3.35 (s, 6H), 3.33 (d, 2H), 3.28 (d, 2H), 1.99 (m, 2H), 1.87 (m, 2H), 1.53 (t, 2H).

3,3-Di[methoxy tri(ethylene glycol)methyl]-7-oxabicyclo[4.1.0]heptanes (3a): Compound 2a (850 mg, 1.96 mmol) was dissolved in DCM (20 mL). At room temperature, mCPBA (77% max, 0.75 g, ~3 mmol) was added to the solution. The reaction mixture was stirred at room temperature for 3.5 h. Sat. Na$_2$S$_2$O$_3$ solution (10 mL) was added to the solution and stirring occurred for an additional 10 min. The resulting solution was extracted with DCM (20 mL×2). The organic phases were combined, dried with Na$_2$SO$_4$, filtered, and the solvent removed under reduced pressure to give compound 3a (870 m g, 1.86 mmol, 95% yield). $^1$H NMR (CDCl$_3$) δ 3.66-3.55 (m, 24H), 3.38 (s, 6H), 3.27-3.12 (m, 6H), 1.99-1.67 (m, 6H). LC/MS 451 [M+H]$^+$, 468 [M+NH$_4$]$^+$, 473 [M+Na]$^+$.

3,3-Di[methoxy di(ethylene glycol)methyl]-7-oxabicyclo[4.1.0]heptanes (3b): Compound 2b (1.18 g, 3.41 mmol) was dissolved in DCM (20 mL). At room temperature, mCPBA (77% max, 1.3 g, ~5.2 mmol) was added to the solution. The reaction solution was stirred at room temperature for 3.5 h. Sat. Na$_2$S$_2$O$_3$ solution (15 mL) was added to the solution and stirring occurred for an additional 10 min. The resulting solution was extracted with DCM (20 mL×2). The organic phases were combined, dried with Na$_2$SO$_4$, filtered, and the solvent removed under reduced pressure to give compound 3b (1.27 g, 3.12 mmol, 92% yield). $^1$H NMR (CDCl$_3$) δ 3.65-3.54 (m, 24H), 3.38 (s, 6H), 3.27-3.10 (m, 6H), 2.00-1.68 (m, 6H).

Trans-(+/−)-4 or -5-di[methoxy tri(ethylene glycol) methyl]-2-(1-pyrrolidinyl)-cyclohexanol (4a): Compound 3a (870 mg, 1.93 mmol) and pyrrolidine (2.5 mL) were added to water (8 mL) and heated to reflux for 5 h. The resulting solution was extracted with DCM (10 mL×2). The organic phases were combined, dried with Na$_2$SO$_4$, filtered, and the solvent removed under reduced pressure to give 4a as a mixture of 4ax and 4ay (910 mg total). The product was used in the next reaction without further purification.

Trans-(+/−)-4 or -5-di[methoxy di(ethylene glycol) methyl]-2-(1-pyrrolidinyl)-cyclohexanol (4b): Compound 3b (1.27 g, 3.12 mmol) and pyrrolidine (2.5 mL) were added to water (8 mL) and heated to reflux for 5 h. The resulting solution was extracted with DCM (10 mL×2). The organic phases were combined, dried with Na$_2$SO$_4$, filtered, and the solvent removed under reduced pressure to give 4b as a mixture of 4bx and 4by (1.3 g total). The product was used in the next reaction without further purification.

Trans-(+/−)-4 or -5-di[methoxy tri(ethylene glycol) methyl]-N-methyl-2-(1-pyrrolidinyl)-cyclohexanamine (5a): Compound 4a (910 mg, 1.74 mmol) was dissolved in DCM (20 mL), and TEA (0.42 mL, 3 mmol) was added. At room temperature, methanesulfonyl chloride (0.16 mL, 2 mmol) was added dropwise. After stirring was continued overnight at room temperature, the resulting mixture was evaporated under reduced pressure. The resulting residue was dissolved in methylamine (40% w/w in water, 6 mL) and the solution was stirred at room temperature for 30 h. The solution was then extracted with DCM (10 mL×2). The organic phases were combined, dried with Na$_2$SO$_4$, filtered, and the solvent removed under reduced pressure to give 5a as a mixture of 5ax and 5ay. The product was used in the next reaction without further purification.

Trans-(+/−)-4 or -5-di[methoxy di(ethylene glycol) methyl]-N-methyl-2-(1-pyrrolidinyl)-cyclohexanamine (5b): Compound 4b (1.3 g, 3 mmol) was dissolved in DCM (20 mL), and TEA (0.84 mL, 6 mmol) was added. At room temperature, methanesulfonyl chloride (0.28 mL, 3.5 mmol) was added dropwise. After stirring was continued overnight at room temperature, the resulting mixture was evaporated under reduced pressure. The obtained residue was dissolved in methylamine (40% w/w in water, 6 mL) and the solution was stirred at room temperature for 30 h. The resulting solution was then extracted with DCM (10 mL×2). The organic phases were combined, dried with $Na_2SO_4$, filtered, and the solvent removed under reduced pressure to give 5b as a mixture of 5bx and 5by. The product was used in the next reaction without further purification.

Trans-(+/−)-4 or -5-di[methoxy tri(ethylene glycol)methyl]-N-methyl-N-[2-(pyrrolidin-1-yl)cyclohexyl]-2-(3,4-dichloro)acetamide (6a): 3,4-Dichlorophenylacetic acid (410 mg, 2 mmol), compound 5a (926 mg, 1.74 mmol), and DMAP (10 mg) were dissolved in DCM (10 mL). Then DCC (515 mg, 2.5 mmol) was added to the solution and the reaction mixture was stirred at room temperature for 4 h during which a precipitate formed. After the precipitate was removed by filtration, the resulting filtrate solvent was evaporated and the residue was subjected to flash chromatography purification (MeOH/DCM=2% 8%) to give the desired product 6a as a mixture of 6ax and 6ay (477 mg total, 0.34 mmol, yield 20%). $^1$H NMR (CDCl3) δ 7.39-7.33 (m, 2H), 7.15-7.10 (m, 1H), 3.71-3.51 (m, 28H), 3.42-3.16 (m, 3H), 3.35 (s, 6H), 2.82, 2.79 (s, s, 3H total, ratio 3:5), 2.70-2.30 (m, 5H), 1.73-1.17 (m, 11H). LC/MS 721 $[M+H]^+$, 743 $[M+Na]^+$.

Trans-(+/−)-4 or -5-di[methoxy di(ethylene glycol)methyl]-N-methyl-N-[2-(pyrrolidin-1-yl)cyclohexyl]-2-(3,4-dichloro)acetamide (6b): 3,4-Dichlorophenylacetic acid (707 mg, 3.45 mmol), compound 5b (1.33 g, 2.98 mmol), and DMAP (10 mg) were dissolved in DCM (10 mL). Then DCC (865 mg, 4.2 mmol) was added to the solution and the reaction mixture was stirred at room temperature for 4 h during which a precipitate formed. After the precipitate was removed by filtration, the resulting filtrate solvent was evaporated and the residue was subjected to flash chromatography purification (MeOH/DCM=2%~8%) to give the desired product 6b as a mixture of 6bx and 6by (306 mg total, 0.49 mmol, yield 16%). $^1$H NMR (CDCl3) δ 7.33-7.27 (m, 2H), 7.06-7.04 (m, 1H), 3.65-3.46 (m, 20H), 3.42-3.12 (m, 3H), 3.37 (s, 6H), 2.76, 2.74 (s, s, 3H total, ratio 1.1:1), 2.72-2.24 (m, 5H), 1.71-1.07 (m, 11H). LC/MS 633 $[M+H]^+$, 655 $[M+Na]^+$.

Example 6

Preparation of an Oligomer-U69593 Conjugates

PEG-U69593 can be prepared following the approach schematically shown below. Conventional organic synthetic techniques are used in carrying out the approach.

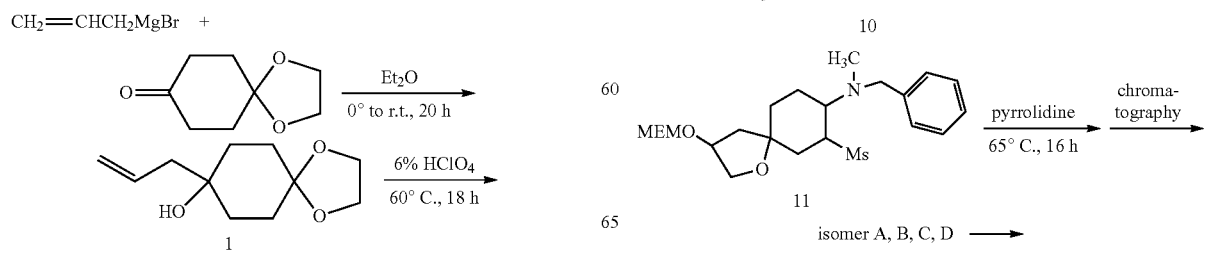

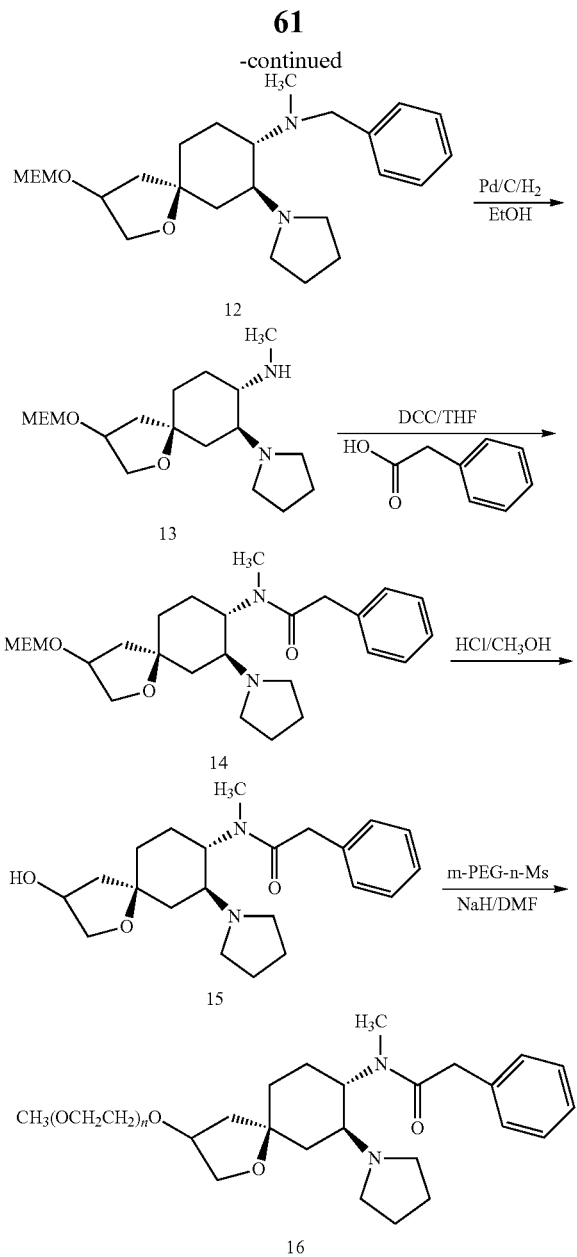

Example 7

Preparation of Conjugates Other than with Nalbuphine, U50488, and U69593

Conjugates of opioid agonists other than nalbuphine, U50488 and U69593 can be prepared wherein the general synthetic scheme and procedures set forth in Example 1 can be followed except that an opioid agonist of Formula I is substituted for nalbuphine, U50488 and U69593.

Example 8

In Vitro Efficacy of PEG-Nalbuphine Conjugates

The in vitro efficacy of PEG-nalbuphine conjugates was determined using a GTPγS binding assay in CHO cells expressing the recombinant human mu or delta opioid receptors or HEK cells expressing the recombinant human kappa opioid receptor. Test compound and/or vehicle was preincubated with the cell membranes and 3 µM GDP in modified HEPES buffer (pH 7.4) for 20 minutes, followed by addition of SPA beads for another 60 minutes at 30° C. The reaction is initiated by 0.3 nM [$^{35}$S]GTPγS for an additional 30 minutes incubation period. Test compound-induced increase of [$^{35}$S]GTPγS binding by 50 percent or more (≥50%) relative to the receptor subtype-specific agonist response indicates possible opiate receptor agonist activity. 0.1 µM DPDPE, 1 µM U-69593 and 1 µM DAMGO were used as the specific agonists for the delta, kappa and mu opioid receptors respectively. Opioid receptor antagonist activity was measured using inhibition of agonist-induced increase of [$^{35}$S]GTPγS binding response by 50 percent or more (≥50%). Nalbuphine, 6-O-mPEG$_3$-Nalbuphine, 6-O-mPEG$_6$-Nalbuphine, 6-O-mPEG$_9$-Nalbuphine were screened at concentrations of 10, 1, 0.1, 0.01 and 0.001 µM in both agonist and antagonist mode. $EC_{50}$ or $IC_{50}$ values were calculated from the dose-response curves as a measure of the agonist or antagonist activity of the test compounds respectively.

Table 2 shows the $EC_{50}/IC_{50}$ values of nalbuphine and PEG-nalbuphine conjugates to activate or inhibit GTPγS binding, thus reflecting their agonist or antagonist activity. PEG-nalbuphine conjugates are full agonists at kappa opioid receptors and antagonists at mu opioid receptors, similar to the pharmacological profile of nalbuphine. The $EC_{50}$ of 6-O-mPEG$_3$-Nalbuphine was similar to that of nalbuphine at the kappa opioid receptor, suggesting no loss of efficacy at this PEG size. Beyond a PEG size of 3, the efficacy of the PEG-nalbuphine conjugates at the kappa opioid receptor decreased as a function of PEG size, as indicated by the increase in $EC_{50}$ values of 6-O-mPEG$_6$-Nalbuphine, and 6-O-mPEG$_9$-Nalbuphine. PEG-nalbuphines appeared to have an antagonist potency at the mu opioid receptor comparable to that of the parent nalbuphine. At the delta opioid receptor, 6-O-mPEG$_9$-Nalbuphine, acted as a weak antagonistic, however, nalbuphine, 6-O-mPEG$_3$-Nalbuphine, 6-O-mPEG$_6$-Nalbuphine, had no effect at the delta opioid receptor.

TABLE 2

PEG-nalbuphine Conjugates Retain the in vitro Pharmacological Properties of Parent Nabuphine

| | Functional Assay GTP-γS Binding | | |
|---|---|---|---|
| Molecule | Kappa Agonist EC50 (nM) | Mu Antagonist IC50 (nM) | Delta IC50 (nM) |
| Nalbuphine | 25.1 | 752 | — |
| 6-O-mPEG$_3$-Nalbuphine | 26.80 | 398.0 | — |
| 6-O-mPEG$_6$-Nalbuphine | 164.00 | 284.0 | — |
| 6-O-mPEG$_9$-Nalbuphine | 485.00 | 1010.0 | 8970.0 |

Example 9

In Vitro Permeability

The in vitro permeability of PEG-nalbuphine conjugates was measured using a bi-directional transport assay in Caco-2 cells. PEG-nalbuphine conjugates were added at a concentration of 10 µM to either the apical or basolateral compartment of Caco-2 monolayers and incubated for two hours. At the end of the incubation, the concentrations in the apical and basolateral compartments were measured using LC-MS. Permeability was calculated as Papp=J/A.Co, where Papp is the apparent permeability in cm/s, J is the flux in moles/s, A is the surface area of the insert in cm$^2$ and Co is the initial concentration in moles/cm$^3$.

Figure 2A:
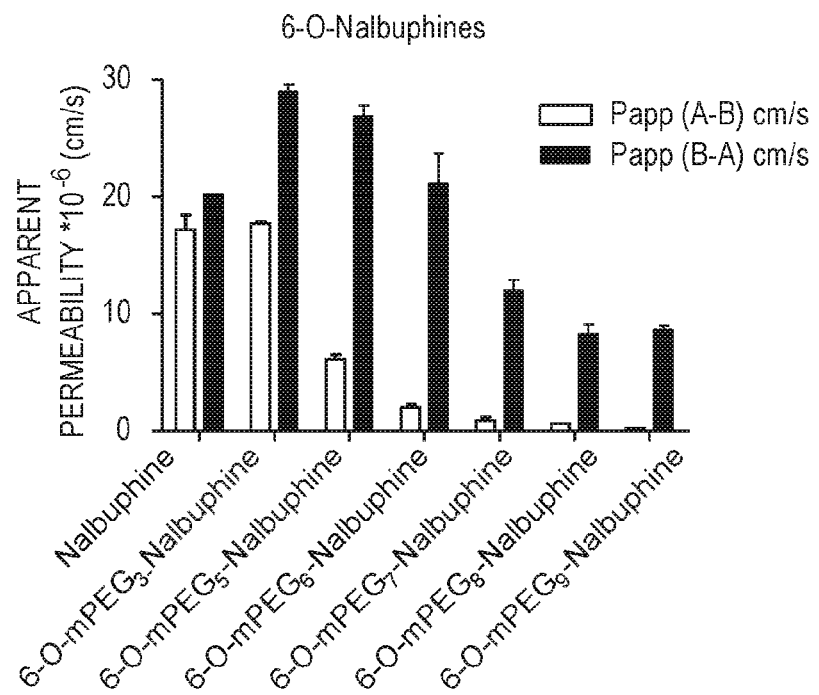
FIG. 2A and FIG. 2B are graphs showing the in vitro permeability and efflux ratios of various nalbuphine conjugates, as described in greater detail in Example 9. These graphs show that (i) the permeability of PEG-nalbuphine conjugates in Caco-2 cells decreases as a function of PEG chain length (FIG. 2A) and, (ii) PEG-nalbuphine conjugates are likely substrates for efflux transporters (FIG. 2B).

FIG. 2A shows the in vitro apparent permeability of PEG-nalbuphine conjugates measured in Caco-2 cells in the A-B (apical-basolateral) and B-A (basolateral-apical) direction. A-B permeability, and to a lesser extent, B-A permeability decrease with increasing PEG chain length. The A-B permeability, which represents mucosal-serosal transport in vivo is greater than $1*10^{-6}$ cm/s for all compounds, indicating that nalbuphine and PEG-nalbuphine conjugates are likely to be well absorbed orally.

Figure 2B:
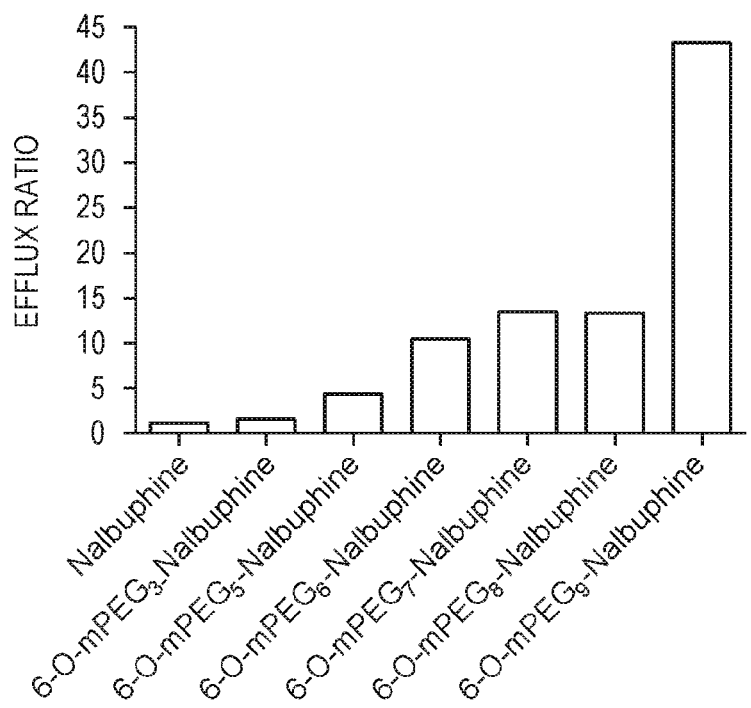

FIG. 2B shows the efflux ratio of PEG-nalbuphine conjugates, calculated as a ratio of B-A/A-B permeabilities. An efflux ratio greater than unity is a reflection of an asymmetry in transport in the apical-basolateral directions and suggests a role for transporters in the overall permeability. The efflux ratio for the parent nalbuphine is close to unity, indicating that it is not a likely substrate for transporters. However, 6-O-mPEG$_5$-Nalbuphine, 6-O-mPEG$_6$-Nalbuphine, 6-O-mPEG$_7$-Nalbuphine, 6-O-mPEG$_8$-Nalbuphine, and 6-O-mPEG$_9$-Nalbuphine have an efflux ratio greater than 3, and hence are likely substrates for efflux transporters in Caco-2 cells.

Example 10

In Vivo Brain Penetration of PEG-Nalbuphine Conjugates

The ability of the PEG-nalbuphine conjugates to cross the blood brain barrier (BBB) and enter the CNS was measured using the brain:plasma ratio in rats. Briefly, rats were injected intravenously with 25 mg/kg of nalbuphine, PEG-nalbuphine conjugate or atenolol. An hour following injection, the animals were sacrificed and plasma and the brain were collected and frozen immediately. Following tissue and plasma extractions, concentrations of the compounds in brain and plasma were measured using LC-MS/MS. The brain:plasma ratio was calculated as the ratio of measured concentrations in the brain and plasma. Atenolol, which does not cross the BBB was used as a measure of vascular contamination of the brain tissue.

Figure 3:
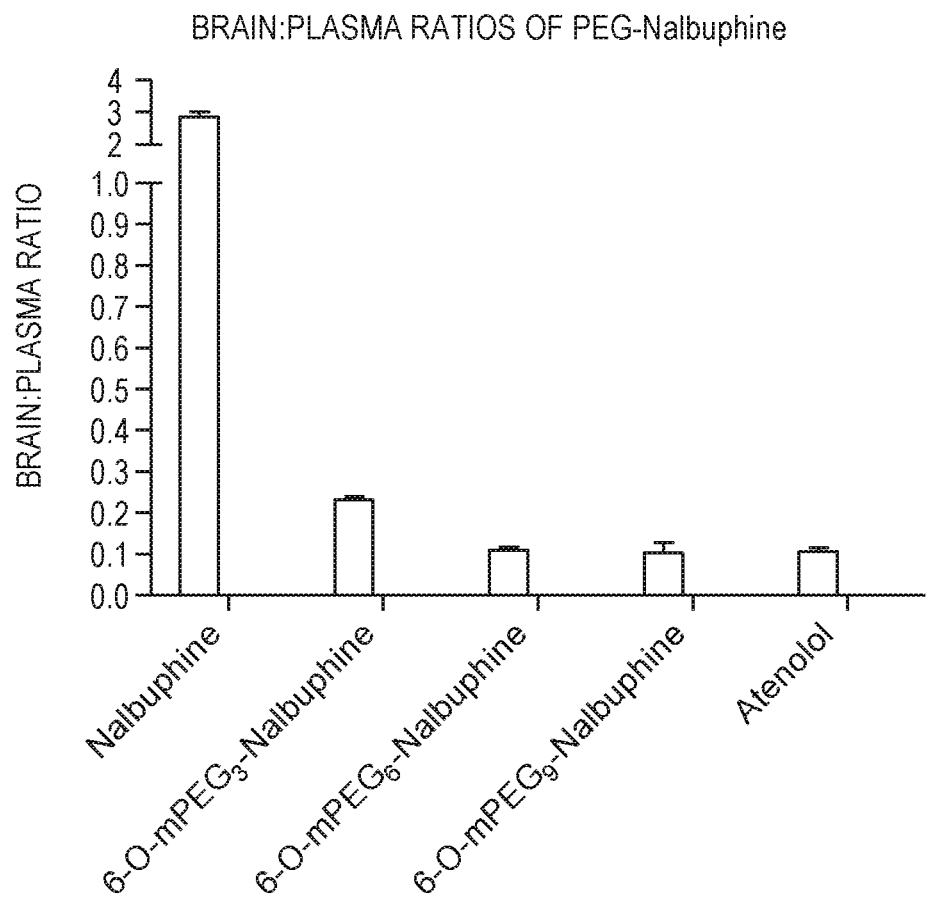
FIG. 3 is a graph showing brain:plasma ratios of various PEG-nalbuphine conjugates, as described in greater detail in Example 10. This graph shows PEG conjugation results in a decrease in the brain:plasma ratios of nalbuphine.

FIG. 3 shows the ratio of brain:plasma concentrations of PEG-nalbuphine conjugates. The brain:plasma ratio of nalbuphine was 2.86:1, indicating a nearly 3 fold greater concentration of nalbuphine in the brain compared to the plasma compartment. PEG conjugation significantly reduced the entry of nalbuphine into the CNS as evidenced by a lower brain:plasma ratio of the PEG-nalbuphine conjugates. Conjugation with 3 PEG units reduced the brain:plasma ratio to 0.23:1, indicating that the concentration of 6-O-mPEG$_3$-Nalbuphine in brain was approximately 4 fold less than that in the plasma. 6-O-mPEG$_6$-Nalbuphine and 6-O-mPEG$_9$-Nalbuphine were significantly excluded from the CNS, since their brain:plasma ratios were not significantly different from the vascular marker, atenolol.

Example 11

Preparation of Oligomer-Fentanyl Conjugates mPEG$_n$-O-fentanyl conjugates can be prepared following the approaches schematically shown below. Conventional organic synthetic techniques are used in carrying out the synthetic approaches.

An exemplary approach for preparing the following structures, where the PEG oligomer is positioned, i.e., covalently attached, at the N-(1-(2-phenylethyl)piperidin-4-yl) phenyl group:

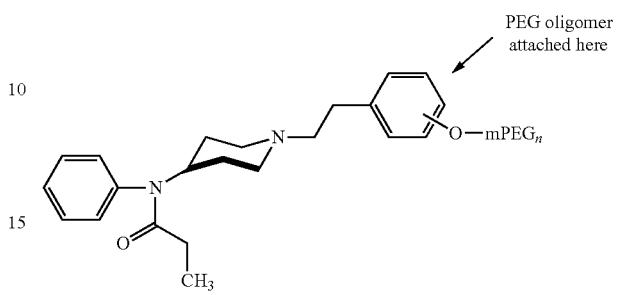

[wherein mPEG$_n$ is —(CH$_2$CH$_2$O)$_n$—CH$_3$ and n is an integer from 1 to 9], is provided below.

Scheme 11-A

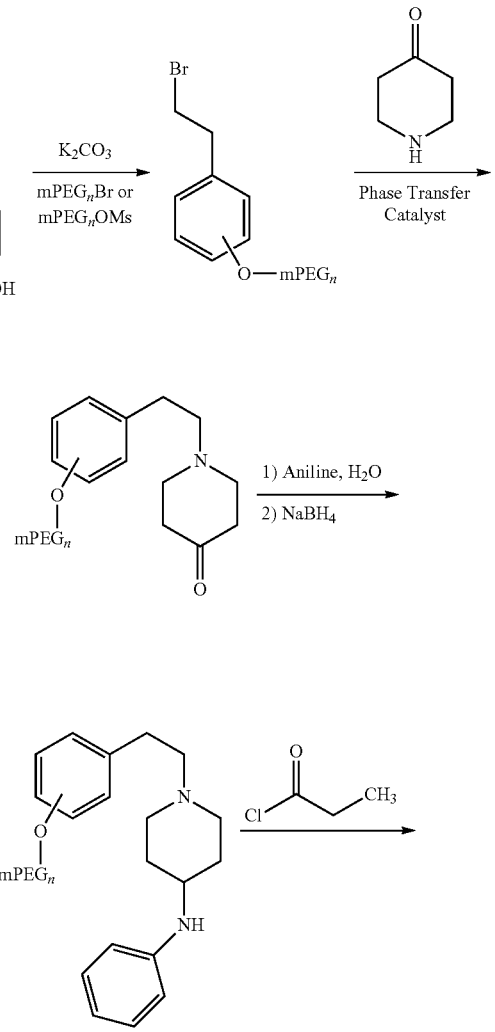

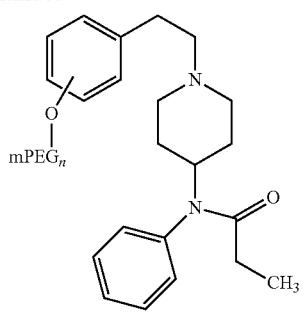

In the above approach, the starting material is a (haloethyl)hydroxybenzene, where the hydroxy group forms the point of attachment for the PEG oligomer. The (haloethyl)hydroxybenzene, i.e., (bromoethyl)hydroxybenzene, is reacted with a mesylated or halogenated activated mPEG oligomer, thereby forming the desired PEG-oligomer modified (haloethyl)benzene intermediate. This intermediate is then reacted with piperidin-4-one in the presence of a phase transfer catalyst; the bromo group reacts at the piperidine-4-one nitrogen to form a next intermediate, 1-(mPEG$_{olig}$-phenylethyl)piperidine-4-one. The ketone functionality is then reduced in the presence of a reducing agent such as sodium borohydride, and converted to an amino group, i.e., N-phenyl-piperidin-4-amine, by reaction with aniline. Finally, the secondary amino group is converted to a tertiary amine by reaction with propionyl chloride to form the desired product as indicated in the scheme above.

The subject mPEG$_n$-O-fentanyl conjugates having the PEG oligomer positioned at the N-(1-(2-phenylethyl)piperidin-4-yl) phenyl group were synthesized using a reaction scheme that was slightly modified from Scheme 11-A above as illustrated in Scheme 11-B below:

Scheme 11-B

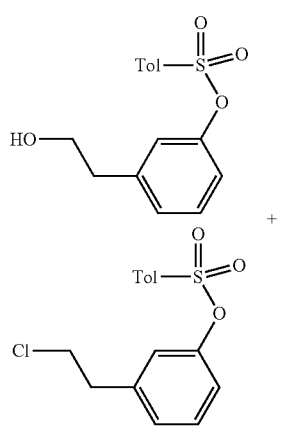

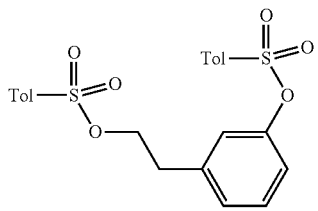

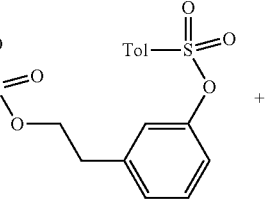

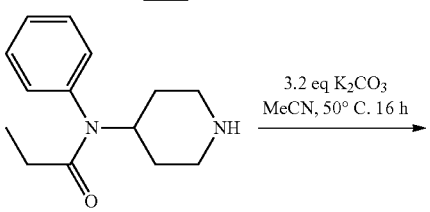

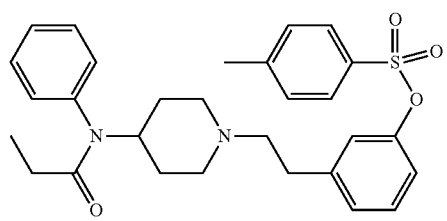

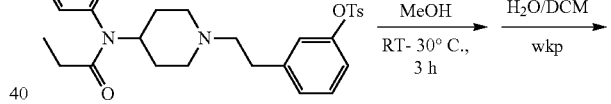

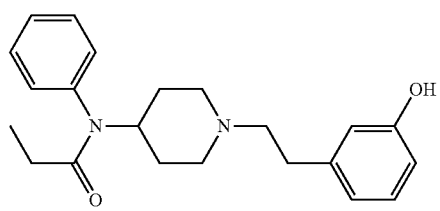

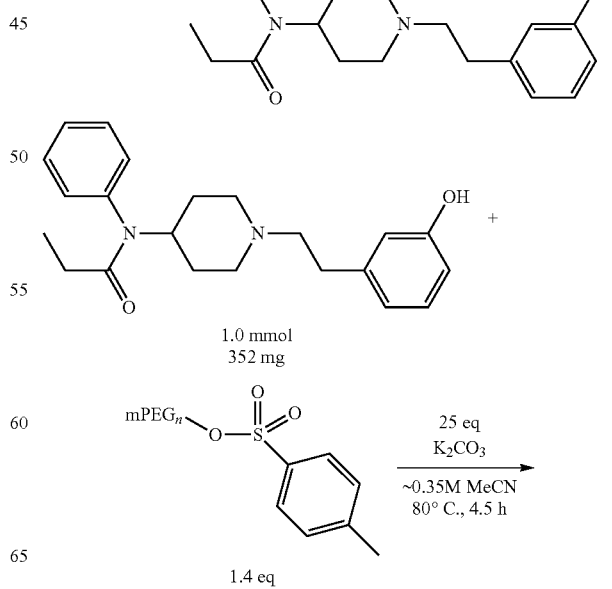

67
-continued

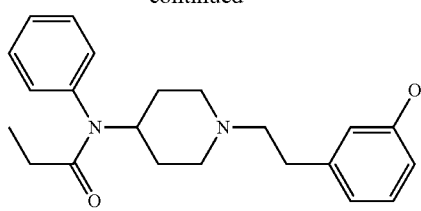

The above approach employs tosyl (p-toluenesulfonate) leaving groups at various steps in the synthesis. The desired PEG-oligomer conjugates (n=1 to 9) were assembled by reacting di-tosylated 3-(2-hydroxyethyl)phenol with N-phenyl-N-(piperidin-4-yl)propionamide to form N-(1-(3-hydroxyphenylethyl)piperidin-4-yl)-N-phenylpropionamide, in tosylated form, followed by removal of the tosyl group. The PEG-oligomer group was then introduced into the molecules at the phenyl hydroxyl position by reaction of N-(1-(3-hydroxyphenylethyl)piperidin-4-yl)-N-phenylpropionamide with a molar excess of mPEG$_{olig}$-tosylate to form the desired mPEG$_n$-O-fentanyl conjugates. Ratios of reactants and reaction conditions generally employed are provided in the reaction scheme above.

An exemplary approach for providing the following structures, where the PEG oligomer is positioned, i.e., covalently attached, at the N-phenyl group, is set forth below:

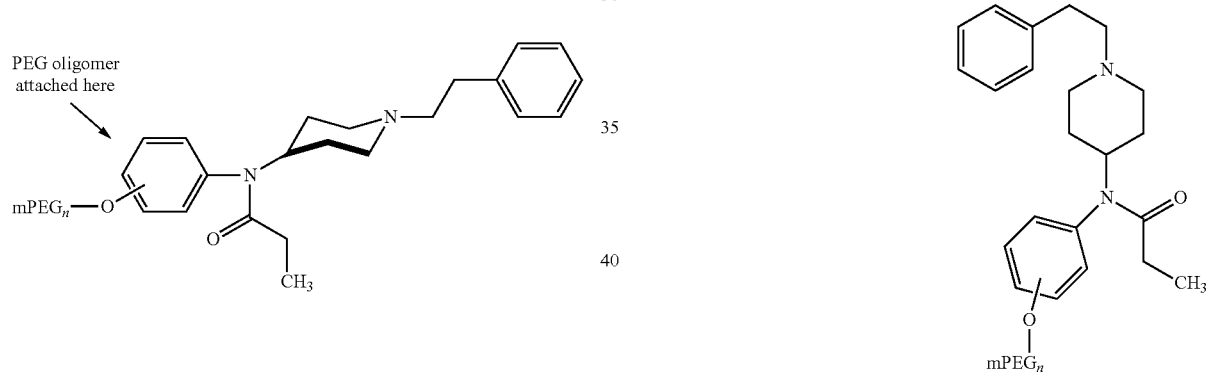

Scheme 11-C

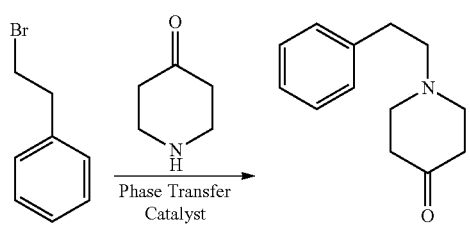

a)

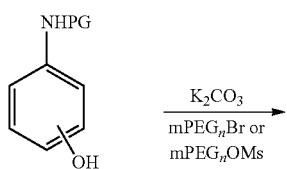

b)

PG = Protecting Group

68
-continued

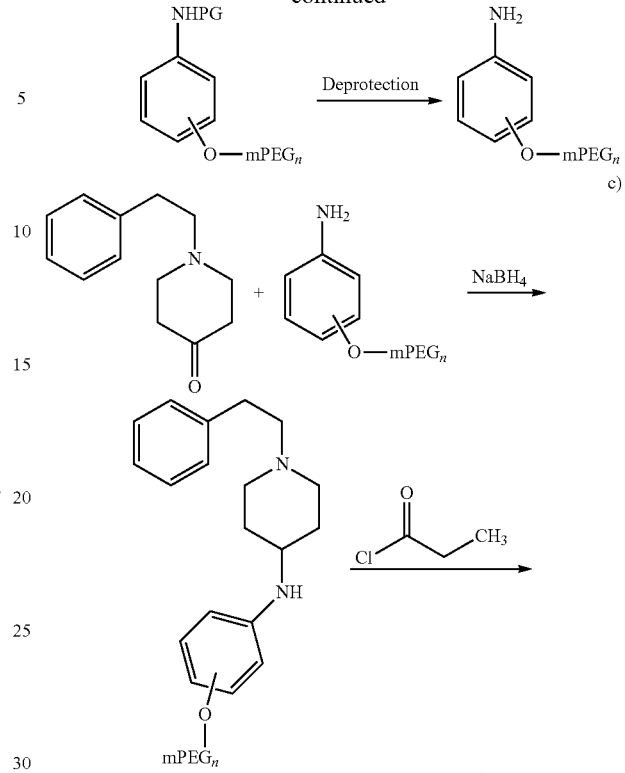

c)

The above exemplary approach for forming an mPEG$_n$-O-fentanyl conjugate having the PEG oligomer positioned at the N-phenyl ring starts with, e.g., 2-bromoethylbenzene, as the starting material. The 2-bromoethylbenzene is reacted with piperidin-4-one in the presence of a phase transfer catalyst to thereby form the resulting 1-phenethylpiperidin-4-one. The 1-phenethylpiperidin-4-one is coupled to mPEG$_{olig}$-substituted aniline, which is prepared by taking N-protected hydroxyaniline and reacting it with activated mPEG oligomer, such as bromomethoxyPEG$_{olig}$ or mPEG$_{oligo}$ mesylate, followed by removal of the protecting group (see step (b) above). As indicated in reaction step (c) above, 1-phenethylpiperidin-4-one is reacted with mPEG$_{olig}$-substituted aniline in the presence of a reducing agent to convert the keto group into an amine to form the intermediate, 1-phenylethylpiperidin-4-ylamino-mPEG$_{olig}$obenzene. Finally, the secondary amino group is converted to a tertiary amine by reaction with propionyl chloride to form the desired product as indicated in the scheme above.

The subject mPEG$_n$-O'-fentanyl conjugates having the PEG oligomer positioned at the N-phenyl group were synthesized using a reaction scheme that was slightly modified from Scheme 11-C above as illustrated in Scheme 11-D below:

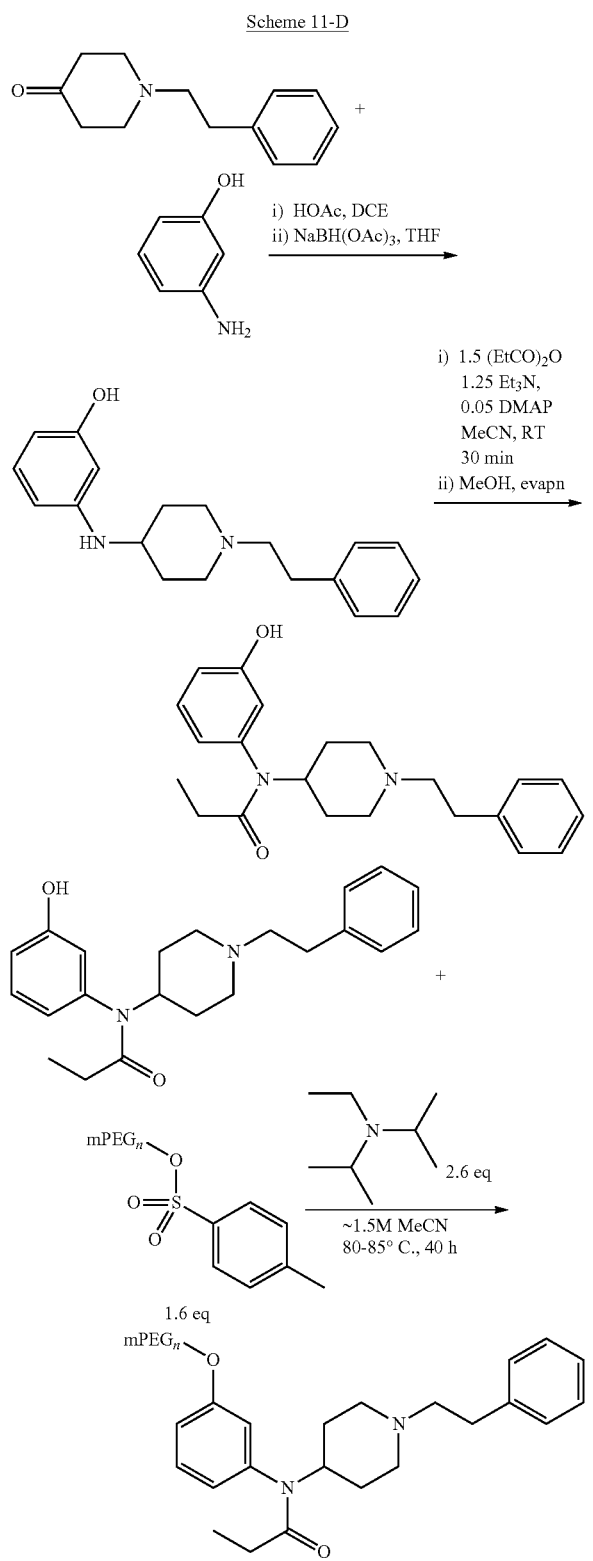

As indicated in Scheme 11-D above, the desired mPEG$_n$-O-fentanyl conjugates were prepared by first reacting 1-phenethylpiperidin-4-one with 3-aminophenol under reducing conditions to thereby convert the keto functionality into an amine, i.e., by reaction with the amino group of 3-aminophenol. The product, 3-(1-phenethylpiperidin-4-ylamino)phenol, was then reacted with propionic anhydride in the presence of base (e.g., triethyl amine) and dimethylaminopyridine (DMAP) under conditions effective to form N-(3-hydroxyphenyl)-N-(1-phenethylpiperidin-4-yl)propionamide. Finally, introduction of the oligomeric PEG functionality was carried out by reacting the precursor, N-(3-hydroxyphenyl)-N-(1-phenethylpiperidin-4-yl)propionamide, with a molar excess of mPEG$_{oligo}$tosylate under coupling conditions effective to form the desired conjugates. Ratios of reactants and reaction conditions generally employed are provided in the reaction schemes above.

Example 11A

Preparation of m-mPEG$_n$-O-Fentanyl Conjugates

Synthesis of m-mPEG$_1$-O-Fentanyl Conjugate
(n=1)

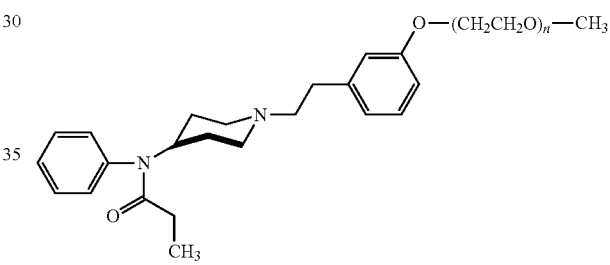

Using an approach set forth in Example 11 and as described schematically in Scheme 11-B, the above conjugate was prepared.

Synthesis of m-mPEG$_2$-O-Fentanyl Conjugate
(n=2)

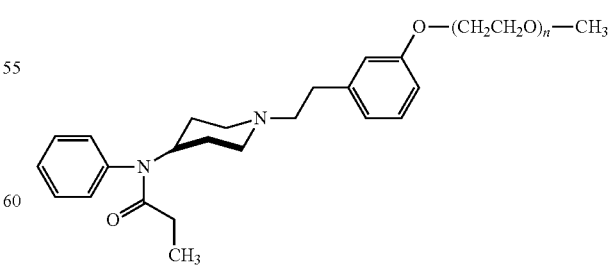

Using an approach set forth in Example 11 and as described schematically in Scheme 11-B, the above conjugate was prepared.

Synthesis of m-mPEG$_3$-O-Fentanyl Conjugate
(n=3)

Synthesis of m-mPEG$_6$-O-Fentanyl Conjugate
(n=6)

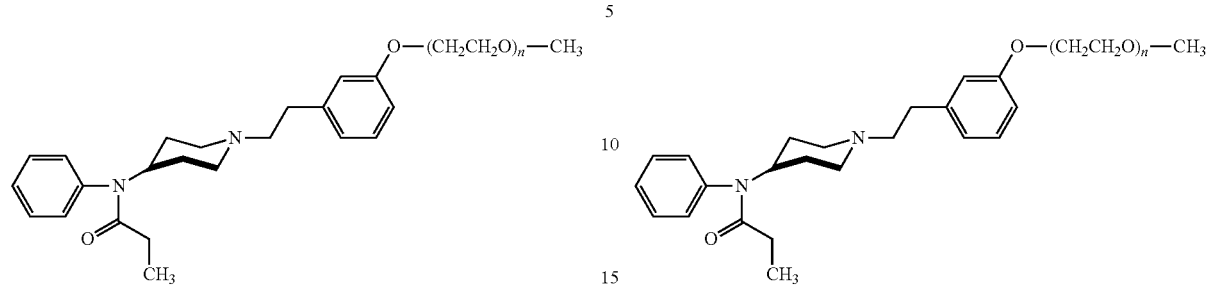

Using an approach set forth in Example 11 and as described schematically in Scheme 11-B, the above conjugate was prepared.

Using an approach set forth in Example 11 and as described schematically in Scheme 11-B, the above conjugate was prepared.

Synthesis of m-mPEG$_4$-O-Fentanyl Conjugate
(n=4)

Synthesis of m-mPEG$_7$-O-Fentanyl Conjugate
(n=7)

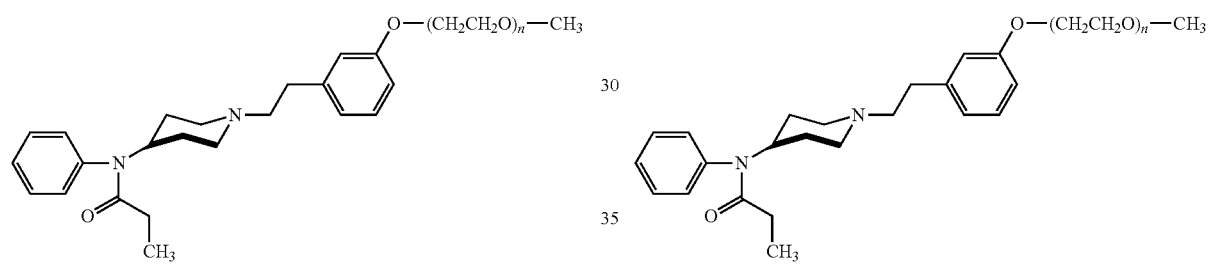

Using an approach set forth in Example 11 and as described schematically in Scheme 11-B, the above conjugate was prepared.

Using an approach set forth in Example 11 and as described schematically in Scheme 11-B, the above conjugate was prepared.

Synthesis of m-mPEG$_5$-O-Fentanyl Conjugate
(n=5)

Synthesis of m-mPEG$_7$-O-Fentanyl Conjugate
(n=7)

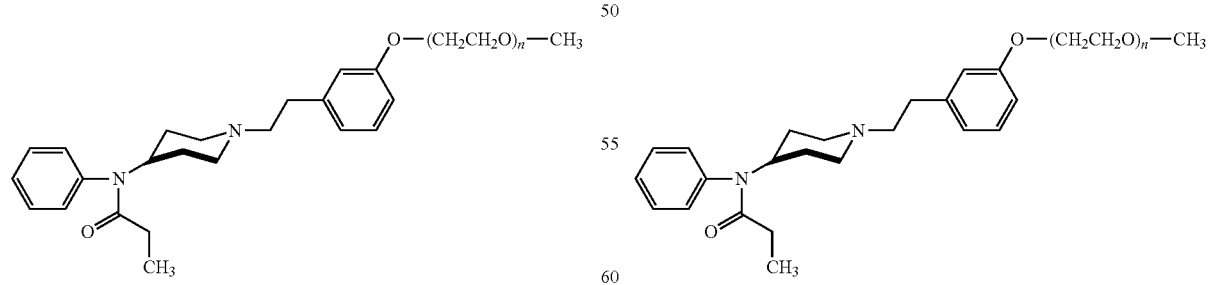

Using an approach set forth in Example 11 and as described schematically in Scheme 11-B, the above conjugate was prepared.

Using a similar approach set forth in Example 11 and as described schematically in Scheme 11-B, the above conjugate was prepared.

Synthesis of m-mPEG$_8$-O-Fentanyl Conjugate
(n=8)

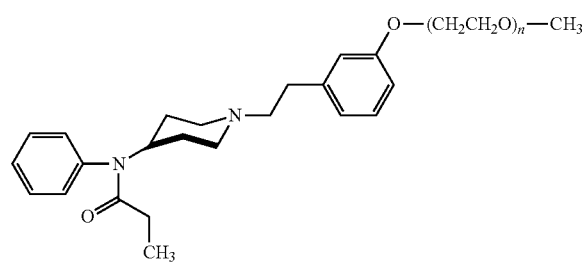

Using an approach set forth in Example 11 and as described schematically in Scheme 11-B, the above conjugate was prepared.

Synthesis of m-mPEG$_9$-O-Fentanyl Conjugate
(n=9)

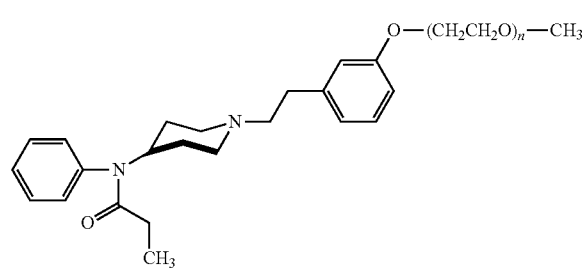

Using an approach set forth in Example 11 and as described schematically in Scheme 11-B, the above conjugate was prepared.

Each of the above mPEG$_{1-9}$-O-fentanyl conjugates was characterized by $^1$H NMR (200 MHz Bruker) and by LC/MS.

Example 12

Preparation of m-mPEG$_n$-O'-Fentanyl Conjugates

Synthesis of m-mPEG$_1$-O'-Fentanyl Conjugate
(n=1)

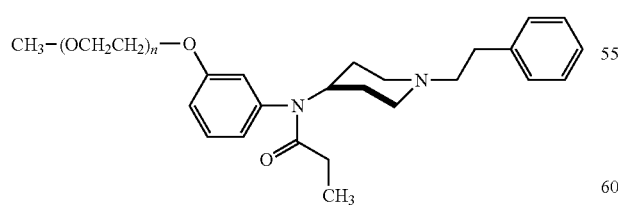

Using an approach set forth in Example 11 and as described schematically in Scheme 11-D, the above conjugate was prepared. In this series, the oligomeric mPEG was covalently attached at the meta-position of the N-phenyl group Synthesis of m-mPEG$_2$-O'-Fentanyl Conjugate
(n=2)

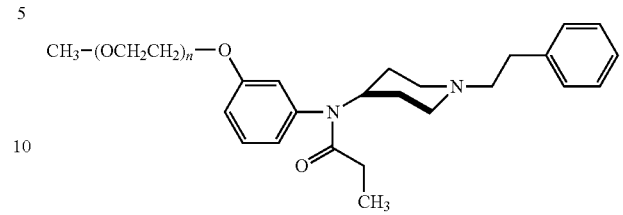

The above conjugate was prepared using the approach set forth in Example 11 and as described schematically in Scheme 11-D.

Synthesis of m-mPEG$_3$-O'-Fentanyl Conjugate
(n=3)

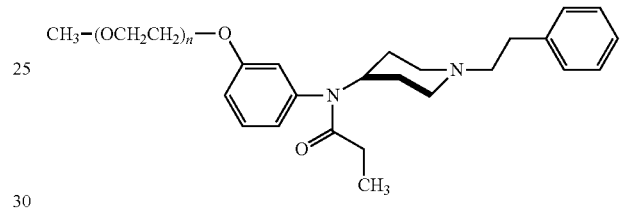

The above conjugate was prepared using the approach set forth in Example 11 and as described schematically in Scheme 11-D.

Synthesis of m-mPEG$_4$-O'-Fentanyl Conjugate
(n=4)

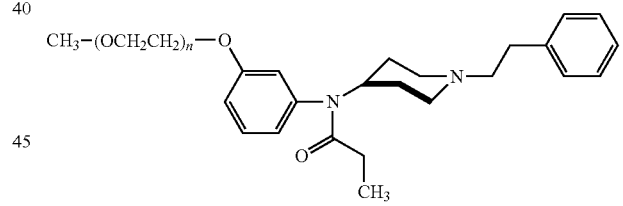

The above conjugate was prepared using the approach set forth in Example 11 and as described schematically in Scheme 11-D.

Synthesis of m-mPEG$_5$-O'-Fentanyl Conjugate
(n=5)

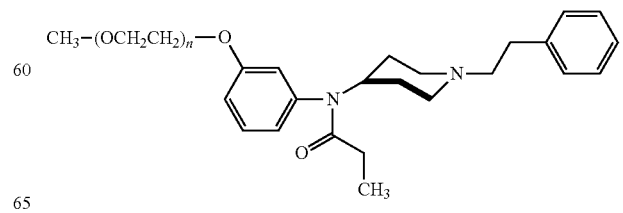

The above conjugate was prepared.

Synthesis of m-mPEG$_6$-O'-Fentanyl Conjugate
(n=6)

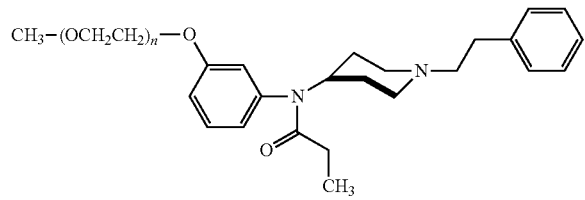

The above conjugate was prepared using the approach set forth in Example 11 and as described schematically in Scheme 11-D.

Synthesis of m-mPEG$_7$-O'-Fentanyl Conjugate
(n=7)

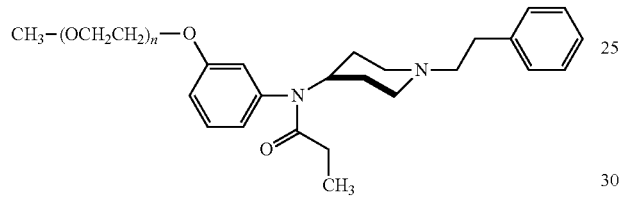

The above conjugate was prepared using the approach set forth in Example 11 and as described schematically in Scheme 11-D.

Synthesis of m-mPEG$_8$-O'-Fentanyl Conjugate
(n=8)

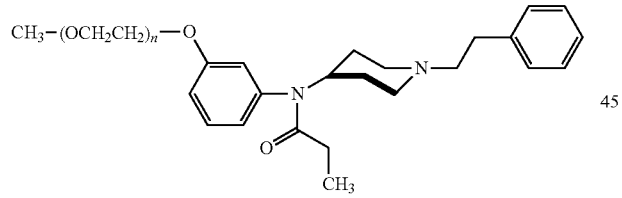

The above conjugate was prepared using the approach set forth in Example 11 and as described schematically in Scheme 11-D.

Synthesis of m-mPEG$_8$-O'-Fentanyl Conjugate
(n=8)

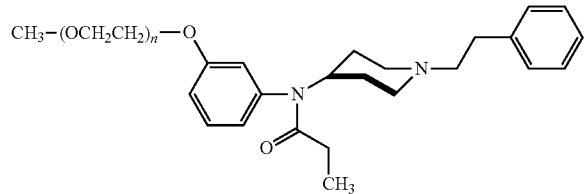

The above conjugate was prepared using the approach set forth in Example 11 and as described schematically in Scheme 11-D.

Synthesis of m-mPEG$_9$-O'-Fentanyl Conjugate
(n=9)

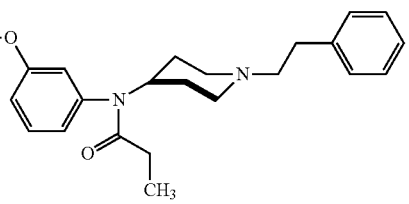

The above conjugate was prepared using the approach set forth in Example 11 and as described schematically in Scheme 11-D.

Each of the above mPEG$_{1-9}$-O'-fentanyl conjugates was characterized by $^1$H NMR (200 MHz Bruker) and by LC/MS.

Example 13

Preparation of para-mPEG$_n$-O'-Fentanyl Conjugates

Synthesis of p-mPEG$_1$-O'-Fentanyl Conjugate (n=1)

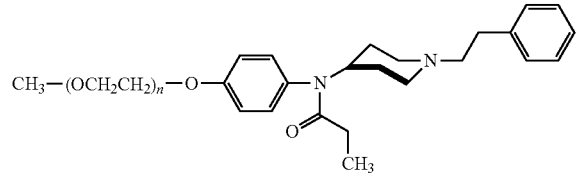

The above conjugate can be prepared using an approach set forth in Example 11. In this series, the oligomeric mPEG is covalently attached at the para-position of the N-phenyl group.

Synthesis of p-mPEG$_4$-O'-Fentanyl Conjugate (n=4)

The para-substituted conjugate was prepared according to the reaction scheme shown below:

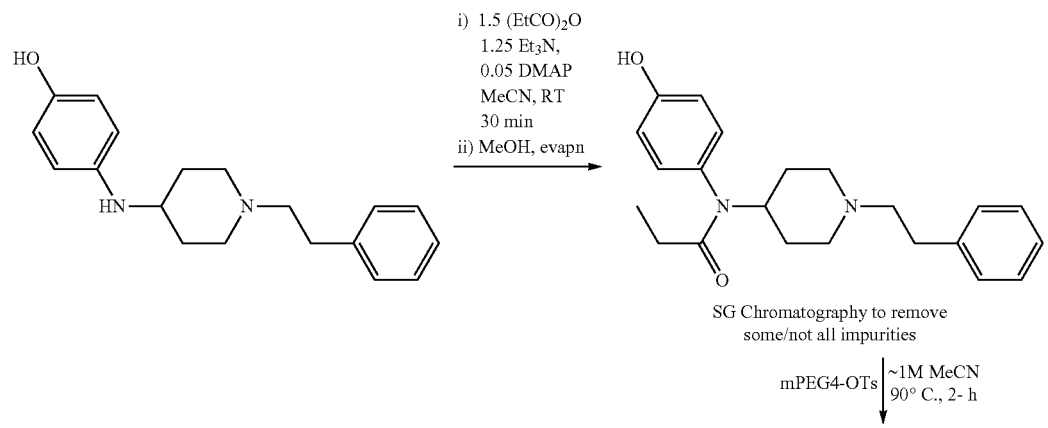

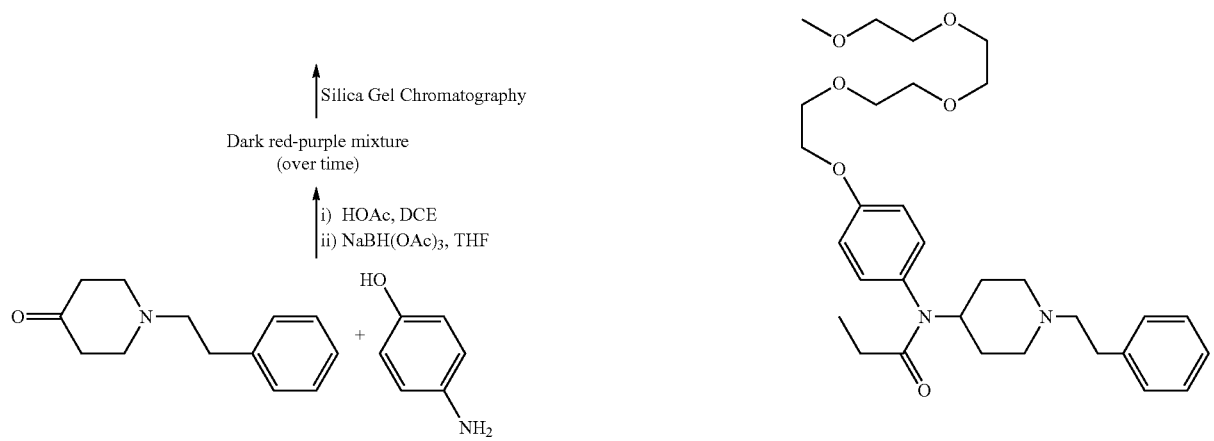

The desired pPEG₄-O-fentanyl conjugate was prepared by first reacting 1-phenethylpiperidin-4-one with 4-aminophenol under reducing conditions (e.g., in the presence of a reducing agent such as NaBH(OAc)₃) to thereby convert the keto functionality into an amine, i.e., by reaction with the amino group of 4-aminophenol. The product, 4-(1-phenethylpiperidin-4-ylamino)phenol, was then reacted with propionic anhydride in the presence of base (e.g., triethyl amine) and dimethylaminopyridine (DMAP) under conditions effective to form N-(4-hydroxyphenyl)-N-(1-phenethylpiperidin-4-yl)propionamide. Finally, introduction of the oligomeric PEG functionality was carried out by reacting the precursor, N-(4-hydroxyphenyl)-N-(1-phenethylpiperidin-4-yl)propionamide, with a mPEG₄tosylate under coupling conditions effective to form the desired conjugate. Ratios of reactants and reaction conditions generally employed are provided in the reaction scheme above.

Additional pPEG$_{oligo}$-O-fentanyl conjugates may be similarly prepared.

Example 14

Preparation of mPEG$_n$-OMs (mPEGn-O-Mesylate) for Use in Examples 15, 16 and 17

In a 40-mL glass vial was mixed HO—CH₂CH₂OCH₂CH₂—OH (1.2 ml, 10 mmol) and DIEA (N,N-diisopropylethylamine, 5.2 ml, 30 mmol, 3 eq), the resulting homogeneous colorless mixture was cooled to 0° C. and MsCl (1.55 ml, 20 mmol, 2 eq) was added via syringe slowly, over 4 minutes, with vigorous stirring. A biphasic mixture resulted upon addition: yellow solid on the bottom and clear supernatant. The ice bath was removed and the reaction was allowed to warm to room temperature overnight. At this point it was dissolved in water, extracted with CHCl₃ (3×50 mL), washed with 0.1M HCl/brine mixture 2×50 mL, followed by brine 50 mL. The organic layer was dried over MgSO₄, filtered to give a yellow solution and evaporated to give brown oil (2.14 g). ¹H NMR confirms product identity 3.3 (1H NMR δ 3.1 (s, 3H), 3.3 (s, 3H), 3.5-3.55 (m, 2H), 3.6-3.65 (m, 2H), 3.7-3.75 (m, 2H), 4.3-4.35 (m, 2H) ppm).

All other PEG$_n$-OMs's (n=3, 4, 5, 6, 7 and 9) were made in similar fashion and afforded final compounds in each case that were isolated as brown oils. Mass spectral and proton NMR data (not shown) confirmed the formation of the desired OMs PEGylated products.

Example 15

Preparation of mPEG$_n$-O-Morphine Conjugates

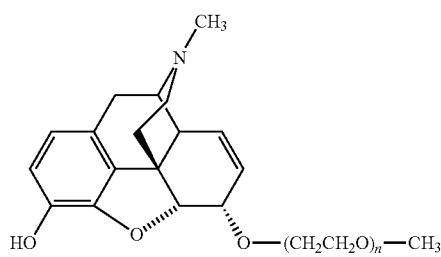

The following describes the preparation of free base using commercially available morphine sulfate hydrate (generally procedure).

Morphine sulfate USP from Spectrum (510 mg) was dissolved in water (70 ml). The solution was then basified to pH 10 using aqueous K$_2$CO$_3$ to give a white suspension. To the white suspension DCM (dichloromethane, 50 ml) was added, but failed to dissolve the solid. The mixture was made acidic with 1M HCl to result in clear biphasic solution. The organic phase was split off and the aqueous phase was carefully brought to pH 9.30 (monitored by a pH meter) using the same solution of K$_2$CO$_3$ as above. A white suspension resulted again. The heterogeneous mixture was extracted with DCM (5×25 ml) and an insoluble white solid contaminated both the organic and aqueous layers. The organic layer was dried with MgSO$_4$, filtered and rotary evaporated to yield 160 mg of morphine free base (56% recovery). No additional product was recovered from the filter cake using MeOH, but another 100 mg was recovered from the aqueous phase by 2×50 ml extraction with EtOAc to give a combined yield of 260 mg (68%).

MEM Protection of Morphine Free Base

The general approach for protecting the free base of morphine with the protecting group β-methoxyethoxymethyl ester ("MEM") is schematically shown below.

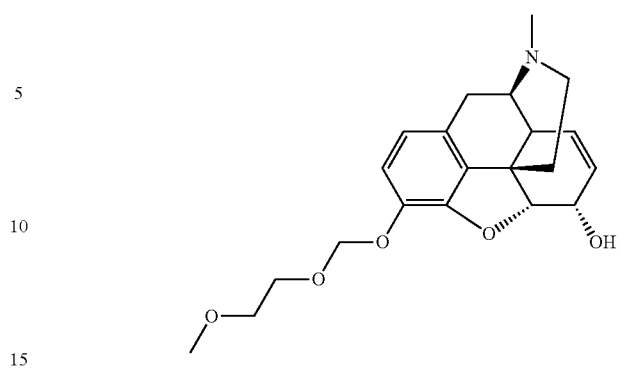

Free base morphine (160 mg, 0.56 mmol) was dissolved in 20 ml of Acetone/Toluene (2/1 mixture). To the resulting solution was added K$_2$CO$_3$ (209 mg, 1.51 mmol, 2.7 eq) followed by MEMCl (96 µl, 0.84 mmol, 1.5 eq) and the resulting heterogeneous mixture was stirred overnight at room temperature. After five hours at room temperature, the reaction was deemed complete by LC-MS. Morphine free base retention time under standard six minute gradient run conditions (std 6 min, Onyx Monolyth C18 column, 50×4.6 mm; 0 to 100% Acetonitrile 0.1% TFA in Water 0.1% TFA, 1.5 ml/min; detection: UV254, ELSD, MS; retention times are quoted for UV254 detector, ELSD has about 0.09 min delay and MS has about 0.04 min delay relative to UV) was 1.09 min; retention time for product 1.54 min (std 6 min), major impurity 1.79 min. The reaction mixture was evaporated to dryness, dissolved in water, extracted with EtOAc (3×, combined organic layer washed with brine, dried over MgSO$_4$, filtered and rotary evaporated) to give 160 mg (77%) of the desired product as a colorless oil. Product purity was estimated to be about 80% by UV254.

Direct MEM Protection of Morphine Sulfate (General Procedure)

The general approach for protecting morphine sulfate with the protecting group β-methoxyethoxymethyl ester ("MEM") is schematically shown below. Although not explicitly shown in the scheme below, morphine is actually morphine sulfate hydrate, morphine.0.5 H$_2$SO$_4$0.2.5 H$_2$O.

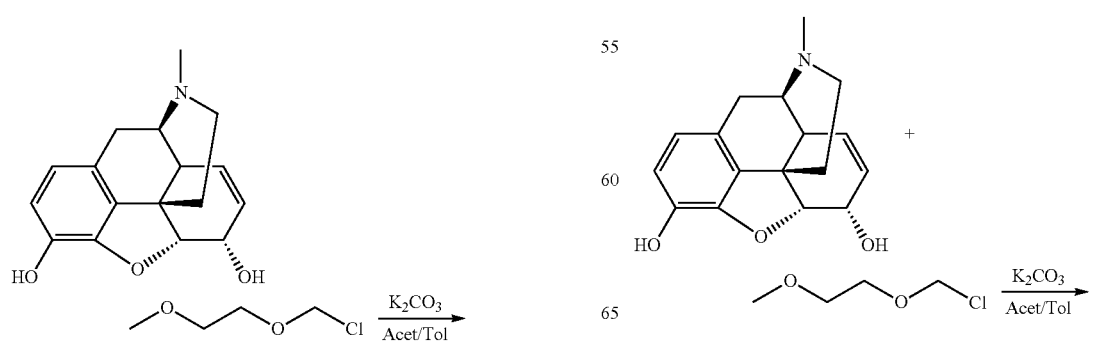

-continued

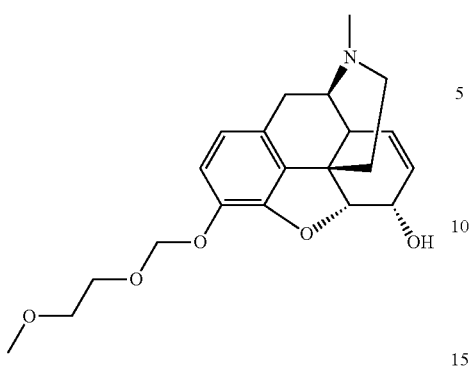

To a suspension of 103 mg of morphine sulfate hydrate (0.26 mmol) in 10 ml of 2:1 acetone:toluene solvent mixture was added 135 mg (1 mmol, 3.7 eq) of $K_2CO_3$ and the suspension stirred at room temperature for 25 minutes. To the resulting suspension was added 60 μl (0.52 mmol) of MEMCl and the mixture allowed to react at room temperature. It was sampled after one hour (38% nominal conversion, additional peaks at 1.69 min and 2.28 min), three hours (40% nominal conversion, additional peak at 1.72 min (M+1=493.2)), four and one-half hours (56% nominal conversion, additional peak at 1.73 min), and twenty-three hours (>99% nominal conversion, additional peak at 1.79 min—about 23% of the product peak by height in $UV_{254}$); thereafter, the reaction was quenched with MeOH, evaporated, extracted with EtOAc to give 160 mg of clear oil.

The same reaction was repeated starting with 2 g (5.3 mmol) of morphine sulfate hydrate, 2.2 g (16 mmol, 3 eq) of $K_2CO_3$, 1.2 ml (10.5 mmol, 2 eq) of MEMCl in 100 ml of solvent mixture. Sampling occurred after two hours (61% nominal conversion, extra peak at 1.72 min (M+1=492.8)), after one day (80% nominal conversion, extra peak at 1.73 min), after three days (85% nominal conversion, only small impurities, 12 min gradient run), and after six days (91% conversion); thereafter, the reaction was quenched, evaporated, extracted with EtOAc, purified on combi-flash using a 40 g column, DCM:MeOH 0 to 30% mobile phase. Three peaks (instead of two) were identified, wherein the middle peak was collected, 1.15 g (58% yield) of light yellow oil, $UV_{254}$ purity about 87%.

Conjugation of MEM-Protected Morphine to Provide a MEM-Protected Morphine Conjugate The general approach for conjugating MEM-protected morphine with a water-soluble oligomer to provide a MEM-protected morphine PEG-oligomer conjugate is schematically shown below.

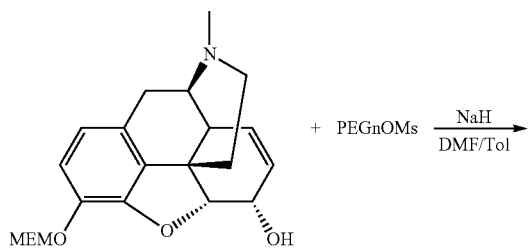

-continued

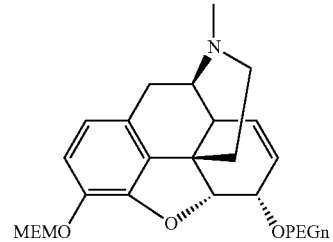

To a solution of toluene/DMF (2:1 mixture, 10 volumes total) was charged MEM-morphine free base followed by NaH (4-6 eq) and then $PEG_nOMs$ (1.2-1.4 eq.), previously prepared. The reaction mixture was heated to 55-75° C. and was stirred until reaction completion was confirmed by LC-MS analysis (12-40 hours depending on PEG chain length). The reaction mixture was quenched with methanol (5 volumes) and the reaction mixture was evaporated to dryness in vacuo. The residue was redissolved in methanol (3 volumes) and was chromatographed using a Combiflash system (0-40% MeOH/DCM). The fractions containing large amounts of product were collected, combined and evaporated to dryness. This material was then purified by RP-HPLC to give the products as yellow to orange oils.

Deprotection of MEM-Protected Morphine Conjugate to Provide a Morphine Conjugate The general approach for deprotecting a MEM-protected morphine conjugate to provide a morphine conjugate is schematically shown below.

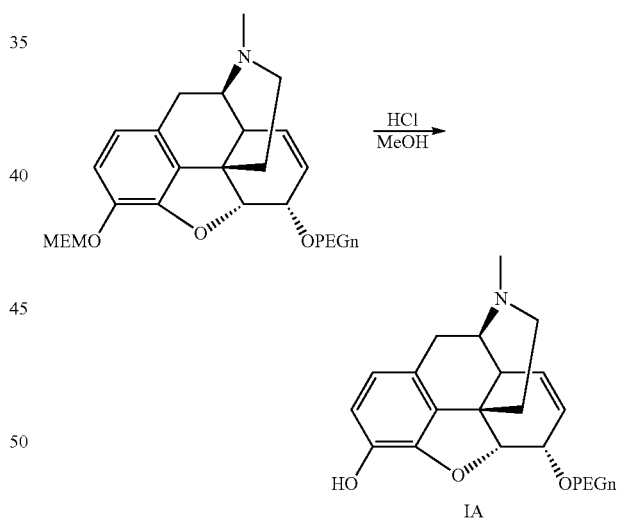

To a solution of MEM-protected morphine conjugate TFA salt suspended in DCM (8 volumes) was charged 6 volumes of 2M HCl in diethyl ether. The reaction mixture was allowed to stir at room temperature for two hours and was then evaporated to dryness under reduced pressure. The oily residue was dissolved in MeOH (8 volumes), filtered through glass wool and then evaporated under reduced pressure to give a thick orange to yellow oil in quantitative yield. Compounds made by this method include: α-6-$mPEG_3$-O-morphine (Compound A, n=3) 217 mg of HCl salt 97% pure (95% by UV254; 98% by ELSD); α-6-$mPEG_4$-O-morphine (Compound A, n=4) 275 mg of HCl salt 98% pure (97% by UV254; 98% by ELSD); α-6- mPEG$_5$-O-morphine (Compound A, n=5) 177 mg of HCl salt 95% pure (93% by UV254; 98% by ELSD); α-6-mPEG$_6$-O-morphine (Compound A, n=6) 310 mg of HCl salt 98% pure (98% by UV254; 99% by ELSD); α-6-mPEG$_7$-O-morphine (Compound A, n=7) 541 mg of HCl salt 96% pure (93% by UV254; 99% by ELSD); and α-6-mPEG-O$_9$-morphine (Compound A, n=9) 466 mg of HCl salt 98% pure (97% by UV254; 99% by ELSD). Additionally, morphine conjugates having a single PEG monomer attached, α-6-mPEG$_1$-O-morphine (Compound A, n=1), 124 mg of HCl salt, 97% pure (95% pure by UV$_{254}$; 98% by ELSD); as well as α-6-mPEG$_2$-O-morphine (Compound A, n=2), 485 mg of HCl salt, 97% pure (95% pure by UV$_{254}$; 98% by ELSD) were similarly prepared.

Example 16

Preparation of mPEG$_n$-O-Codeine Conjugates

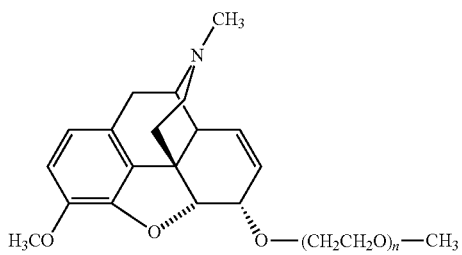

The general approach for conjugating codeine with an activated sulfonate ester of a water-soluble oligomer (using mPEG$_3$OMs as a representative oligomer) to provide a codeine conjugate is schematically shown below.

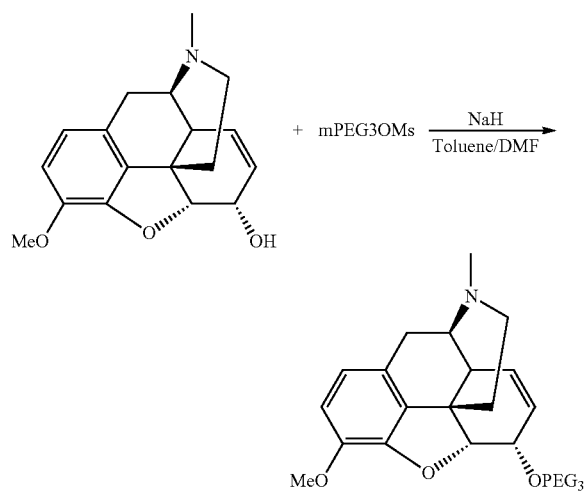

Codeine (30 mg, 0.1 mmol) was dissolved in toluene/DMF (75:1) solvent mixture followed by addition of HO—CH$_2$CH$_2$OCH$_2$CH$_2$OCH$_2$CH$_2$OMs (44 ml, 2 eq) and NaH (60% suspension in mineral oil, 24 mg, 6 eq). The resulting homogeneous yellow solution was heated to 45° C. After one hour, the reaction showed 11% conversion (extra peak at 2.71 min, 12 min run), after eighteen hours, the reaction showed 7% conversion (extra peak at 3.30 min, 12 min run), and after 24 hours, the reaction showed 24% conversion (multitude of extra peaks, two tallest ones are 1.11 min and 2.79 min). At this point, an additional 16 mg of NaH was added and heating continued for six hours, after which, an additional 16 mg of NaH was added followed by continued heating over sixty-six hours. Thereafter, no starting material remained, and analysis revealed many extra peaks, the two tallest ones corresponding to 2.79 min and 3 min (product peak is the second tallest among at least 7 peaks).

This synthesis was repeated using 10× scale wherein 30 ml of solvent mixture was used. After eighteen hours, analysis revealed 71% nominal conversion with additional peaks in the UV (one tall peak at 3.17 min and many small ones; wherein the desired peak corresponded to 3.43 min in UV). Thereafter, 80 mg (2 mmol) of NaH was added followed by continued heating. After three hours, analysis revealed 85% nominal conversion (several extra peaks, main 3.17 min). Reaction mixture was diluted with water, extracted with EtOAc (3×, combined organic layer washed with brine, dried over MgSO$_4$, filtered and rotary evaporated) to give yellow oil (no sm in LC-MS, 90% pure by ELSD, 50% pure by UV-major impurity at 3.2 min). The crude product was dissolved in DCM, applied to a small cartridge filled with 230-400 mesh SiO$_2$, dried, eluted on a Combi-flash via a 4 g pre-packed column cartridge with solvent A=DCM and solvent B=MeOH, gradient 0 to 30% of B. Analysis revealed two peaks of poor symmetry: a small leading peak and a larger peak with a tail. LC-MS was used to analyze fractions, wherein none were identified as containing pure product. Combined fractions that contained any product (tt#22-30) yielded, following solvent evaporation, 150 mg (34% yield) of impure product (LC-MS purity at 3.35 min by UV254, wherein about 25% represented the main impurities 3.11 min, 3.92 min, 4.32 min, 5.61 min of a 12 min run). A second purification by HPLC (solvent A=water, 0.1% TFA; solvent B=acetonitrile, 0.1% TFA) employing a gradient corresponding to 15-60% B, 70 min, 10 ml/min) resulted in poor separation from adjacent peaks. Only two fractions were clean enough and gave 21 mg of TFA salt (>95% pure, 4.7% yield). Three additional fractions both before and after the desired product-containing fractions (for a total of six additional fractions were combined to give 70 mg of about 50% pure product as TFA salts.

Using this same approach, other conjugates differing by the number of ethylene oxide units (n=4, 5, 6, 7, and 9) were made using these NaH conditions outlined above.

Conversion of Codeine-Oligomer Conjugate TFA Salts to Codeine-Oligomer HCl Salts.

The general approach for converting codeine-oligomer TFA salts to codeine-oligomer HCl salts is schematically shown below.

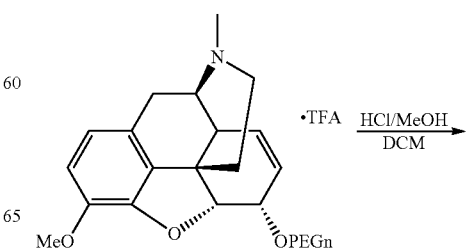

85
-continued

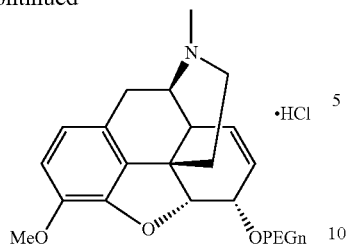

·HCl

MeO     OPEGn

To a solution of codeine-oligomer conjugate TFA salt suspended in DCM (8 volumes) was charged 6 volumes of 2M HCl in diethyl ether. The reaction mixture was allowed to stir at room temperature for two hours and was then evaporated to dryness under reduced pressure. The oily residue was dissolved in MeOH (8 volumes), filtered through glass wool and then evaporated under reduced pressure to give a thick orange to yellow oil in quantitative yield. Following this general procedure, the following compounds were synthesized: α-6-mPEG$_3$-O-codeine (Compound B, n=3) 235 mg of HCl salt, 98% pure; α-6-mPEG$_4$-O-codeine (Compound B, n=4) 524 mg of HCl salt, 98% pure; α-6-mPEG$_5$-O-codeine (Compound B, n=5) 185 mg of HCl salt, 98% pure+119 mg of HCl salt 97% pure, α-6-mPEG$_6$-O-codeine (Compound B, n=6) 214 mg of HCl salt, 97% pure; α-6-mPEG$_7$-O-codeine (Compound B, n=7) 182 mg of HCl salt, 98% pure; α-6-mPEG$_9$-O-codeine (Compound B, n=9) 221 mg of HCl salt, 97% pure; α-6-mPEG$_1$-O-codeine (Compound B, n=1) 63 mg of HCl salt, 90% pure; and α-6-mPEG$_2$-O-codeine (Compound B, n=2) 178 mg of HCl salt, 90% pure.

Example 17

Preparation of mPEG$_n$-O-Hydroxycodone Conjugates

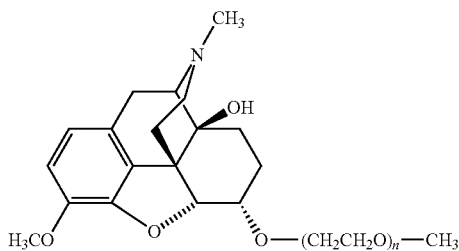

The general approach for conjugating hydroxycodone with an activated sulfonate ester of a water-soluble oligomer (using "mPEG$_n$OMs" as a representative oligomer) to provide a hydroxycodone conjugate is schematically shown below.

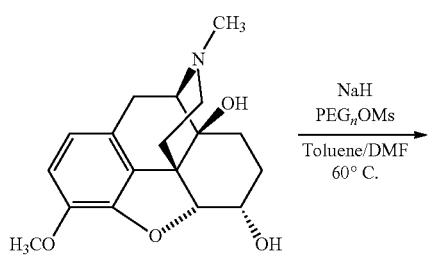

86
-continued

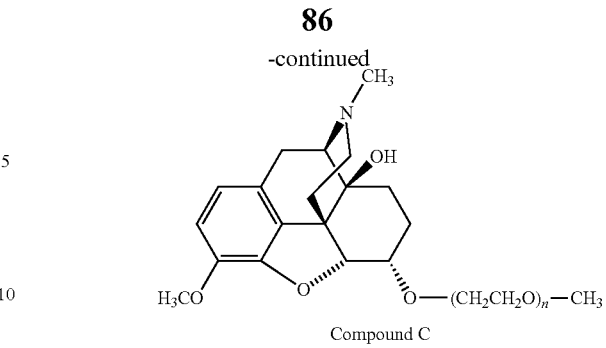

Compound C

Reduction of Oxycodone to α-6-hydroxycodone:

To a solution of oxycodone free base in dry THF under nitrogen cooled at −20° C., was added a 1.0 M THF solution of potassium tri-sec-butylborohydride over 15 minutes. The solution was stirred at −20° C. under nitrogen for 1.5 hours and then water (10 mL) was added slowly. The reaction mixture was stirred another 10 minutes at −20° C. and then allowed to warm to room temperature. All solvents were removed under reduced pressure and CH$_2$Cl$_2$ was added to the remaining residue. The CH$_2$Cl$_2$ phase was extracted with a 0.1 N HCl/NaCl water solution and the combined 0.1 N HCl solution extracts were washed with CH$_2$Cl$_2$, then Na$_2$CO$_3$ was added to adjust the pH=8. The solution was extracted with CH$_2$Cl$_2$. The CH$_2$Cl$_2$ extracts were dried over anhydrous Na$_2$SO$_4$. After removing the solvent under reduced pressure, the desired α-6-HO-3-hydroxycodone was obtained.

Conjugation of mPEG$_n$OMs to α-6-hydroxycodone:

To a solution of Toluene/DMF (2:1 mixture, 10 volumes total) was charged hydroxycodone (prepared as set forth in the preceding paragraph) followed by NaH (4 eq) and then mPEG$_n$OMs (1.3 e.). The reaction mixture was heated to 60-80° C. and was stirred until reaction completion was confirmed by LC-MS analysis (12-40 hours depending on PEG chain length). The reaction mixture was quenched with methanol (5 volumes) and the reaction mixture was evaporated to dryness in vacuo. The residue was re-dissolved in methanol (3 volumes) and was chromatographed using Combiflash (0-40% MeOH/DCM). The fractions containing large amounts of product were collected, combined and evaporated to dryness. This material was then purified by RP-HPLC to provide the final products as yellow to orange oils.

Conversion of Hydroxycodone Conjugate TFA Salts to Hydroxycodone Conjugate HCl Salts To a solution of hydroxycodone conjugate TFA salt suspended in DCM (8 volumes) was charged 6 volumes of 2M HCl in diethyl ether. The reaction mixture was allowed to stir at room temperature for two hours and was then evaporated to dryness under reduced pressure. The oily residue was dissolved in MeOH (8 volumes), filtered through glass wool and then evaporated under reduced pressure to give a thick orange to yellow oil in quantitative yield. Following this general procedure, the following compounds were synthesized: α-6-mPEG$_3$-O-oxycodone (aka α-6-mPEG$_3$-O-hydroxycodone) (Compound C, n=3) 242 mg of HCl salt, 96% pure; α-6-mPEG$_4$-O-oxycodone (aka α-6-mPEG$_4$-O-hydroxycodone) (Compound C, n=4) 776 mg of HCl salt, 94% pure; α-6-mPEG$_5$-O-oxycodone (aka α-6-mPEG$_5$-O-hydroxycodone) (Compound C, n=5) 172 mg of HCl salt, 93% pure; α-6-mPEG$_6$-O-oxycodone (aka α-6-mPEG$_6$-O-hydroxycodone) (Compound C, n=6) 557 mg of HCl salt, 98% pure; α-6-mPEG$_7$-O-oxycodone (aka α-6-mPEG$_7$-O- hydroxycodone) (Compound C, n=7) 695 mg of HCl salt, 94% pure; and α-6-mPEG$_9$-O-oxycodone (aka α-6-mPEG$_9$-O-hydroxycodone) (Compound C, n=9) 435 mg of HCl salt 95% pure. The following compounds, α-6-mPEG$_1$-O-oxycodone (aka α-6-mPEG$_1$-O-hydroxycodone) (Compound C, n=1) 431 mg of HCl salt 99% pure; and α-6-mPEG$_2$-O-oxycodone (aka α-6-mPEG$_2$-O-hydroxycodone) (Compound C, n=2) 454 mg HCl salt, 98% pure, were similarly prepared.

Example 18

In-Vivo Analgesic Assay: Phenylquinone Writhing

An analgesic assay was used to determine whether exemplary PEG-oligomer-opioid agonist conjugates belonging to the following conjugate series: mPEG$_{2-7,9}$-O-morphine, mPEG$_{3-7,9}$-O-codeine, and mPEG$_{1-4,6, 7, 9}$-O-hydroxycodone, are effective in reducing and/or preventing visceral pain in mice.

The assay utilized CD-1 male mice (5-8 mice per group), each mouse being approximately 0.020-0.030 kg on the study day. Mice were treated according to standard protocols. Mice were given a single "pretreatment" dose of a compound lacking covalent attachment of a water-soluble, non-peptidic oligomer (i.e., non-PEG oligomer-modified parent molecule), a corresponding version comprising the compound covalently attached to a water-soluble, non-peptidic oligomer (i.e., the conjugate), or control solution (IV, SC, IP or orally) thirty minutes prior to the administration of the phenylquinone (PQ) solution. Each animal was given an IP injection of an irritant (phenylquinone, PQ) that induces "writhing" which may include: contractions of the abdomen, twisting and turning of the trunk, arching of the back, and the extension of the hindlimbs. Each animal was given an IP injection of PQ (1 mg/kg PQ, 0.1 mL/10 g bodyweight). After the injection, the animals were returned to their observation enclosure and their behavior was observed. Contractions were counted between 35 and 45 minutes after the 'pretreatment". The animals were used once. Each tested article was dosed at a range between 0.1 and 100 mg/kg (n=5-10 animals/dose).

Figure 4:
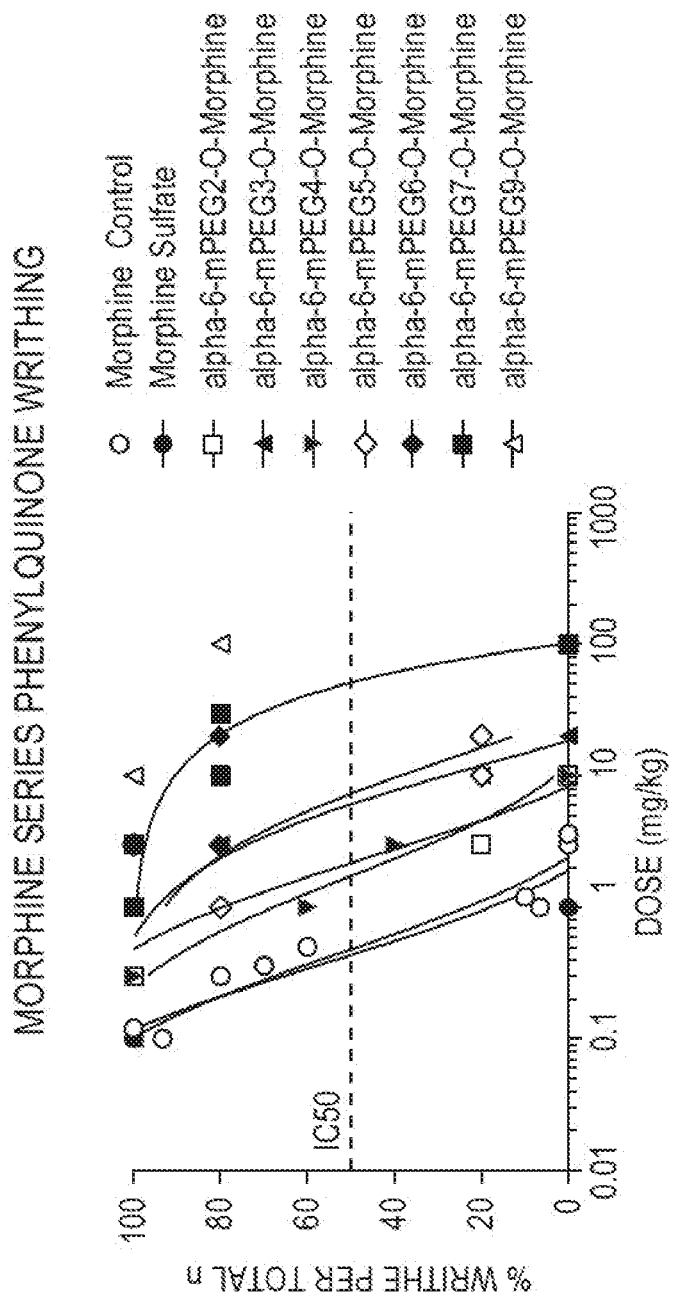
FIG. 4 is a graph showing percent writhing per total number of mice, n, in the study group, versus dose of mPEG$_n$-O-morphine conjugate administered in an analgesic assay for evaluating the extent of reduction or prevention of visceral pain in mice as described in detail in Example 18. Morphine was used as a control; unconjugated parent molecule, morphine sulfate, was also administered to provide an additional point of reference. Conjugates belonging to the following conjugate series: mPEG$_{2-7,9}$-O-morphine were evaluated.
Figure 5:
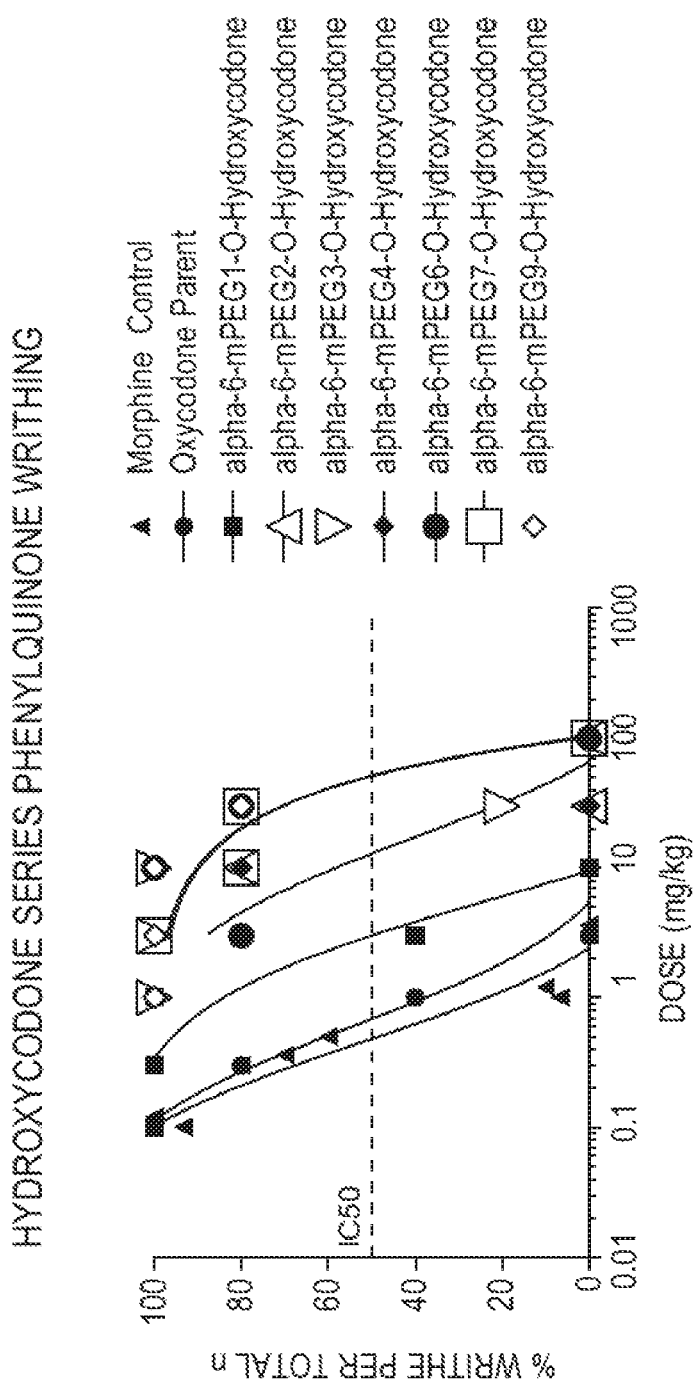
FIG. 5 is a graph showing percent writhing per total number of mice, n, in the study group, versus dose of mPEG$_n$-O-hydroxycodone conjugate administered in an analgesic assay for evaluating the extent of reduction or prevention of visceral pain in mice as described in detail in Example 18. Morphine was used as a control; unconjugated parent molecule, oxycodone, was also administered to provide an additional point of reference. Conjugates belonging to the following conjugate series: mPEG$_{1-4, 6, 7, 9}$-O-hydroxycodone were evaluated.
Figure 6:
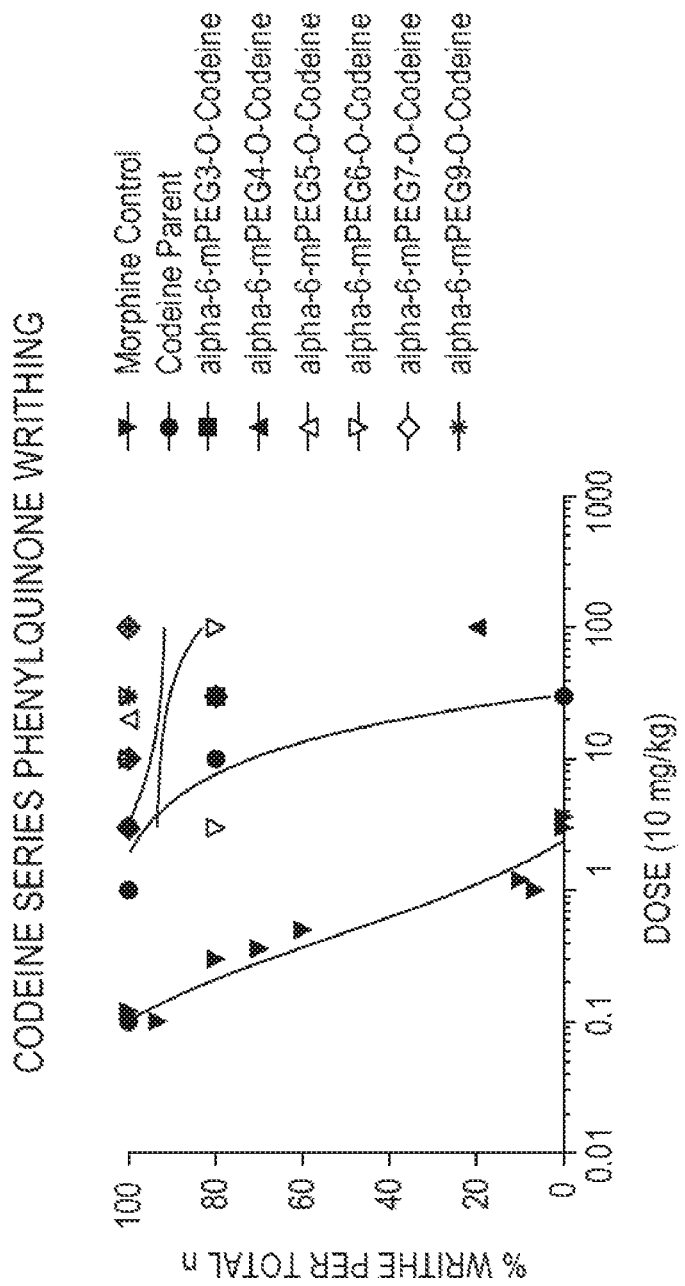
FIG. 6 is a graph showing percent writhing per total number of mice, n, in the study group, versus dose of mPEG$_n$-O-codeine conjugate administered in an analgesic assay for evaluating the extent of reduction or prevention of visceral pain in mice as described in detail in Example 18. Morphine was used as a control; unconjugated parent molecule, codeine, was also administered to provide an additional point of reference. Conjugates belonging to the following conjugate series: mPEG$_{3-7, 9}$-O-codeine were evaluated.

The results are shown in FIG. 4 (mPEG$_{2-7,9}$-O-morphine and control), FIG. 5 (mPEG$_{1-4,6, 7, 9}$-O-hydroxycodone and control), and FIG. 6 (mPEG$_{3-7,9}$-O-codeine and control). ED50 values are provided in Tables 3A and 3B below.

Example 19

In-Vivo Analgesic Assay: Hot Plate Latency Assay

A hot plate latency analgesic assay was used to determine whether exemplary PEG-oligomer-opioid agonist conjugates belonging to the following conjugate series: mPEG$_{1-5}$-O-morphine, mPEG$_{1-5}$-O-hydroxycodone, and mPEG$_{2-5, 9}$-O-codeine, are effective in reducing and/or preventing visceral pain in mice.

The assay utilized CD-1 male mice (10 mice per group), each mouse being approximately 0.028-0.031 kg on the study day. Mice were treated according to standard protocols. Mice were given a single "pretreatment" dose of a compound lacking covalent attachment of a water-soluble, non-peptidic oligomer (unmodified parent molecule), a corresponding version comprising the compound covalently attached to a water-soluble, non-peptidic oligomer (i.e., the conjugate), or control solution (SC) thirty minutes prior to the hot plate test. The hot plate temperature was set at 55±1° C., calibrated with a surface thermometer before commencement of the experiment. Thirty minutes after "pretreatment", each mouse was placed on the hot plate, and latency to lick a hindpaw was recorded to the nearest 0.1 second. If no lick occurred within 30 seconds, the mouse was removed. Immediately after hot plate testing, a temperature probe was inserted 17 mm into the rectum, and body temperature was read to the nearest 0.1° C. when the meter stabilized (approximately 10 seconds). The animals were used once. Each tested article was dosed at a range between 0.3 and 30 mg/kg (n=5-10 animals/dose).

Figure 7:
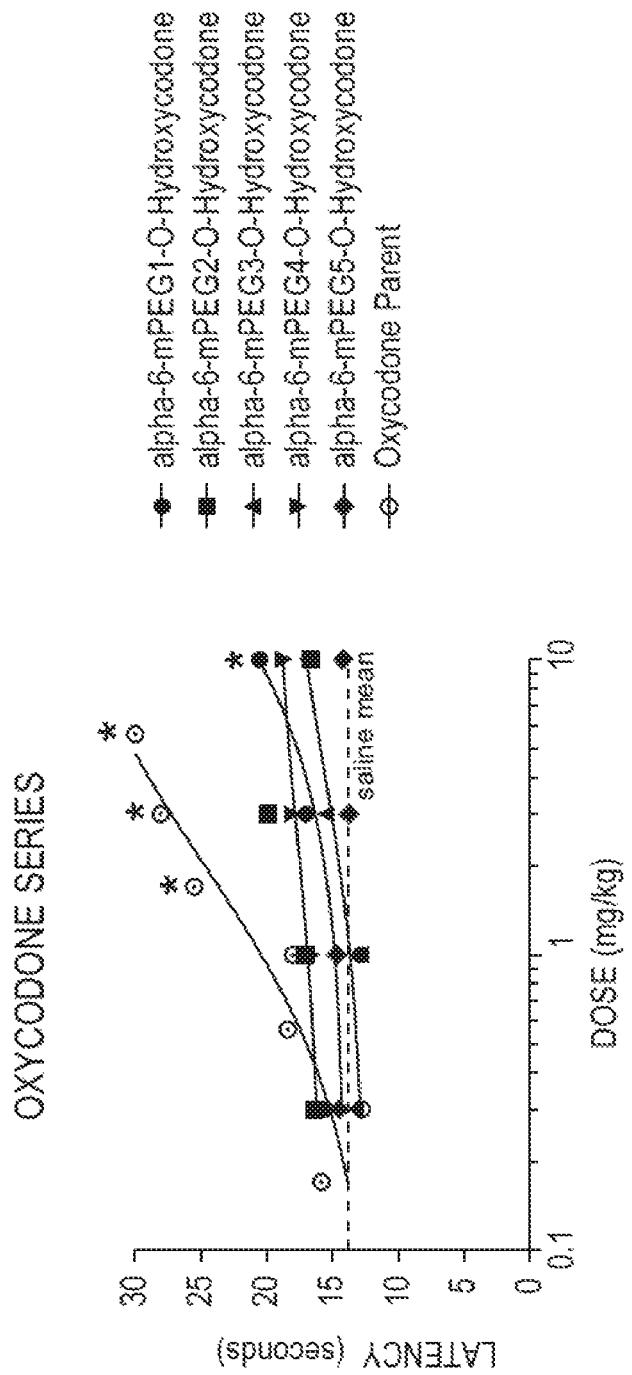
FIGS. 7-9 are plots indicating the results of a hot plate latency analgesic assay in mice as described in detail in Example 19. Specifically, the figures correspond to graphs showing latency (time to lick hindpaw), in seconds versus dose of compound.
Figure 8:
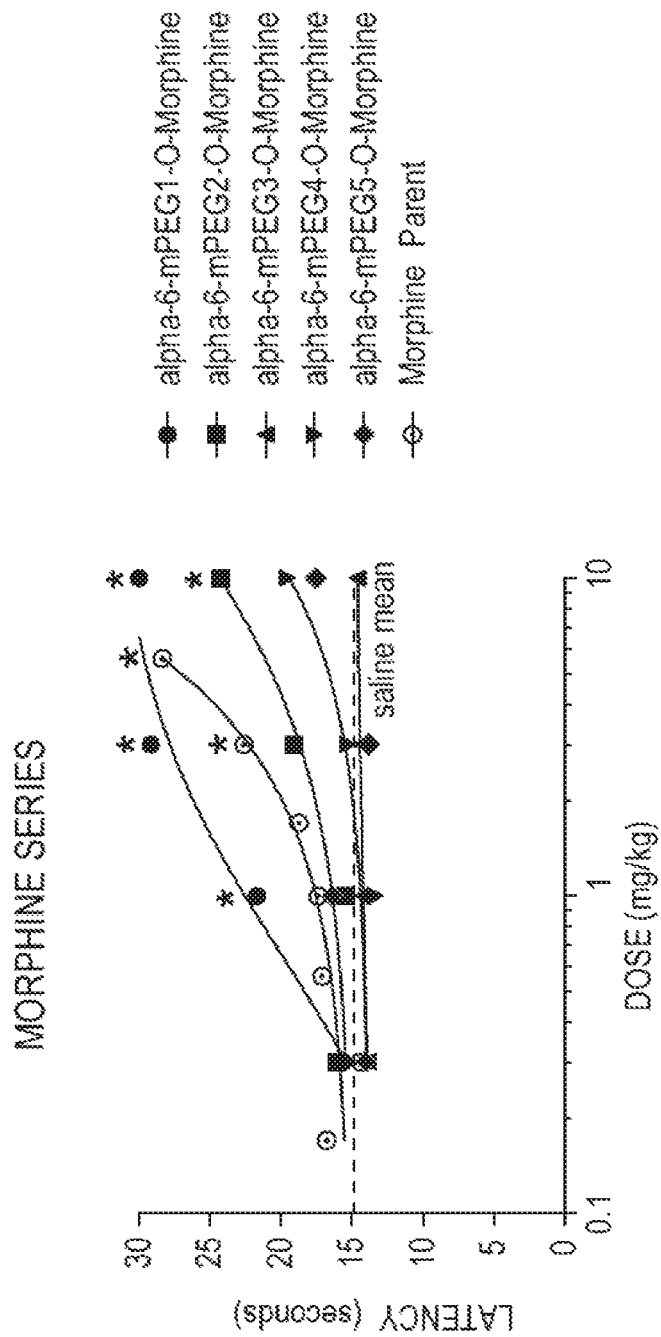
Figure 9:
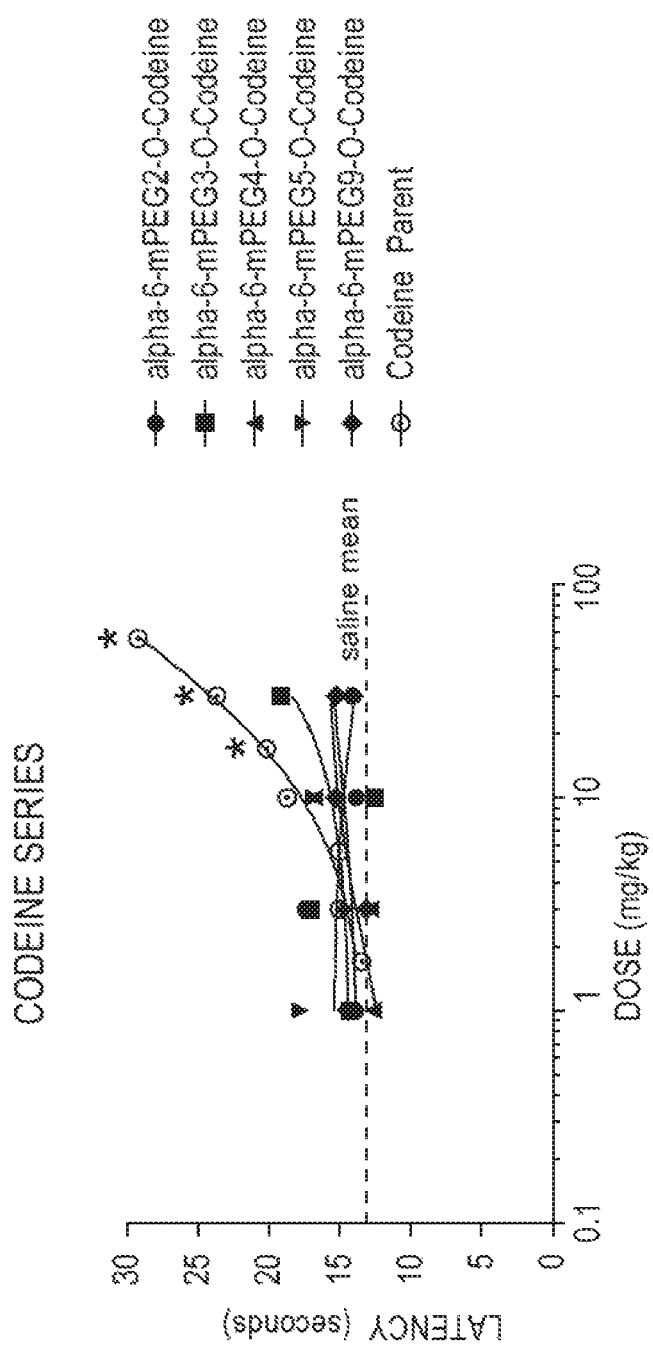

Results are shown in FIG. 7 (hydroxycodone series), FIG. 8 (morphine series) and FIG. 9 (codeine). Plots illustrate latency (time to lick hindpaw, in seconds) versus dose of compound administered in mg/kg.

Example 20

Pharmacokinetics of PEG$_{oligo}$-Opioid Compounds Following Intravenous (IV) and Oral (PO) Dosing in Male Sprague-Dawley Rats—Study Design One seventy five (175) adult male Sprague-Dawley rats with indwelling jugular vein and carotid artery catheters (JVC/CAC) (Charles River Labs, Hollister, Calif.) were utilized for the study. There were 3 rats/group. All animals were food fasted overnight. Prior to dosing the rats were weighed, the tails and cage cards were labeled for identification and the doses were calculated. Anesthesia was

TABLE 3A

ED$_{50}$ values for mPEG$_n$-O-Morphine Series

| | MORPHINE | PEG 2 | PEG 3 | PEG 4 | PEG 5 | PEG 6 | PEG 7 | PEG 9 |
|---|---|---|---|---|---|---|---|---|
| ED$_{50}$ (mg/kg) | 0.3693 | 2.512 | 13.58 | 3.281 | 13.4 | n/a | n/a | n/a |

TABLE 3B

ED$_{50}$ values for mPEG$_n$-O-HydroxyCodone Series

| | OXYCODONE | PEG 1 | PEG 2 | PEG 3 | PEG 4 | PEG 6 | PEG 7 | PEG 9 |
|---|---|---|---|---|---|---|---|---|
| ED$_{50}$ (mg/kg) | 0.6186 | 6.064 | n/a | n/a | 17.31 | n/a | n/a | n/a | induced and maintained with 3.0-5.0% isoflurane. The JVC and CAC were externalized, flushed with HEP/saline (10 IU/mL HEP/mL saline), plugged, and labeled to identify the jugular vein and carotid artery. The predose sample was collected from the JVC. When all of the animals had recovered from anesthesia and the predose samples were processed, the animals for intravenous group were dosed, intravenously (IV) via the JVC using a 1 mL syringe containing the appropriate test article, the dead volume of the catheter was flushed with 0.9% saline to ensure the animals received the correct dose and oral group animals were treated orally via gavage.

Following a single IV dose, blood samples were collected at 0 (pre-dose collected as described above), 2, 10, 30, 60, 90, 120, and 240 minutes and following oral dose, blood samples were collected 0 (pre-dose collected as described above), 15, 30, 60, 120, 240 and 480 minutes via the carotid artery catheter and processed as stated in the protocol. Following the last collection point, the animals were euthanized.

Bioanalytical analysis of the plasma samples was conducted using LC-MS/MS methods.

Pharmacokinetic Analyses:

PK analysis was performed using WinNonlin (Version 5.2, Mountain View, Calif.-94014). Concentrations in plasma that were below LLOQ were replaced with zeros prior to generating Tables and PK analysis. The following PK parameters were estimated using plasma concentration-time profile of each animal:

$C_0$ Extrapolated concentration to time "zero"
$C_{max}$ Maximum (peak) concentration
$AUC_{all}$ Area under the concentration-time from zero to time of last concentration value
$T_{1/2(z)}$ Terminal elimination half-life
$AUC_{inf}$ Area under the concentration-time from zero to time infinity
$T_{max}$ Time to reach maximum or peak concentration following administration
CL Total body clearance
$V_z$ Volume of distribution based on terminal phase
$V_{ss}$ Volume of distribution at steady state
$MRT_{last}$ Mean residence time to last observable concentration F Bioavailability Oral bioavailability was estimated using mean dose-normalized AUCall data for the compounds where one of IV or PO groups with only reported data for <n=3/group.

Example 21

IV and PO Pharmacokinetics of $mPEG_n$-O-Hydroxycodone Conjugates

A pharmacokinetic study was conducted in Sprague-Dawley rats as described in Example 20 above. Compounds administered were $mPEG_n$-O-hydroxycodone conjugates where n=1, 2, 3, 4, 5, 6, 7, and 9, as well as the parent compound, oxycodone. The objective was to determine the pharmacokinetics of the parent compound and its various oligomer conjugates administered both intravenously and orally.

A summary of plasma PK parameters following IV (1 mg/kg) and PO (5 mg/kg) delivery for oxycodone, $mPEG_0$-oxycodone, $mPEG_1$-O-hydroxycodone, $mPEG_2$-O-hydroxycodone, $mPEG_3$-O-hydroxycodone, $mPEG_4$-O-hydroxycodone, $mPEG_5$-O-hydroxycodone, $mPEG_6$-O-hydroxycodone, $mPEG_7$-O-hydroxycodone, and $mPEG_9$-O-hydroxycodone, are shown in the following tables, Tables 4 and 5.

Based on the observed data (Table 4) for IV administration, $mPEG_9$-O-hydroxycodone appeared to achieve higher plasma concentration with a mean $t_{1/2}$ value 3 times that of the corresponding mean $t_{1/2}$ value observed after parent oxycodone was given.

Figure 10:
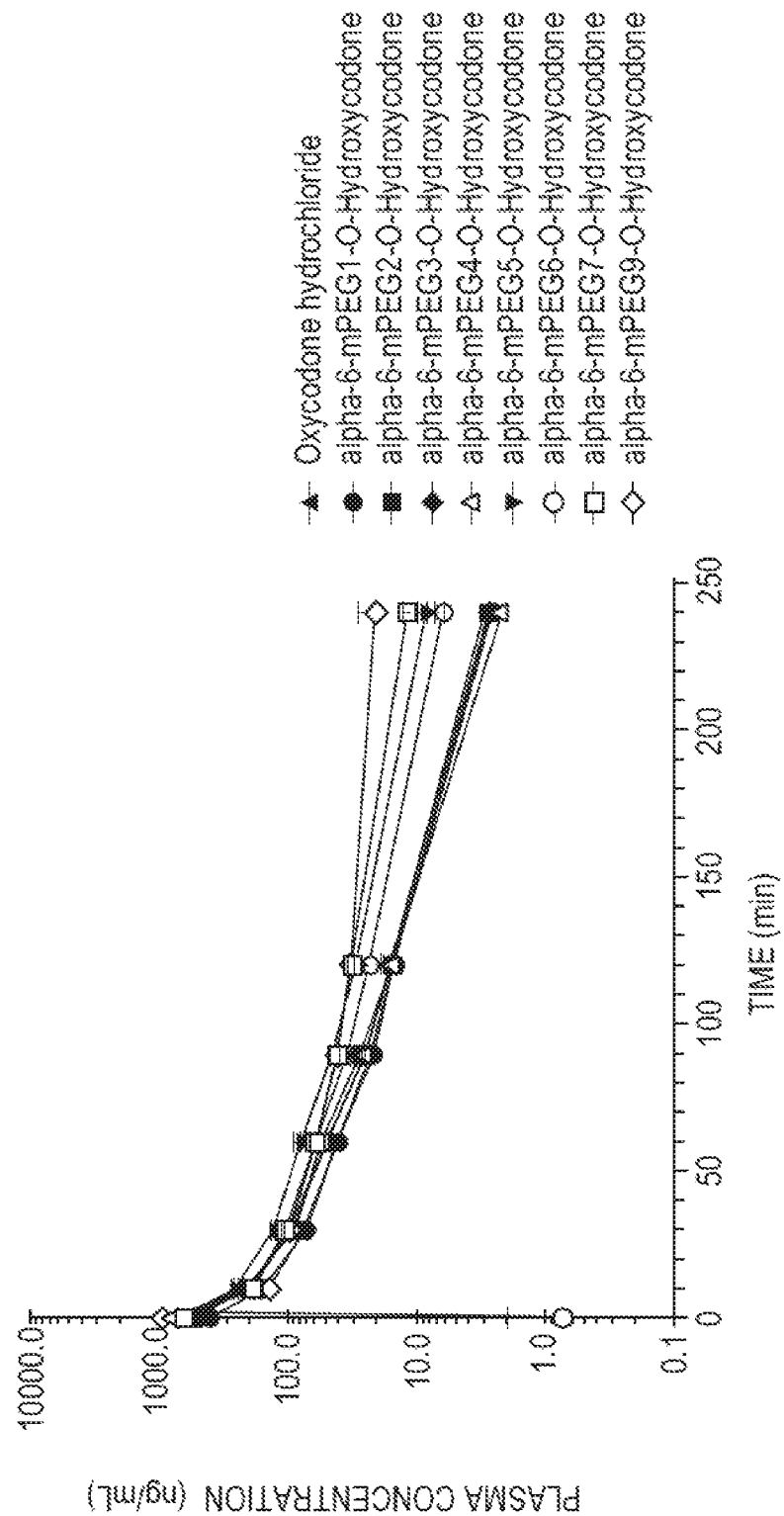
FIG. 10 shows the mean (+SD) plasma concentration-time profiles for the compounds, oxycodone (mPEG$_0$-oxycodone), mPEG$_1$-O-hydroxycodone, mPEG$_2$-O-hydroxycodone, mPEG$_3$-O-hydroxycodone, mPEG$_4$-O-hydroxycodone, mPEG$_5$-O-hydroxycodone, mPEG$_6$-O-hydroxycodone, mPEG$_7$-O-hydroxycodone, and mPEG$_9$-O-hydroxycodone, following 1.0 mg/kg intravenous administration to rats as described in Example 21.

FIG. 10 shows the mean plasma concentration-time profiles for IV-administered mPEGn-O-hydroxycodone compounds as described above, as well as for oxycodone per se, when administered at a concentration of 1.0 mg/kg.

Based on the observed data (Table 5) for oral administration, $mPEG_5$-O-hydroxycodone, $mPEG_6$-O-hydroxycodone, and $mPEG_7$-O-hydroxycodone appeared to achieve higher mean exposure (approximately 3- to 8-fold) in plasma as compared to parent molecule, oxycodone.

Figure 11:
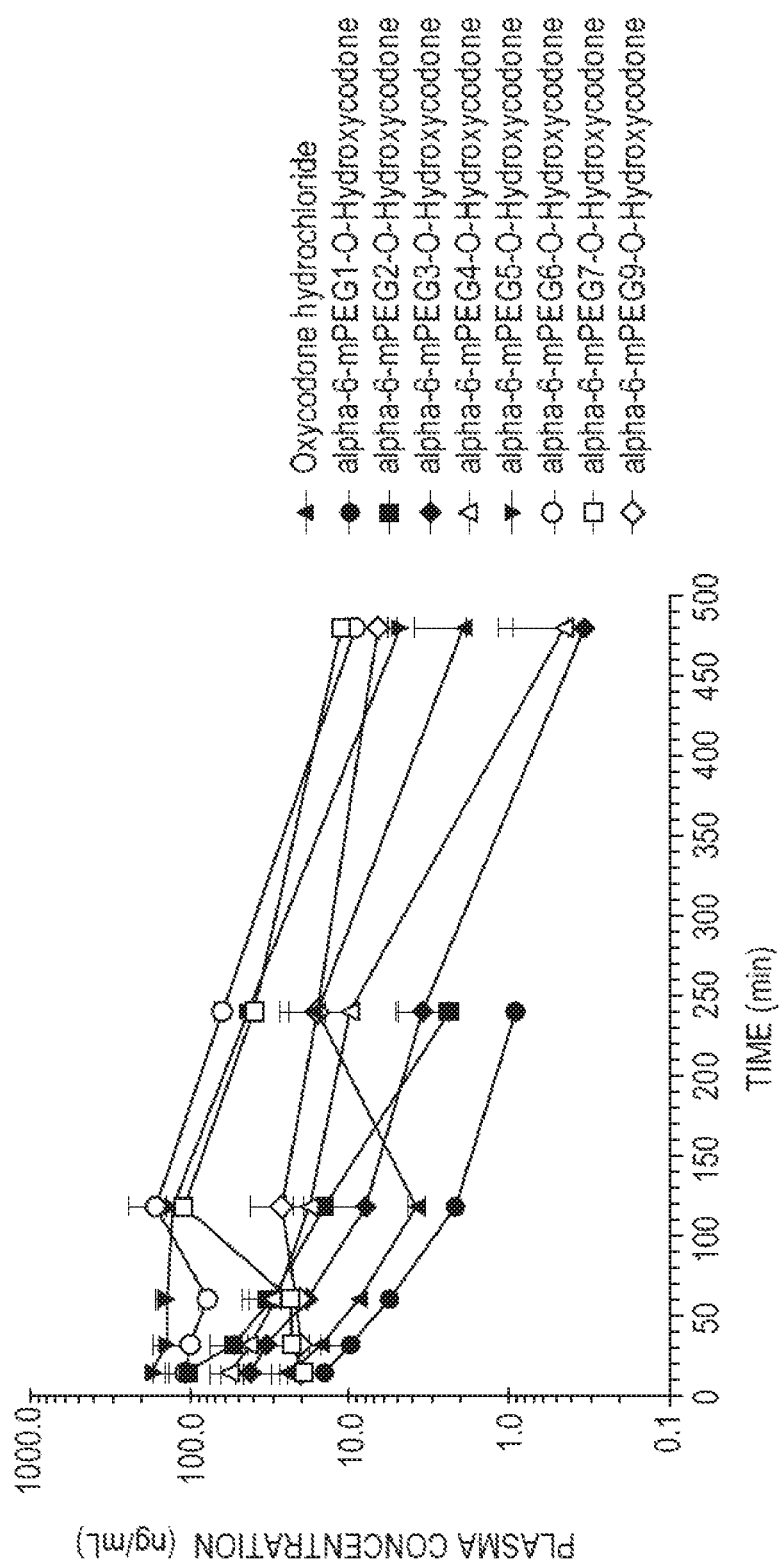
FIG. 11 shows the mean (+SD) plasma concentration-time profiles for the compounds, oxycodone (mPEG$_0$-oxycodone), mPEG$_1$-O-hydroxycodone, mPEG$_2$-O-hydroxycodone, mPEG$_3$-O-hydroxycodone, mPEG$_4$-O-hydroxycodone, mPEG$_5$-O-hydroxycodone, mPEG$_6$-O-hydroxycodone, mPEG$_7$-O-hydroxycodone, and mPEG$_9$-O-hydroxycodone, following 5.0 mg/kg oral administration to rats as described in Example 21.

FIG. 11 shows the mean plasma concentration-time profiles for the $mPEG_n$-O-hydroxycodone compounds described above, as well as for oxycodone, when administered orally to rats at a concentration of 5.0 mg/kg.

TABLE 4

Comparative PK Parameters of $mPEG_n$-O-hydroxycodone conjugates given intravenously to rats (Mean ± SD)

| PEG-length | $C_{max}$ (ng/mL) | $T_{1/2}$ (z) min | $AUC_{all}$ (min · ng/mL) | $AUC_{inf}$ (min · ng/mL) | $MRT_{last}$ min | CL (mL/min/kg) | $V_{ss}$ (L/kg) |
|---|---|---|---|---|---|---|---|
| 0 | 495 ± 56.0 | 47.0 ± 3.99 | 12800 ± 1090 | 13000 ± 1070 | 37.0 ± 1.28 | 77.1 ± 6.26 | 3.17 ± 0.293 |
| 1 | 425 ± 41.3 | 47.2 ± 6.37 | 9890 ± 1320 | 10100 ± 1440 | 38.7 ± 4.54 | 100 ± 13.4 | 4.31 ± 0.222 |
| 2 | 513 ± 48.8 | 44.6 ± 1.80 | 12000 ± 1610 | 12200 ± 1650 | 37.0 ± 2.60 | 83.3 ± 10.8 | 3.36 ± 0.298 |
| 3 | 746 ± 2.08 | 48.5 ± 7.83 | 13800 ± 1050 | 14000 ± 1010 | 32.5 ± 1.92 | 71.7 ± 4.99 | 2.62 ± 0.206 |
| 4 | 537 ± 31.0 | 43.6 ± 3.27 | 11500 ± 783 | 11600 ± 827 | 35.6 ± 2.88 | 86.5 ± 6.36 | 3.34 ± 0.113 |
| 5 | 622 ± 39.7 | 62.1 ± 3.85 | 16900 ± 1800 | 17700 ± 1990 | 46.2 ± 1.86 | 57.0 ± 6.07 | 3.30 ± 0.184 |
| 6 | 445 ± 83.6 | 62.2 ± 5.17 | 12600 ± 2370 | 13100 ± 2390 | 47.7 ± 1.41 | 77.9 ± 14.4 | 4.68 ± 0.938 |
| 7 | 489 ± 26.5 | 87.0 ± 3.25 | 14300 ± 583 | 15800 ± 728 | 54.3 ± 0.372 | 63.3 ± 2.99 | 5.31 ± 0.139 |
| 9 | 955 ± 149 | 143 ± 14.3 | 16600 ± 2190 | 21000 ± 4230 | 52.7 ± 4.04 | 48.9 ± 9.41 | 6.35 ± 0.349 |

TABLE 5

Comparative PK Parameters of mPEG$_n$-O-hydroxycodone conjugates given orally to Sprague Dawley rats (Mean ± SD)

| PEG-length | $C_{max}$ (ng/mL) | $T_{1/2(z)}$ min | AUC$_{all}$ (min · ng/mL) | AUC$_{inf}$ (min · ng/mL) | $T_{max}$* min | MRT$_{last}$ min | F % |
|---|---|---|---|---|---|---|---|
| 0 | 25.5 ± 1.86 | NC | 4520 ± 1660 | NC | 15.0 | 179 ± 17.4 | 7.1 |
| 1 | 14.3 ± 6.43 | 57.7* | 1050 ± 205 | 1150* | 15.0 | 66.8 ± 23.8 | 2.1 |
| 2 | 99.4 ± 47.3 | 48.5 ± 12.0 | 5910 ± 2690 | 5830 ± 2600 | 15.0 | 55.4 ± 14.7 | 9.4 |
| 3 | 44.5 ± 29.4 | 65.6* | 3620 ± 1910 | 4210* | 15.0 | 84.7 ± 17.0 | 5.3 |
| 4 | 55.8 ± 4.69 | 70.3* | 6340 ± 1810 | 5280* | 15.0 | 96.6 ± 33.6 | 11.0 |
| 5 | 178 ± 14.7 | 75.8 ± 1.08 | 32800 ± 2020 | 33300 ± 2090 | 15.0 | 124 ± 4.84 | 37.6 |
| 6 | 171 ± 76.6 | 85.4 ± 7.83 | 35100 ± 10100 | 36200 ± 10200 | 120 | 154 ± 6.46 | 55.3 |
| 7 | 114 ± 38.0 | 115 ± 29.2 | 20400 ± 3670 | 22200 ± 2900 | 120 | 178 ± 6.09 | 28.1 |
| 9 | 27.6 ± 19.6 | 106 (n = 1) | 7620 ± 4510 | 13500 (n = 1) | 120 | 203 ± 43.8 | 9.2 |

*n = 2,
NC: Not calculated.
$T_{max}$ is reported as median value.

To summarize the results, intravenous administration of PEGylated hydroxycodone with varying oligomeric PEG-lengths (PEG1 to PEG9) resulted in variable plasma concentrations and exposures as compared to oxycodone. PEGs with chain lengths 3, 5, 7 and 9 showed higher mean exposure (AUC) while PEG6 showed comparable mean exposure (AUC) and PEGs with chain lengths 1, 2 or 4 showed slightly lower mean exposure (AUC). The compounds having a PEG length greater than 5 showed trends of lower clearance, higher volume of distribution at steady state, increase in elimination half life values, with increasing PEG length.

Oral administration of PEGylated hydroxycodone with varying oligomeric PEG-lengths (PEG1 to PEG9) resulted in improvement in plasma exposure with the exception of hydroxycodone covalently attached to PEG1 and to PEG3. Oral bioavailability was highest for hydroxycodone covalently attached to mPEG6, 55.3%) followed by mPEG5-hydroxycodone and mPEG7-hydroxycodone with 37.6% and 28.1%, respectively. The elimination half-life values showed a trend of increasing with increase in PEG-length.

Example 22

IV and PO Pharmacokinetics of mPEG$_n$-O-Morphine Conjugates

A pharmacokinetic study was conducted in Sprague-Dawley rats as described in Example 20 above. Compounds administered were mPEG$_n$-O-morphine conjugates where n=1, 2, 3, 4, 5, 6, 7, and 9, as well as the parent compound, morphine. The objective was to determine the pharmacokinetics of the parent compound and its various oligomer conjugates administered both intravenously and orally.

A summary of plasma PK parameters following IV (1 mg/kg) and PO (5 mg/kg) routes for morphine, mPEG$_1$-O-morphine, mPEG$_2$-O-morphine, mPEG$_3$-O-morphine, mPEG$_4$-O-morphine, mPEG$_5$-O-morphine, mPEG$_6$-O-morphine, mPEG$_7$-O-morphine, mPEG$_9$-O-morphine, are shown in Table 6 and Table 7, respectively.

Figure 12:
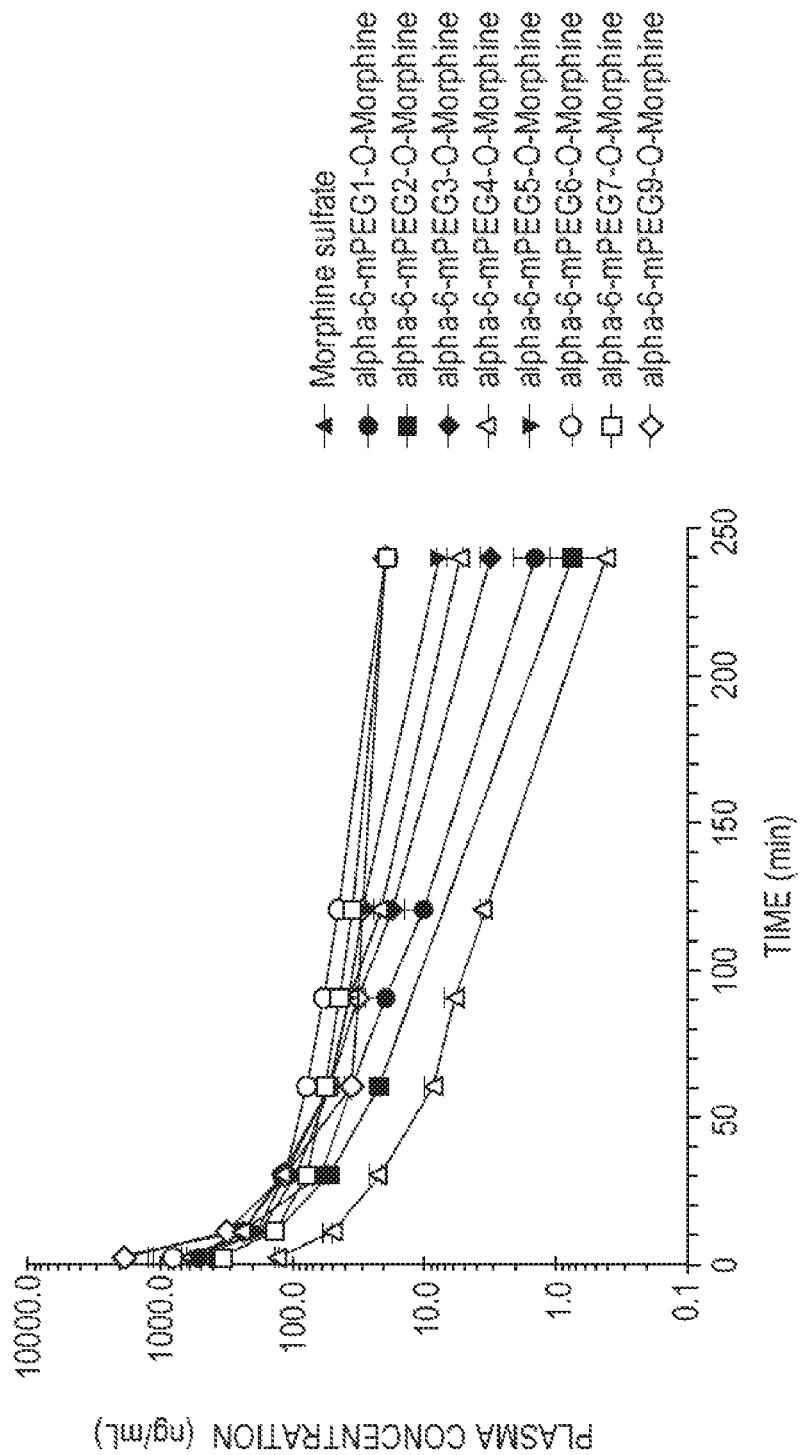
FIG. 12 shows the mean (+SD) plasma concentration-time profiles for the compounds, morphine (mPEG$_0$-morphine), and mPEG$_{1-7, 9}$-O-morphine conjugates, following 1.0 mg/kg intravenous administration to rats as described in detail in Example 22.

For the intravenous group: FIG. 12 shows the mean plasma concentration-time profiles for the above mPEG$_n$-O-morphine conjugates after 1.0 mg/kg intravenous administration to rats. There appeared to be one outlier datum in each animal that are inconsistent with plasma profiles of mPEG$_2$-O-morphine, and were excluded from the PK analysis.

Based on the observed data (Table 6), mPEG$_9$-O-morphine appeared to achieve higher plasma concentration with a mean $t_{1/2}$ value 4 times that of the corresponding $t_{1/2}$ value observed after parent morphine was given.

TABLE 6

Comparative PK Parameters of mPEG$_n$-O-morphine Conjugates given intravenously to rats

| PEG-Length | $C_{max}$ (ng/mL) | $T_{1/2(z)}$ min | AUC$_{all}$ (min · ng/mL) | AUC$_{inf}$ (min · ng/mL) | MRT$_{last}$ min | CL (mL/min/kg) | $V_{ss}$ (L/kg) |
|---|---|---|---|---|---|---|---|
| 0 | 132 ± 5.86 | 51.1 ± 20.8 | 2730 ± 276 | 2760 ± 218 | 28.5 ± 6.79 | 364 ± 27.5 | 14.9 ± 4.0 |
| 1 | 483 ± 37.1 | 40.0 ± 2.58 | 11400 ± 1230 | 11500 ± 1260 | 29.8 ± 5.05 | 87.8 ± 9.40 | 2.75 ± 0.236 |
| 2 | 378 ± 48.8 | 38.1 ± 8.03 | 7510 ± 106 | 7410 ± 404 | 26.4 ± 5.90 | 135 ± 7.60 | 4.2 ± 0.270 |
| 3 | 483 ± 81.0 | 45.0 ± 2.73 | 12700 ± 1950 | 12900 ± 1990 | 39.3 ± 1.69 | 78.5 ± 11.8 | 3.43 ± 0.616 |
| 4 | 622 ± 72.5 | 52.9 ± 6.50 | 14600 ± 1140 | 15000 ± 1270 | 40.1 ± 0.962 | 67.1 ± 5.58 | 3.17 ± 0.168 |
| 5 | 514 ± 38.6 | 68.4 ± 0.826 | 13200 ± 998 | 14000 ± 1050 | 49.7 ± 1.20 | 71.6 ± 5.17 | 4.74 ± 0.347 |
| 6 | 805 ± 30.6 | 93.7 ± 17.1 | 19000 ± 1430 | 21600 ± 2060 | 56.2 ± 3.84 | 46.6 ± 4.67 | 4.39 ± 0.630 |
| 7 | 1110 ± 123 | 111 ± 32.9 | 18100 ± 956 | 21200 ± 1990 | 49.6 ± 5.20 | 47.4 ± 4.21 | 4.76 ± 0.997 |
| 9 | 1840 ± 123 | 204 ± 28.3 | 23300 ± 1460 | 29000 ± 3240 | 34.2 ± 2.72 | 34.7 ± 3.64 | 4.52 ± 0.473 |

Figure 13:
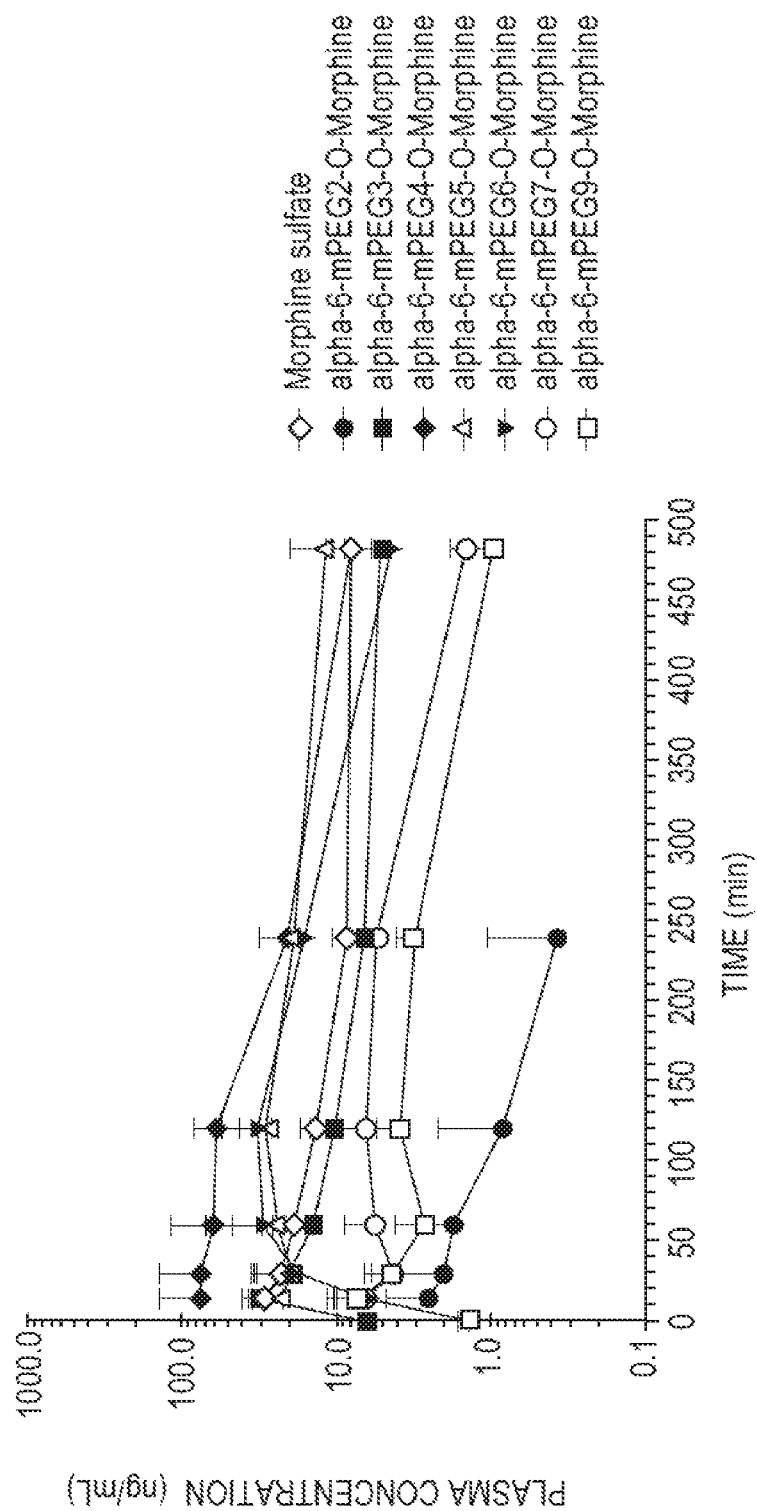
FIG. 13 shows the mean (+SD) plasma concentration-time profiles for the compounds, morphine (mPEG$_0$-morphine), and mPEG$_{1-7, 9}$-O-morphine conjugates, following 5.0 mg/kg oral administration to rats as described in Example 22.

For the oral group, FIG. 13 shows the mean plasma concentration-time profiles for the above described mPEG$_n$-O-morphine conjugates after the oral administration (5.0 mg/kg) to rats.

Based on the observed data (Table 7), mPEG$_4$-O-morphine appeared to achieve highest plasma concentrations among the conjugates tested as compared to parent molecule, morphine.

TABLE 7

Comparative PK Parameters of mPEG$_n$-O-morphine conjugates given orally to Sprague Dawley rats (Mean ± SD)

| PEG-Length | $C_{max}$ (ng/mL) | $T_{1/2(z)}$ min | AUC$_{all}$ (min · ng/mL) | AUC$_{inf}$ (min · ng/mL) | $T_{max}$ min | MRT$_{last}$ min | F % |
|---|---|---|---|---|---|---|---|
| 0 | 29.8 ± 7.78 | 144 ± 32.1 | 5510 ± 667 | 7230 ± 897 | 15.0 | 194 ± 22.0 | 40.4[¥] |
| 2 | 3.84* | 104* | 448* | 778* | 15.0* | 60.7* | 0.15 |
| 3 | 30.3 ± 4.42 | 377* | 4250 ± 2140 | 8370* | 15.0 | 151 ± 69.4 | 9.0 |
| 4 | 87.1 ± 53.6 | 191 ± 104 | 15600 ± 7690 | 18200 ± 10300 | 30.0 | 149 ± 26.7 | 22.1 |
| 5 | 35.6 ± 19.8 | 247* | 9190 ± 5650 | 17400* | 120 | 205 ± 26.2 | 13.9 |
| 6 | 42.8 ± 31.2 | 121* | 8290 ± 4970 | 10800* | 120 | 177 ± 29.4 | 8.7 |
| 7 | 9.38 ± 0.883 | 236* | 2210 ± 221 | 2720* | 60.0 | 187 ± 32.0 | 2.4 |
| 9 | 7.15 ± 3.34 | 363* | 1360 ± 311 | 2270* | 15.0 | 166 ± 26.0 | 1.2 |

No PK parameters were not reported for mPEG$_1$-morphine because all the concentrations were <LLOQ.
*n = 2.

In summary, for the IV data, administration of oligomeric PEGylated morphine with varying PEG-lengths (PEG1 to PEG9) resulted in higher plasma concentrations and exposure (AUC) as compared to morphine per se. There was a clear trend of increase in mean AUC with increase in PEG-length of 5 onwards, with 10-fold higher mean AUC for the PEG9-morphine compound as compared to non-conjugated morphine. The mean half-life and mean residence time also increased with increase in PEG-length. The lower mean clearance values were consistent with observed higher mean AUC values.

Mean volume of distribution estimated for steady state, immediately decreased by 5-fold with the introduction of single PEG, and reached a constant value at PEG-length 5. Overall, PEGylation appeared to increase the elimination $t_{1/2}$ and lower the tissue distribution of morphine.

Based upon the oral data, administration of PEGylated morphine conjugates with varying PEG-lengths (PEG1 to PEG9) resulted in a reduction in oral bioavailability compared to morphine. The reduction in bioavailability appeared to be related to the absorption component rather than metabolism component for these PEG-conjugates. Among the PEG-conjugates, the conjugate with PEG-length 4 showed maximum F-value (22.1%) while conjugates with shorter or longer PEG-length showed a clear trend of loss in absorption.

In this study, morphine F % value was 3-fold higher than literature value of 15% at 7.5 mg/kg (J. Pharmacokinet. Biopharm. 1978, 6:505-19). The reasons for this higher exposure are not known.

Example 23

IV and PO Pharmacokinetics of mPEG$_n$-O-Codeine Conjugates

A pharmacokinetic study was conducted in Sprague-Dawley rats as described in Example 20 above. Compounds administered were mPEG$_n$-O-codeine conjugates where n=1, 2, 3, 4, 5, 6, 7, and 9, as well as the parent compound, codeine (n=0). The objective was to determine the pharmacokinetics of the parent compound, i.e., codeine, and its various oligomer conjugates administered both intravenously and orally.

A summary of plasma PK parameters following IV (1 mg/kg) and PO (5 mg/kg) routes for codeine, mPEG$_1$-O-codeine, mPEG$_2$-O-codeine, mPEG$_3$-O-codeine, mPEG$_4$-O-codeine, mPEG$_5$-O-codeine, mPEG$_6$-O-codeine, mPEG$_7$-O-codeine, mPEG$_9$-O-codeine, are shown in Table 8 and Table 9, respectively.

Figure 14:
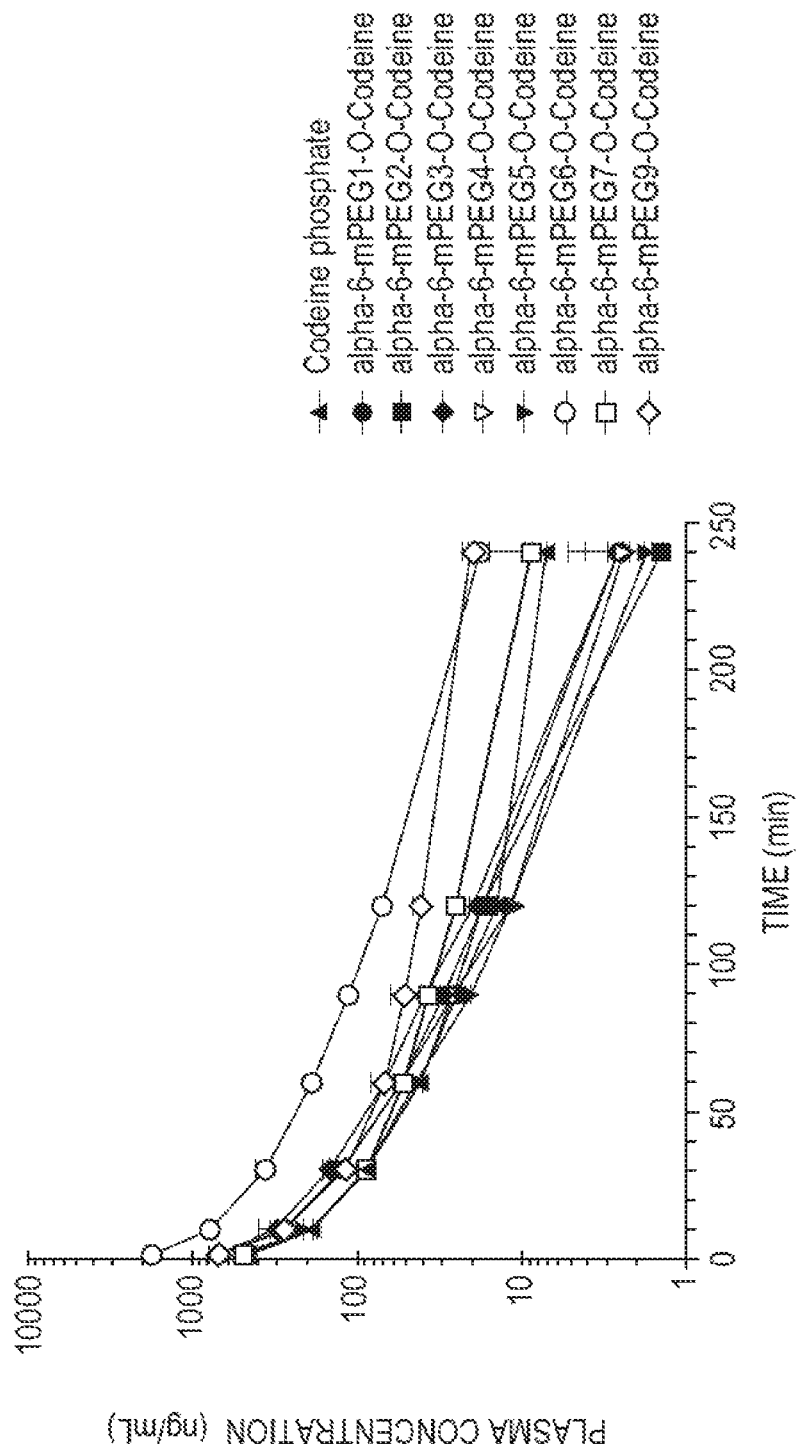
FIG. 14 shows the mean (+SD) plasma concentration-time profiles for the compounds, codeine (mPEG$_0$-codeine), and mPEG$_{1-7, 9}$-O-codeine conjugates, following 1.0 mg/kg intravenous administration to rats as described in detail in Example 23.

For the IV group: FIG. 14 shows the mean plasma-concentration-time profiles for parent molecule, codeine, as well as for the mPEG$_n$-O-codeine conjugates described above, after intravenous administration.

Based on the observed data (Table 8), mPEG$_6$-O-codeine appeared to achieve higher plasma concentrations among the tested conjugates with a mean $t_{1/2}$ value approximately 2.5 times that of the corresponding $t_{1/2}$ value observed following administration of the parent molecule, codeine.

TABLE 8

Comparative PK Parameters of Codeine and its Oligomeric PEG Conjugates Admnistered Intravenously to Rats

| PEG-Length | $C_{max}$ (ng/mL) | $T_{1/2(z)}$ min | AUC$_{all}$ (min.ng/mL) | AUC$_{inf}$ (min.ng/mL) | MRT$_{last}$ min | CL (mL/min/kg) | $V_{ss}$ (L/kg) |
|---|---|---|---|---|---|---|---|
| 0 | 469 ± 20.4 | 42.1 ± 3.15 | 11000 ± 1600 | 11400 ± 2070 | 40.2 ± 9.08 | 89.7 ± 15.3 | 4.14 ± 0.700 |
| 1 | 723 ± 31.2 | 42.1 ± 4.84 | 15500 ± 2020 | 15700 ± 2130 | 32.2 ± 4.59 | 64.6 ± 8.75 | 2.22 ± 0.899 |
| 2 | 685 ± 41.0 | 35.3 ± 2.78 | 14500 ± 1590 | 14600 ± 1590 | 31.5 ± 2.96 | 69.0 ± 7.57 | 2.25 ± 0.166 |
| 3 | 732 ± 27.1 | 39.4 ± 1.49 | 17300 ± 1520 | 17400 ± 1550 | 33.8 ± 2.40 | 57.7 ± 4.89 | 2.07 ± 0.127 |
| 4 | 746 ± 70.0 | 57.1 ± 43.8 | 15200 ± 2160 | 15400 ± 2240 | 27.5 ± 4.55 | 65.9 ± 10.4 | 2.30 ± 0.720 |
| 5 | 533 ± 38.9 | 42.7 ± 3.56 | 11500 ± 878 | 11700 ± 913 | 31.8 ± 1.53 | 86.2 ± 7.04 | 2.95 ± 0.157 |
| 6 | 1780 ± 149 | 58.0 ± 4.79 | 45600 ± 2020 | 47100 ± 2000 | 41.7 ± 3.08 | 21.3 ± 0.876 | 1.08 ± 0.143 |
| 7 | 443 ± 43.3 | 74.5 ± 5.76 | 12700 ± 481 | 13700 ± 320 | 50.7 ± 2.07 | 73.1 ± 1.73 | 5.20 ± 0.596 |
| 9 | 730 ± 68.0 | 109 ± 1.80 | 17800 ± 2310 | 20800 ± 2840 | 57.2 ± 2.46 | 48.6 ± 6.74 | 5.18 ± 0.538 |

Tmax is reported as median value.
*n = 2.

Figure 15:
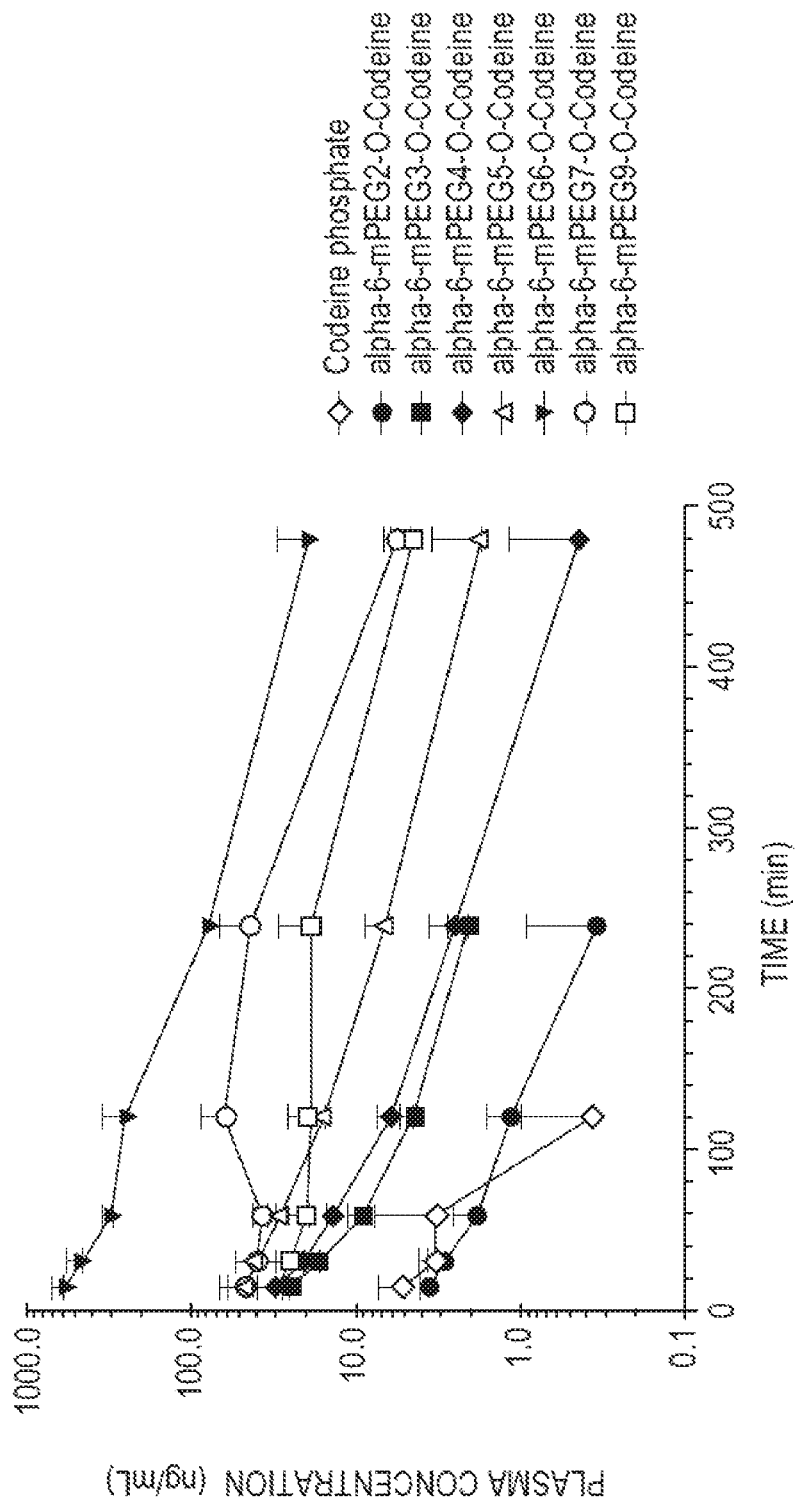
FIG. 15 shows the mean (+SD) plasma concentration-time profiles for the compounds, codeine (mPEG$_0$-codeine), and mPEG$_{1-7, 9}$-O-codeine conjugates, following 5.0 mg/kg oral administration to rats as described in Example 23.

For the oral group, FIG. 15 shows the mean plasma concentration-time profiles for parent molecule, codeine, versus mPEG$_n$-codeine conjugates after oral administration to rats (5.0 mg/kg).

Based on the observed data (Table 9), the PEG-6 compound, mPEG$_6$-codeine, appeared to achieve highest plasma concentrations (52 times higher mean AUCall) among

TABLE 9

Comparative PK Parameters of Codeine and Various mPEG$_n$-Codeine Conjugates given Orally to Sprague Dawley Rats (Mean ± SD)

| PEG-Length | $C_{max}$ (ng/mL) | $T_{1/2(z)}$ min | AUC$_{all}$ (min · ng/mL) | AUC$_{inf}$ (min · ng/mL) | $T_{max}$ min | MRT$_{last}$ min | F % |
|---|---|---|---|---|---|---|---|
| 0 | 6.24 ± 2.51 | 80.8[#] | 328 ± 216 | 431[#] | 15.0 | 33.2 ± 12.9 | 0.60 |
| 2 | 3.47 ± 0.606 | 97.6 ± 28.4 | 351 ± 195 | 419 ± 226 | 15.0 | 62.0 ± 27.4 | 0.57 |
| 3 | 25.0 ± 6.59 | 125 ± 64.6 | 1920 ± 245 | 2080 ± 498 | 15.0 | 71.0 ± 9.16 | 2.39 |
| 4 | 31.1 ± 13.1 | 118 ± 60.0 | 2530 ± 682 | 2670 ± 870 | 15.0 | 83.8 ± 22.5 | 3.47 |
| 5 | 48.7 ± 10.8 | 125 ± 63.7 | 5510 ± 963 | 5890 ± 1470 | 15.0 | 108 ± 35.4 | 10.1 |
| 6 | 617 ± 56.4 | 126 ± 54.1 | 70500 ± 12300 | 74500 ± 10000 | 15.0 | 119 ± 11.1 | 31.6 |
| 7 | 76.6 ± 12.8 | 97.6* | 17100 ± 4220 | 16000* | 120 | 171 ± 21.7 | 26.9 |
| 9 | 31.5 ± 8.43 | 143* | 7320 ± 3330 | 6840* | 15.0 | 179 ± 21.6 | 8.22 |

No PK parameters were not reported for NKT-10479 because the concentrations were LLOQ.
[#]n = 1,
*n = 2.
$T_{max}$ is reported as median value.

In summary, for the IV data, PEGylation of codeine with varying oligomeric PEG-lengths (PEG1 to PEG9) improved exposure (mean AUC) only slightly and moderate improvement (approximately 4-fold) was observed for the PEG-6 conjugate. Both clearance and volume of distribution decreased for this PEG-conjugate by 4-fold. Conjugates with PEG-lengths 7 and 9 showed longer mean $t_{1/2}$ values, however, mean clearance and mean volume of distribution (Vss) were decreased for both for both the PEG7- and PEG9-codeine conjugates.

For the oral data, oral bioavailability for codeine is very low (F=0.52%). Oral bioavailability appeared to increase with increase in PEG-length from 2 onwards, reaching maximum with 32% bioavailability for the codeine conjugate with PEG-length 6, decreasing thereafter. In general, mean $t_{1/2}$ and mean residence values increased with PEG-length. There was no difference in time to reach peak concentrations (Tmax=15 min) amongst all the compounds tested, suggesting that absorption was rapid and the absorption rate was not altered.

Example 24

In-Vitro Binding of mPEG$_n$-O-Opioid Conjugates to Opioid Receptors

The binding affinities of the various PEG-opioid conjugates (mPEG$_n$-O-morphine, mPEG$_n$-O-codeine, and mPEG$_n$-O-hydroxycodone) was measured in vitro in membrane preparations prepared from CHO cells that heterologously express the cloned human mu, kappa or delta opioid receptors. Radioligand displacement was measured using scintillation proximity assays (SPA).

Briefly, serial dilutions of the test compounds were placed in a 96-well plate to which were added SPA beads, membrane and radioligand. The assay conditions for each opioid receptor subtype are described in Table 10 below. The plates were incubated for 8 hours-overnight at room temperature, spun at 1000 rpm to pellet the SPA beads, and radioactivity was measured using the TopCount® microplate Scintillation counter. Specific binding at each concentration of test compound was calculated by subtracting the non-specific binding measured in the presence of excess cold ligand. IC$_{50}$ values were obtained by non-linear regression of specific binding versus concentration curves and Ki values were calculated using Kd values that were experimentally predetermined for each lot of membrane preparations.

TABLE 10

Assay conditions for opioid receptor binding assays

| EXPERIMENTAL VARIABLE | MU OPIOID RECEPTOR | KAPPA OPIOID RECEPTOR | DELTA OPIOID RECEPTOR |
|---|---|---|---|
| SPA beads | PVT-WGA PEI Type A (GE Healthcare, Cat. # RPNQ0003) | PVT-WGA (GE Healthcare, Cat. #RPNQ0001) | PVT-WGA PEI Type B (GE Healthcare, Cat. #RPNQ0004) |
| Radioligand; Concentration | DAMGO, [Tyrosyl-3,5-3H(N)]- (Perkin Elmer, Cat. # NET-902); 6 nM | U-69,593, [Phenyl-3,4-3H]- (Perkin Elmer, Cat. #NET-952); 10 nM | Naltrindole, [5',7'-3H]- (Perkin Elmer, Cat. #NET-1065); 3 nM |
| Non-specific binding control | CTAP | nor-Binaltorphimine (nor-BNI) | SNC80 |
| Buffer | 50 mM Tris-HCl, pH 7.5 5 mM MgCl2; 1 mM EDTA | 50 mM Tris-HCl, pH 7.5 5 mM MgCl2 | 50 mM Tris-HCl, pH 7.5 5 mM MgCl2 |
| Receptor and source | Recombinant human mu opioid receptor expressed in CHO-K1 host cell membranes (Perkin Elmer, | Recombinant human kappa opioid receptor expressed in Chem-1 host cell membranes | Recombinant human delta opioid receptor expressed in Chem-1 host cell membranes (Millipore, |

TABLE 10-continued

Assay conditions for opioid receptor binding assays

| EXPERIMENTAL VARIABLE | MU OPIOID RECEPTOR | KAPPA OPIOID RECEPTOR | DELTA OPIOID RECEPTOR |
|---|---|---|---|
| | Cat. #ES-542-M) | (Millipore, Cat. #HTS095M) | Cat. #HTS100M). |

The binding affinities of the oligomeric PEG conjugates of morphine, codeine and hydroxycodone are shown in Table 11. Overall, all of the conjugates displayed measurable binding to the mu-opioid receptor, consistent with the known pharmacology of the parent molecules. For a given PEG size, the rank order of mu-opioid binding affinity was PEG-morphine>PEG-hydroxycodone>PEG-codeine.
Increasing PEG size resulted in a progressive decrease in the binding affinity of all PEG conjugates to the mu opioid receptor compared to unconjugated parent molecule. However, the PEG-morphine conjugates still retained a high binding affinity that was within 15× that of parent morphine. The mu-opioid binding affinities of PEG-hydroxycodones were 20-50 fold lower than those of the PEG-morphine conjugates. Codeine and its PEG conjugates bound with very low affinity to the mu opioid receptor. PEG-morphine conjugates also bound to the kappa and delta opioid receptors; the rank order of selectivity was mu>kappa>delta. Binding affinities of codeine and hydroxycodone conjugates to the kappa and delta opioid receptors were significantly lower than that at the mu-opioid receptor.

TABLE 11

Binding affinities of the PEG-opioid conjugates to opioid receptors.

| | KI (NM) | | |
|---|---|---|---|
| COMPOUND | Mu opioid receptor | Kappa opioid receptor | Delta opioid receptor |
| Morphine | 8.44 | 118.38 | 4,297 |
| α-6-mPEG$_1$-O-Morphine | 15.72 | 444.54 | 2,723 |
| α-6-mPEG$_2$-O-Morphine | 21.97 | 404.33 | 2,601 |
| α-6-mPEG$_3$-O-Morphine | 50.66 | 575.98 | 6,176 |
| α-6-mPEG$_4$-O-Morphine | 23.11 | 438.88 | 3,358 |
| α-6-mPEG$_5$-O-Morphine | 39.40 | 557.54 | 2,763 |
| α-6-mPEG$_6$-O-Morphine | 72.98 | 773.56 | 2,595 |
| α-6-mPEG$_7$-O-Morphine | 56.86 | 669.56 | 2,587 |
| α-6-mPEG$_9$-O-Morphine | 111.05 | 1253.71 | 5,783 |
| Oxycodone | 133.48 | N/A | N/A |
| α-6-mPEG$_1$-O-Hydroxycodone | 653.90 | N/A | N/A |
| α-6-mPEG$_2$-O-Hydroxycodone | 631.76 | N/A | N/A |
| α-6-mPEG$_3$-O-Hydroxycodone | 775.19 | N/A | N/A |
| α-6-mPEG$_4$-O-Hydroxycodone | 892.70 | N/A | N/A |
| α-6-mPEG$_5$-O-Hydroxycodone | 1862.14 | N/A | N/A |
| α-6-mPEG$_6$-O-Hydroxycodone | 1898.30 | N/A | N/A |
| α-6-mPEG$_7$-O-Hydroxycodone | 1607.19 | N/A | N/A |
| α-6-mPEG$_9$-O-Hydroxycodone | 3616.60 | N/A | N/A |
| Codeine | 1,953 | 28,067 | N/A |
| α-6-mPEG$_1$-O-Codeine | 1821.51 | 54669.89 | N/A |
| α-6-mPEG$_2$-O-Codeine | 1383.07 | 22603.05 | N/A |
| α-6-mPEG$_3$-O-Codeine | 4260.21 | 36539.78 | N/A |
| α-6-mPEG$_4$-O-Codeine | 2891.36 | 96978.61 | N/A |
| α-6-mPEG$_5$-O-Codeine | 2427.13 | 59138.22 | N/A |
| α-6-mPEG$_6$-O-Codeine | 14202.77 | >160,000 | N/A |
| α-6-mPEG$_7$-O-Codeine | 9963.93 | 108317.50 | N/A |
| α-6-mPEG$_9$-O-Codeine | 9975.84 | 72246.23 | N/A |

N/A indicates that Ki values could not be calculated since a 50% inhibition of binding was not achieved at the highest concentration of compound tested.

Example 25

In-Vitro Efficacy of mPEG$_n$-O-Opioid Conjugates to Inhibit cAMP Formation

The efficacy of the various PEG-opioid conjugates was measured by their ability to inhibit cAMP formation following receptor activation. Studies were conducted in CHO cells heterologously expressing the cloned human mu, kappa or delta opioid receptors. cAMP was measured using a cAMP HiRange homogenous time-resolved fluorescence assay (HTRF Assay), that is based on a competitive immunoassay principle (Cisbio, Cat.#62AM6PEC).

Briefly, suspensions of cells expressing either the mu, kappa or delta opioid receptors were prepared in buffer containing 0.5 mM isobutyl-methyl xanthine (IBMX). Cells were incubated with varying concentrations of PEG-opioid conjugates and 3 μM forskolin for 30 minutes at room temperature. cAMP was detected following a two-step assay protocol per the manufacturer's instructions and time resolved fluorescence was measured with the following settings: 330 nm excitation; 620 nm and 665 nm emission; 380 nm dichroic mirror. The 665 nm/620 nm ratio is expressed as Delta F % and test compound-related data is expressed as a percentage of average maximum response in wells without forskolin. EC$_{50}$ values were calculated for each compound from a sigmoidal dose-response plot of concentrations versus maximum response. To determine if the compounds behaved as full or partial agonists in the system, the maximal response at the highest tested concentrations of compounds were compared to that produced by a known full agonist.

The EC$_{50}$ values for inhibition of cAMP formation in whole cells are shown in Table 12. Oligomeric PEG conjugates of morphine, codeine and hydroxycodone were full agonists at the mu opioid receptor, albeit with varying efficacies. Morphine and its conjugates were the most potent of the three series of opioids tested, while the PEG hydroxycodone and PEG codeine conjugates displayed significantly lower efficacies. A progressive decrease in the efficacy of the PEG-morphine conjugates was observed with increasing PEG size, however the conjugates retained mu-agonist potency to within 40× of parent. In contrast to the effect at the mu opioid receptor, morphine and PEG-morphine conjugates behaved as weak partial agonists at the kappa opioid receptor, producing 47-87% of the maximal possible response. EC$_{50}$ values could not be calculated for the codeine and hydroxycodone conjugates at the kappa and delta opioid receptors since complete dose-response curves could not be generated with the range of concentrations tested (up to 500 μM).

Overall, the results of the receptor binding and functional activity indicate that the PEG-opioids are mu agonists in vitro.

TABLE 12

In vitro efficacies of PEG-opioid conjugates

| COMPOUND | MU OPIOID RECEPTOR | | KAPPA OPIOID RECEPTOR | | DELTA OPIOID RECEPTOR |
|---|---|---|---|---|---|
| | $EC_{50}$, nM | % max effect | $EC_{50}$, nM | % max effect | |
| Morphine | 28.5 | 102 | 624 | 69 | N/A |
| α-6-mPEG$_1$-O-Morphine | 85.0 | 91 | 1,189 | 81 | N/A |
| α-6-mPEG$_2$-O-Morphine | 93.3 | 91 | 641 | 87 | N/A |
| α-6-mPEG$_3$-O-Morphine | 270 | 100 | 4,198 | 82 | N/A |
| α-6-mPEG$_4$-O-Morphine | 128 | 100 | 3,092 | 77 | N/A |
| α-6-mPEG$_5$-O-Morphine | 157 | 95 | 2,295 | 71 | N/A |
| α-6-mPEG$_6$-O-Morphine | 415 | 98 | 3,933 | 62 | N/A |
| α-6-mPEG$_7$-O-Morphine | 508 | 90 | 4,237 | 57 | N/A |
| α-6-mPEG$_9$-O-Morphine | 1,061 | 87 | 4,417 | 47 | N/A |
| Oxycodone | 478 | 95 | N/A | N/A | N/A |
| Hydroxycodone | 3,162 | | N/A | N/A | |
| α-6-mPEG$_1$-O-Hydroxycodone | 3,841 | 102 | N/A | N/A | N/A |
| α-6-mPEG$_2$-O-Hydroxycodone | 5,005 | 101 | N/A | N/A | N/A |
| α-6-mPEG$_3$-O-Hydroxycodone | 2,827 | 108 | N/A | N/A | N/A |
| α-6-mPEG$_4$-O-Hydroxycodone | 3,715 | 109 | N/A | N/A | N/A |
| α-6-mPEG$_5$-O-Hydroxycodone | 5,037 | 108 | N/A | N/A | N/A |
| α-6-mPEG$_6$-O-Hydroxycodone | 12,519 | 102 | N/A | N/A | N/A |
| α-6-mPEG$_7$-O-Hydroxycodone | 7,448 | 101 | N/A | N/A | N/A |
| α-6-mPEG$_9$-O-Hydroxycodone | 17,948 | 95 | N/A | N/A | N/A |
| Codeine | 10,418 | 81 | N/A | 3 | N/A |
| α-6-mPEG$_1$-O-Codeine | 8,574 | 80 | N/A | 51 | N/A |
| α-6-mPEG$_2$-O-Codeine | 5,145 | 75 | 40,103 | 59 | N/A |
| α-6-mPEG$_3$-O-Codeine | 19,740 | 91 | N/A | 49 | N/A |
| α-6-mPEG$_4$-O-Codeine | 22,083 | 99 | N/A | 61 | N/A |
| α-6-mPEG$_5$-O-Codeine | 23,235 | 95 | N/A | 60 | N/A |
| α-6-mPEG$_6$-O-Codeine | 97,381 | 80 | N/A | 21 | N/A |
| α-6-mPEG$_7$-O-Codeine | 44,729 | 75 | N/A | 48 | N/A |
| α-6-mPEG$_9$-O-Codeine | 48,242 | 80 | N/A | 61 | N/A |

Example 26

Brain:Plasma Ratios of mPEG$_n$-O-Opioid Conjugates

The ability of oligomeric mPEG-O-morphine, mPEG-O-codeine and mPEG-O-hydroxycodone conjugates to cross the blood brain barrier (BBB) and enter the CNS (central nervous system) was assessed by measuring the brain:plasma ratio in rats subsequent to IV administration.

Briefly, groups of 3 rats were injected intravenously (i.v) with 5 mg/kg each of morphine, mPEG$_n$-O-morphine conjugate, codeine and m-PEG$_n$-O-codeine conjugates. PEG-2,3 and 4-oxycodone conjugates were administered at 10 mg/kg i.v. and oxycodone and the other PEG sizes of oxycodone conjugates were administered at 1 mg/kg (i.v). The doses of the oxycodone conjugates had to be adjusted to allow for the detection of sufficient concentrations in brain tissue. Atenolol, which does not cross the BBB, was used as a measure of vascular contamination of the brain tissue and was administered at a concentration of 10 mg/kg to a separate group of rats. An hour following injection, the animals were sacrificed and plasma and the brain were collected and frozen immediately. Following tissue and plasma extractions, concentrations of the compounds in brain and plasma were measured using LC-MS/MS. The brain:plasma ratio was calculated as the ratio of measured concentrations in the brain and plasma. The results are shown in FIGS. 16A-C.

Figure 16A:
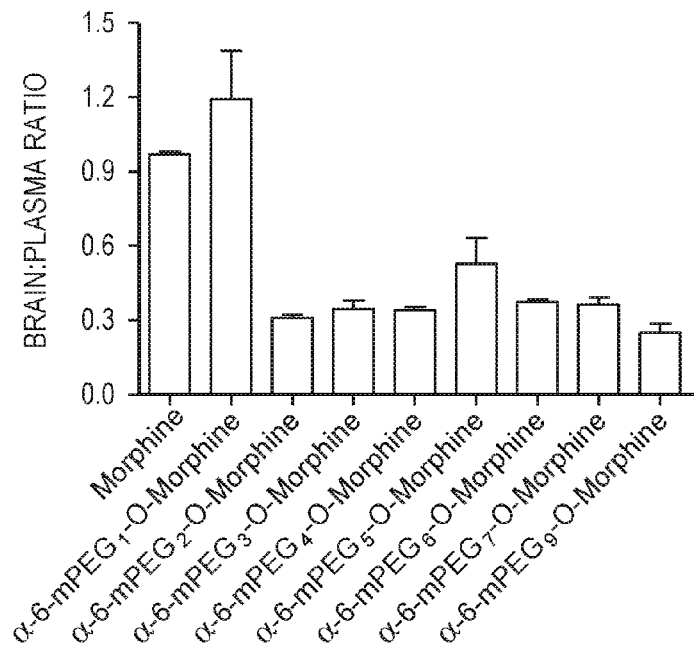
FIGS. 16A, 16B and 16C illustrate the brain:plasma ratios of various oligomeric mPEG$_n$-O-morphine, mPEG$_n$-O-codeine and mPEG$_n$-O-hydroxycodone conjugates, respectively, following IV administration to rats as described in Example 26. The brain:plasma ratio of atenolol is provided in each figure as a basis for comparison.
Figure 16B:
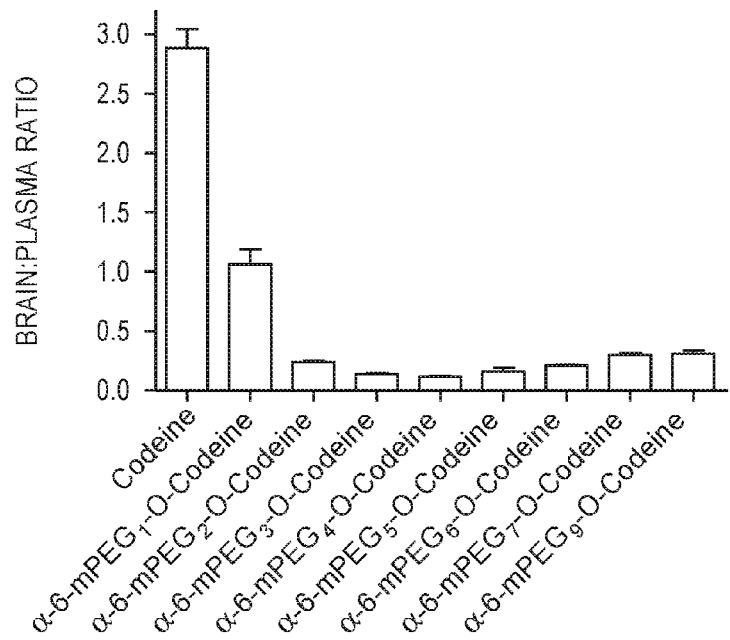
Figure 16C:
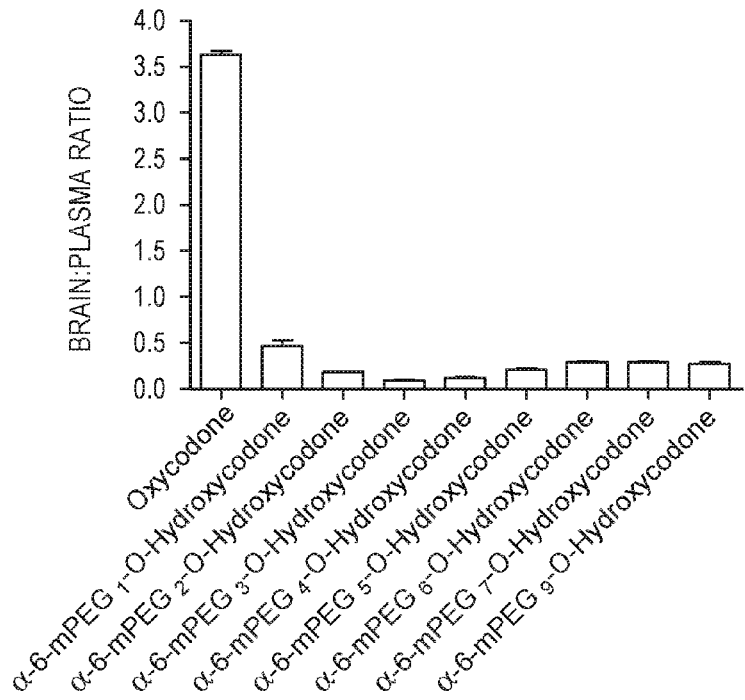
Figure 17A:
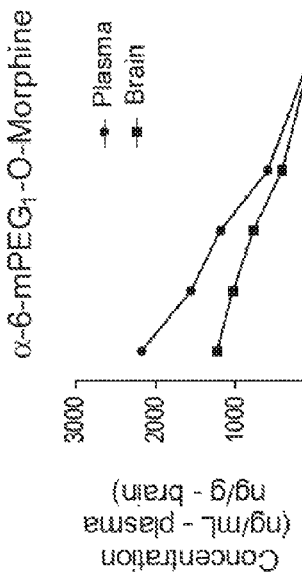
FIGS. 17A-H illustrate brain and plasma concentrations of morphine and various mPEG$_n$-O-morphine conjugates over time following IV administration to rats as described in Example 27.
Figure 17B:
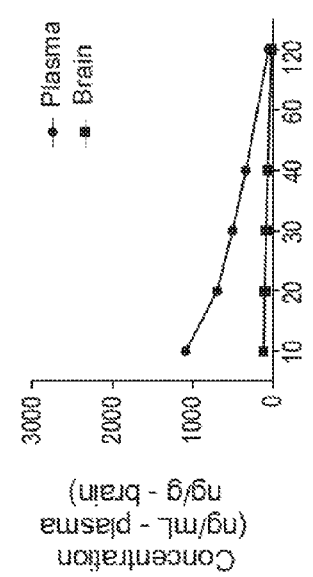
Figure 17C:
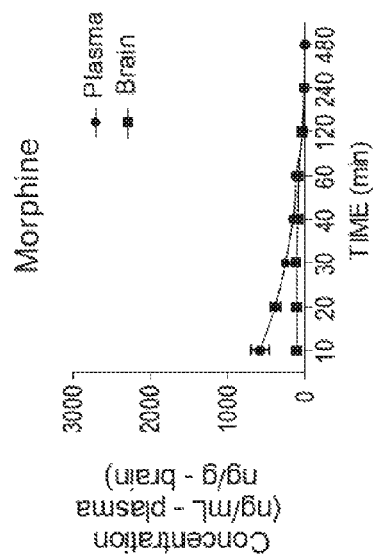
Figure 17D:
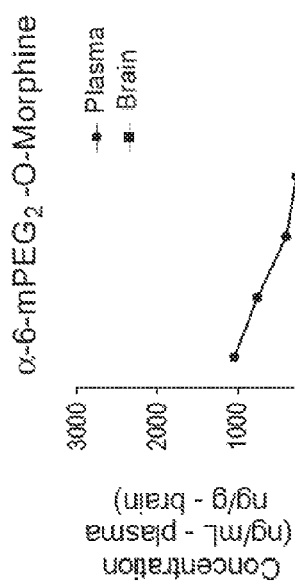
Figure 17E:
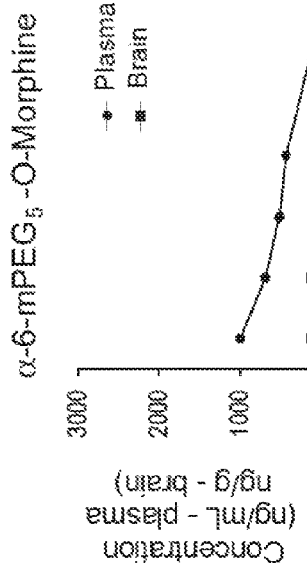
Figure 17F:
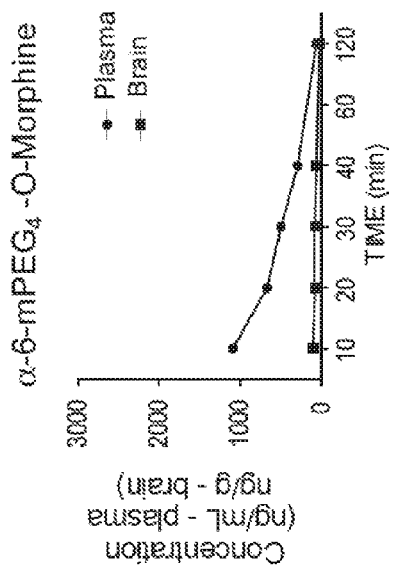
Figure 17G:
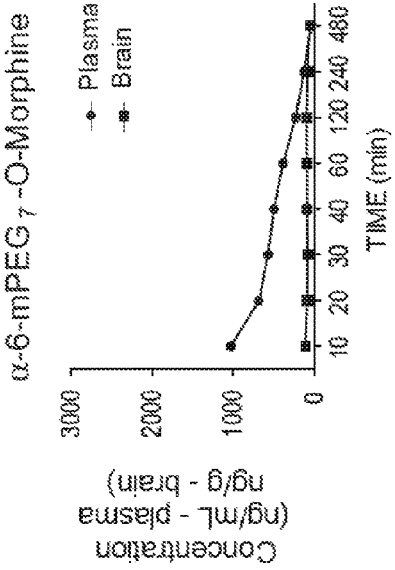
Figure 17H:
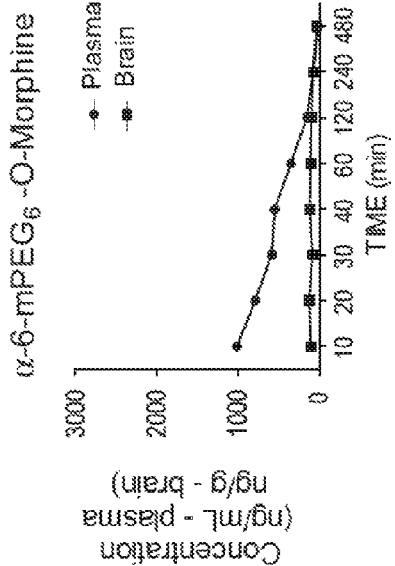
Figure 18A:
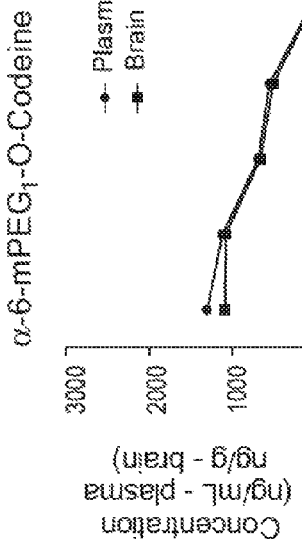
FIGS. 18A-H illustrate brain and plasma concentrations of codeine and various mPEG$_n$-O-codeine conjugates over time following IV administration to rats as described in Example 27.
Figure 18B:
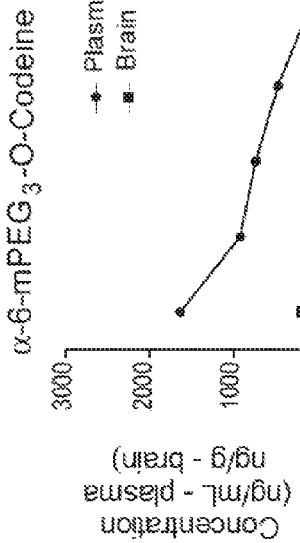
Figure 18C:
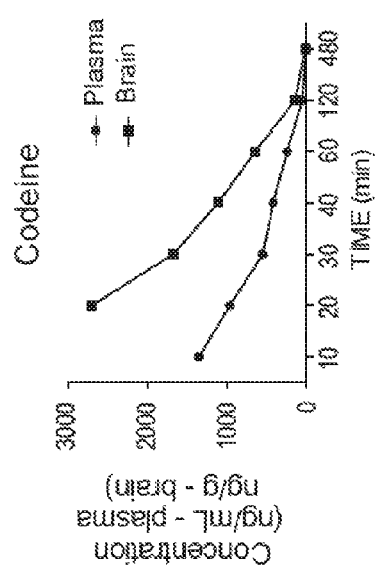
Figure 18D:
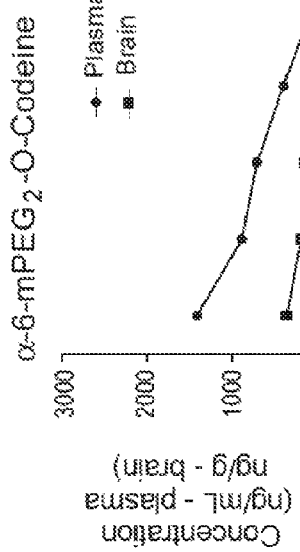
Figure 18E:
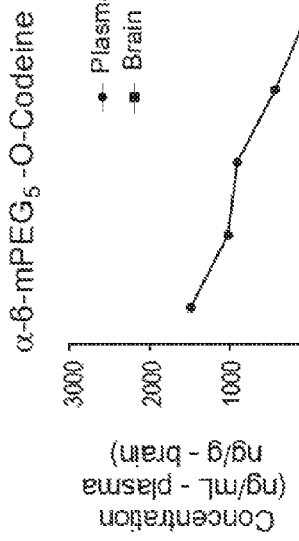
Figure 18F:
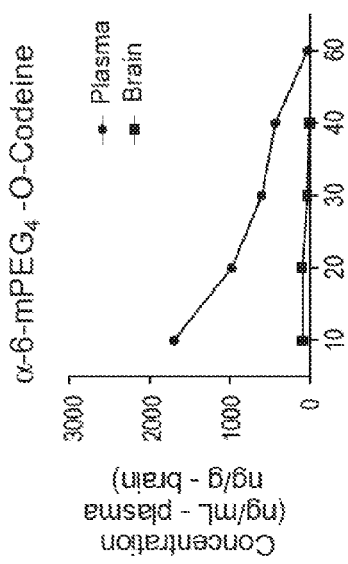
Figure 18G:
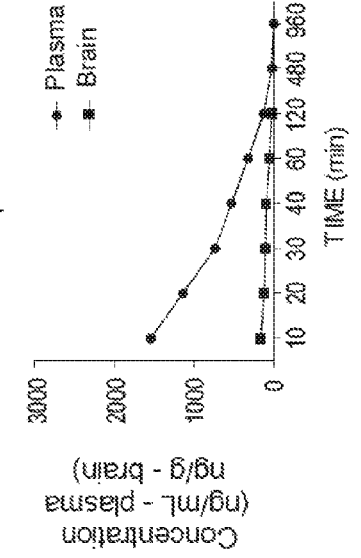
Figure 18H:
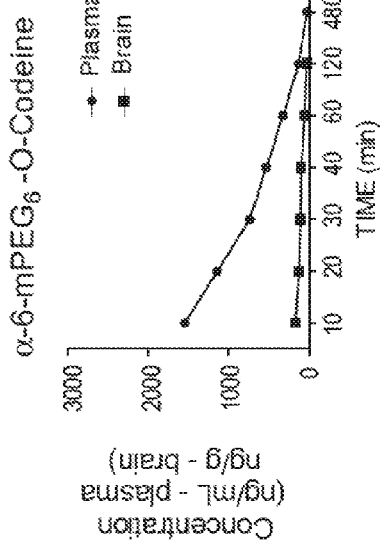
Figure 19E:
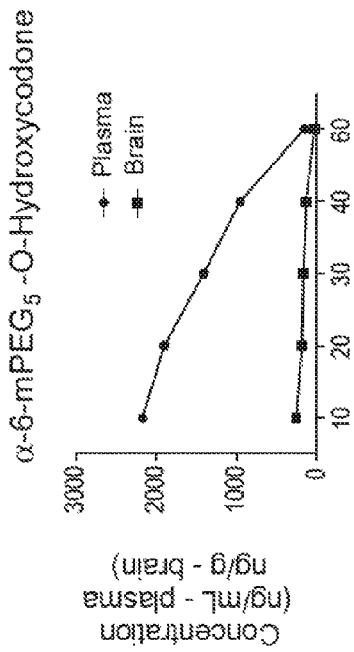
Figure 19F:
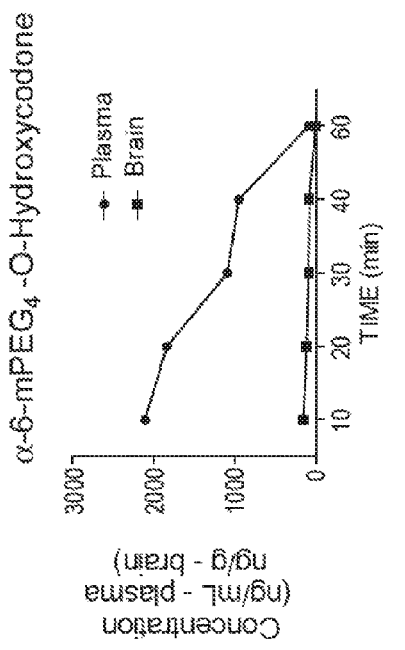
Figure 19G:
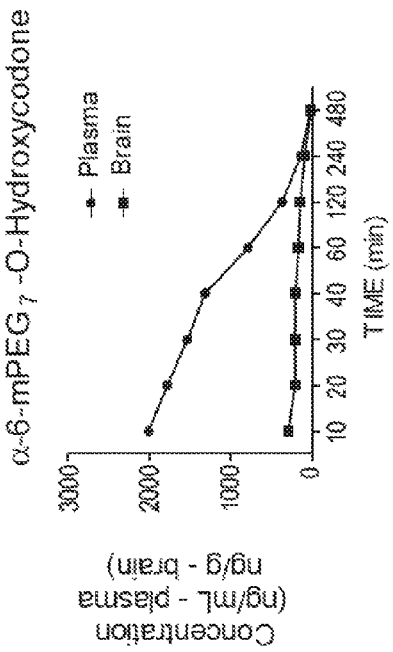
Figure 19H:
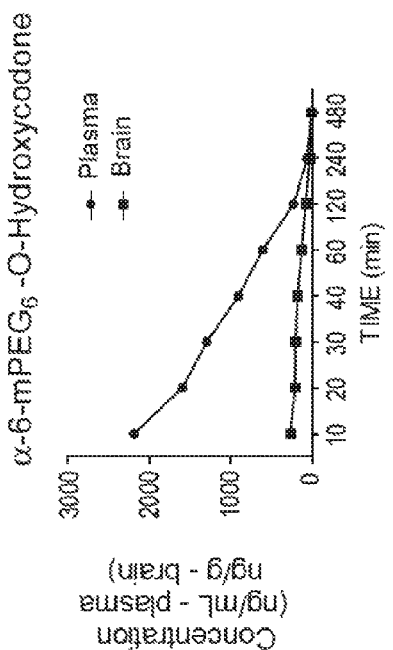

FIGS. 16A, 16B, and 16C show the brain:plasma ratios of various oligomeric mPEG$_n$-O-morphine, mPEG$_n$-O-codeine, and PEG$_n$-O-hydroxycodone conjugates, respectively. The brain:plasma ratio of atenolol is shown in each figure to provide a basis for comparison. PEG-conjugation results in a decrease in the brain:plasma ratio of all conjugates compared to their respective unconjugated parent molecule, which in the case of hydroxycodone is oxycodone. Only PEG-1-morphine displayed a greater brain:plasma ratio than its parent, morphine.

Example 27

Time-Course of Brain and Plasma Concentrations of Various Exemplary mPEG$_n$-O-Opioid Conjugates Experiments were conducted to determine the concentrations of various oligomeric PEG-opioid conjugates in brain and plasma over time following IV administration.

The experimental methodology and concentrations used were the same as those used for the single time point experiments described in Example 26, however, the brains and plasma were harvested at various differing time points.

All PEG-hydroxycodone conjugates were administered at 10 mg/kg iv, while the oxycodone parent was administered at 1 mg/kg iv. The data for the brain and plasma concentrations versus time for the various PEG-opioid conjugates administered is shown in FIGS. 17A-H (morphine series), FIGS. 18A-H (codeine series), and FIGS. 19A-H (oxycodone/hydroxycodone series).

The data demonstrate that the maximal increase in brain concentrations for all parent molecules and oligomeric PEG-conjugates occurs at the earliest time point, i.e., 10 minutes following iv injection. PEG conjugation results in a significant reduction in the brain concentrations and with the larger PEG conjugates (≥PEG-4), the brain concentrations remain relatively low and steady over time.

Example 28

Preparation of mPEG$_n$-O-Hydrocodonol Conjugates

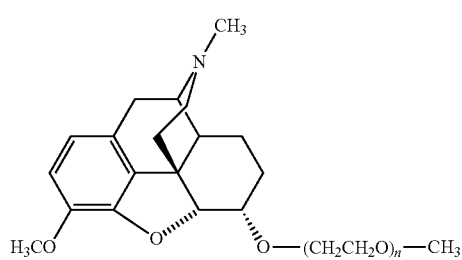

Preparation of mPEGn-OTs (mPEGn-tosylate) (n=1 through 9)

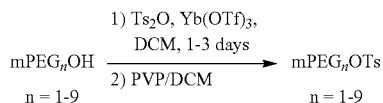

m-PEGn-OH, which may be dried under high vacuum (also after evaporation of a minor addition of heptane or toluene), was dissolved in DCM. Toluenesulfonic anhydride (Ts$_2$O, 1.05 eq.) and ytterbium (III) triflate (Yb(OTf)$_3$, 0.02 eq) were added and the reaction was allowed to stir overnight (reaction rate ranges from as fast as 1 day to 5 days to completely consume mPEG$_n$OH). Once mPEG$_n$OH was consumed, 2-3 equivalents of polyvinylpyridine was added with additional DCM to maintain stirring. After ≥24 hours, the PVP was filtered off and the filtrate was evaporated to yield ~95-100% yield after full vacuum.

Preparation of alpha-6-mPEG$_n$-O-Hydrocodonol Conjugate Synthesis (n=1 through 9)

alpha-6-mPEG$_n$-O-hydrocodonol was prepared as in accordance with the schematic provided below (wherein substantially the same approach was used for each of n=1 through 9).

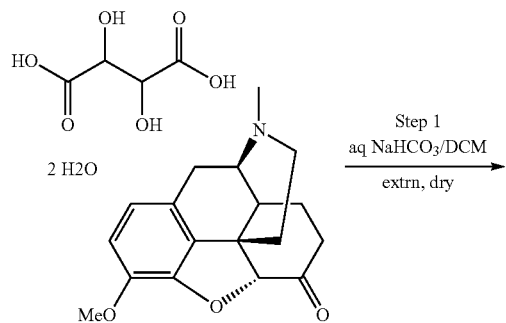

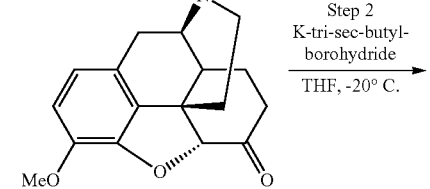

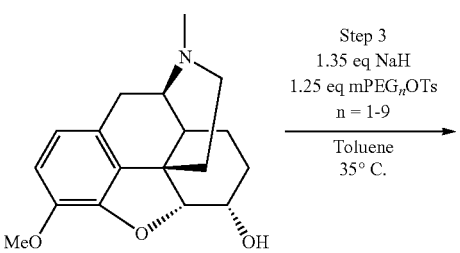

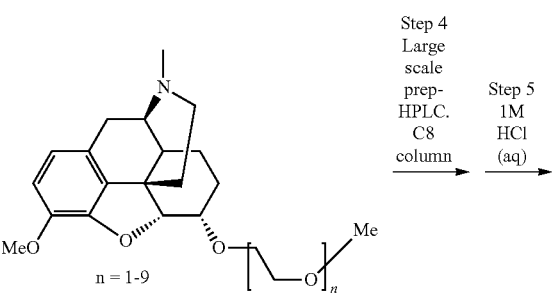

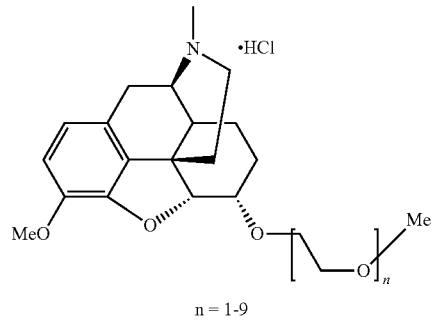

Preparation of the Hydrocodone Free Base

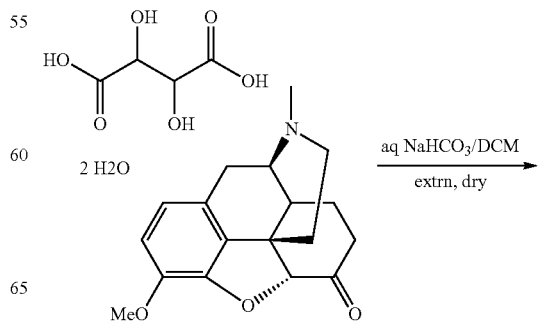

Preparation of 6-Hydrocodonol Free Base

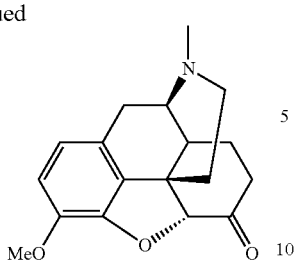

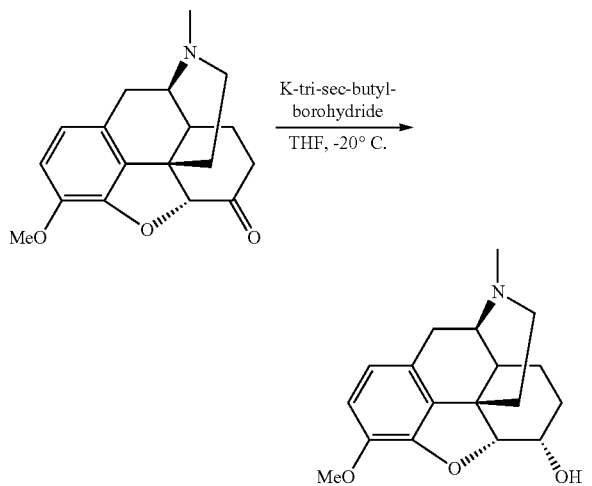

Hydrocodone bitartrate salt was dissolved in water. To this was added 2 equivalents solid NaHCO$_3$. Hydrocodone precipitates and dichlormethane was added. The biphasic solution was allowed to stir for twenty minutes. The layers were then separated and the basic aqueous layer was extracted two times with dichloromethane. The organic layer was dried over MgSO$_4$ and evaporated to yield hydrocodone free base as a white powder. Isolated yield was generally 95+%

Hydrocodone was dissolved in THF and cooled to −20° C. A solution of 1M K-Selectride in THF was added to the stirring solution dropwise over approximately one hour. When the reaction is complete, it was quenched with 5 equivalents of 1M HCl and the THF removed in vacuo. The solution was extracted three times with ethyl ether. The organic layers were discarded and the acid layer was made alkaline with K$_2$CO$_3$ and extracted three times with chloroform. The organic layer was evaporated to obtain the 6-hydrocodonol as a solid. Isolated yield was generally 95+%. Exp. Mass=301.4 M+H=302.5 Retention Time=0.79 minutes.

Preparation of 6-Hydrocodonol Alkylation with mPEG$_n$-OTs

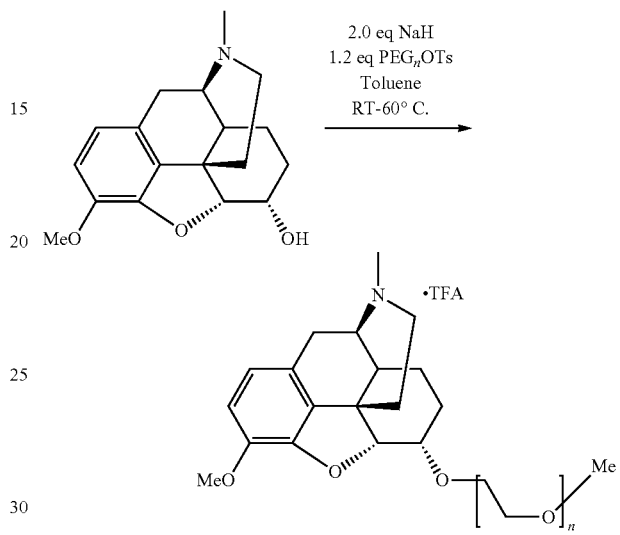

Hydrocodonol was dissolved in the minimum amount of anhydrous toluene possible with warming and sonication. To the room temperature solution was added 2 eq. NaH (60% dispersion in mineral oil) in portions with good stirring. The mixture was allowed to stir at room temperature for ten minutes, and then a solution containing 1.3 eq. of mPEG$_n$-OTs in toluene was added over five minutes. After 15 minutes at room temperature, the mixture was heated in a 60° C. oil bath overnight. LC-MS analysis showed complete consumption of starting materials. The mixture was quenched by pouring into water and toluene was removed in vacuo. The aqueous residue was extracted with CHCl$_3$ and the aqueous layer discarded. The combined organic layers were washed with ½ sat. NaHCO$_3$ and extracted with 1 M HCl (aq) with vigorous shaking. The combined aqueous layers were washed with CHCl$_3$ and concentrated in vacuo to give the crude product as a dark amber oil.

The residue was purified by reverse phase HPLC using a C8 column. Post purification yield was generally 25-50%, as shown in Table 13.

TABLE 13

Yields for Exemplary alpha-6-mPEG$_n$-O-Hydrocodonol Compounds

| Compound | Total Amount of Hydrocodonol Used (g, all batches) | Total Amount of Hydrocodonol Used (mmol, all batches) | Product Obtained as HCl salt (g) | Yield (mmol) | Yield (%) |
|---|---|---|---|---|---|
| α-6-mPEG$_1$-O-Hydrocodonol | 24.5 | 81.3 | 301.4 | 26.3 | 32.4% |
| α-6-mPEG$_2$-O-Hydrocodonol | 28 | 92.9 | 301.4 | 25.7 | 27.7% |
| α-6-mPEG$_3$-O-Hydrocodonol | 18 | 59.7 | 301.4 | 22.8 | 38.2% |
| α-6-mPEG$_4$-O-Hydrocodonol | 18 | 59.7 | 301.4 | 20.9 | 35.0% |
| α-6-mPEG$_5$-O-Hydrocodonol | 18 | 59.7 | 301.4 | 18.8 | 31.4% |
| α-6-mPEG$_6$-O-Hydrocodonol | 12 | 39.8 | 301.4 | 18.4 | 46.2% |

TABLE 13-continued

Yields for Exemplary alpha-6-mPEG$_n$-O-Hydrocodonol Compounds

| Compound | Total Amount of Hydrocodonol Used (g, all batches) | Total Amount of Hydrocodonol Used (mmol, all batches) | Product Obtained as HCl salt (g) | Yield (mmol) | Yield (%) |
|---|---|---|---|---|---|
| α-6-mPEG$_7$-O-Hydrocodonol | 18 | 59.7 | 301.4 | 24.0 | 40.2% |
| α-6-mPEG$_8$-O-Hydrocodonol | 26.4 | 87.6 | 301.4 | 16.0 | 18.3% |
| α-6-mPEG$_9$-O-Hydrocodonol | 17.24 | 57.2 | 301.4 | 8.4 | 14.7% |

Conversion to alpha-6-mPEG$_n$-O-Hydrocodonol Hydrochloride (n=1 through 9)

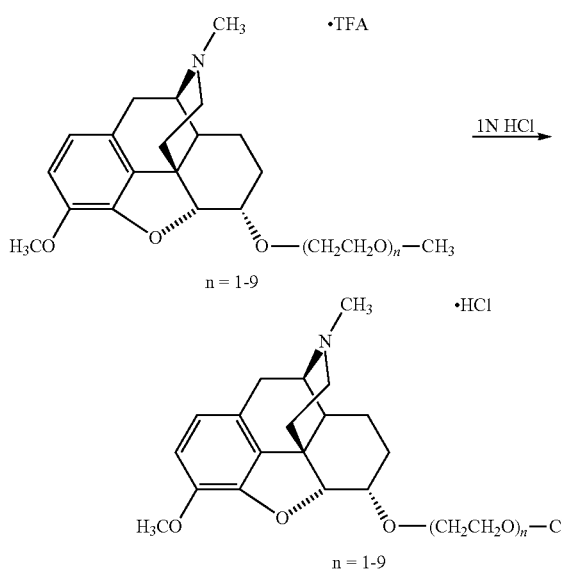

HPLC purified mPEG$_n$-hydrocodonol TFA salt was dissolved in 1 M HCl (aq) and concentrated in vacuo. The residue was again dissolved in 1 M HCl (aq) and concentrated in vacuo. The residue was azeotroped three times with acetonitrile to give mPEG$_n$-hydrocodonol HCl salt as a light amber glass The resulting material was purified through a C18 column (Phenomenex Kinetics 50×3.0), wherein the column temperature was 40° C., flow rate was 1.5 mL/minute, mobile phase A of 0.1% TFA/water and mobile phase B of 0.1% TFA/ACN, and the gradient following 5% B to 100% B over four minutes, with a stay at 100% B for one minute, then equilibration to 5% B over one minute. The purification results are provided in Table 14.

TABLE 14

Yields for Exemplary alpha-6-mPEG$_n$-O-Hydrocodonol Compounds

| Compound | MW | M + H | Retention Time (minute) |
|---|---|---|---|
| α-6-mPEG$_1$-O-Hydrocodonol | 359.5 | 360.5 | 1.17 |
| α-6-mPEG$_2$-O-Hydrocodonol | 403.5 | 404.5 | 1.00 |
| α-6-mPEG$_3$-O-Hydrocodonol | 447.6 | 448.0 | 1.06 |
| α-6-mPEG$_4$-O-Hydrocodonol | 491.6 | 492.5 | 1.10 |
| α-6-mPEG$_5$-O-Hydrocodonol | 535.7 | 536.5 | 1.16 |
| α-6-mPEG$_6$-O-Hydrocodonol | 579.7 | 580.5 | 1.19 |
| α-6-mPEG$_7$-O-Hydrocodonol | 623.8 | 624.5 | 1.22 |
| α-6-mPEG$_8$-O-Hydrocodonol | 667.8 | 668.5 | 1.19 |
| α-6-mPEG$_9$-O-Hydrocodonol | 711.9 | 713.0 | 1.25 |

Using conventional in vitro mu opioid receptor binding affinity assays, IC$_{50}$ values were determined for each of alpha-6-mPEG$_n$-O-hydrocodonol compounds. The results are provided in Table 15.

TABLE 15

Receptor Binding Data for Exemplary alpha-6-mPEG$_n$-O-Hydrocodonol Compounds

| Compound | Run 1 IC50 | Run 2 IC50 | Run 3 IC50 | MEAN IC50 | STDEV | Fold Change vs. Hydrocodone |
|---|---|---|---|---|---|---|
| Hydrocodone (+)-bitartrate salt | 5.33E-08 | 5.41E-08 | 8.36E-08 | 6.37E-08 | 1.73E-08 | 1.00 |
| α-6-Hydrocodonol | 5.53E-07 | 2.61E-07 | 6.19E-07 | 4.78E-07 | 1.91E-07 | 7.50 ↓ |
| α-6-mPEG$_1$-O-Hydrocodonol | 3.43E-07 | 1.66E-07 | 6.42E-07 | 3.84E-07 | 2.41E-07 | 6.03 ↓ |
| α-6-mPEG$_2$-O-Hydrocodonol | 2.55E-07 | 3.43E-07 | 5.19E-07 | 3.72E-07 | 1.34E-07 | 5.84 ↓ |
| α-6-mPEG$_3$-O-Hydrocodonol | 2.53E-07 | 3.46E-07 | 5.22E-07 | 3.74E-07 | 1.37E-07 | 5.87 ↓ |
| α-6-mPEG$_4$-O-Hydrocodonol | 1.37E-07 | 5.53E-07 | 6.74E-07 | 4.54E-07 | 2.82E-07 | 7.14 ↓ |
| α-6-mPEG$_5$-O-Hydrocodonol | 3.18E-07 | 3.51E-07 | 5.16E-07 | 3.95E-07 | 1.06E-07 | 6.20 ↓ |
| α-6-mPEG$_6$-O-Hydrocodonol | 9.20E-07 | 4.29E-07 | 7.75E-07 | 7.08E-07 | 2.52E-07 | 11.12 ↓ |
| α-6-mPEG$_7$-O-Hydrocodonol | 2.52E-06 | 6.86E-07 | 1.82E-06 | 1.68E-06 | 9.25E-07 | 26.32 ↓ |
| α-6-mPEG$_8$-O-Hydrocodonol | 5.05E-06 | 1.04E-06 | 1.57E-06 | 2.55E-06 | 2.18E-06 | 40.10 ↓ |
| α-6-mPEG$_9$-O-Hydrocodonol | 1.35E-06 | 3.74E-07 | 1.39E-06 | 1.04E-06 | 5.75E-07 | 16.30 ↓ |

What is claimed is:
1. An opioid agonist compound according to Formula I-Ca:

Formula I-Ca wherein:
R² is OH;
R³ is methyl;
R⁴ is H;
R⁵ is —C(O)—;
Y¹ is —O—;
the dotted line ("- - -") is absent;
X is a single bond, —C(O)O—, —OC(O)—, —CH₂C(O)O—, —CH₂OC(O)—, —C(O)OCH₂—, —OC(O)CH₂—, —O—, —NH—, —S—, —C(O)—, —C(O)NH—, —NHC(O)NH—, —OC(O)NH—, —C(S)—, —CH₂—, —CH₂CH₂—, —CH₂CH₂CH₂—, —CH₂CH₂CH₂CH₂—, —OCH₂—, —CH₂O—, —OCH₂CH₂—, —CH₂OCH₂—, —CH₂CH₂O—, —OCH₂CH₂CH₂—, —CH₂OCH₂CH₂—, —CH₂CH₂OCH₂—, —CH₂CH₂CH₂O—, —OCH₂CH₂CH₂CH₂—, —CH₂OCH₂CH₂CH₂—, —CH₂CH₂OCH₂CH₂—, —CH₂CH₂CH₂OCH₂—, —CH₂CH₂CH₂CH₂O—, —C(O)NHCH₂—, —C(O)NHCH₂CH₂—, —CH₂C(O)NHCH₂—, —CH₂CH₂C(O)NH—, —C(O)NHCH₂CH₂CH₂—, —CH₂C(O)NHCH₂CH₂—, —CH₂CH₂C(O)NHCH₂—, —CH₂CH₂CH₂C(O)NH—, —C(O)NHCH₂CH₂CH₂CH₂—, —CH₂C(O)NHCH₂CH₂CH₂—, —CH₂CH₂C(O)NHCH₂CH₂—, —CH₂CH₂CH₂C(O)NHCH₂—, —CH₂CH₂CH₂CH₂C(O)NH—, —NHC(O)CH₂—, —CH₂NHC(O)CH₂—, —CH₂CH₂NHC(O)CH₂—, —NHC(O)CH₂CH₂—, —CH₂NHC(O)CH₂CH₂—, —CH₂CH₂NHC(O)CH₂CH₂—, —C(O)NHCH₂—, —C(O)NHCH₂CH₂—, —OC(O)NHCH₂—, —OC(O)NHCH₂CH₂—, —NHCH₂—, —NHCH₂CH₂—, —CH₂NHCH₂—, —CH₂CH₂NHCH₂—, —C(O)CH₂—, —C(O)CH₂CH₂—, —CH₂C(O)CH₂—, —CH₂CH₂C(O)CH₂—, —CH₂CH₂C(O)CH₂CH₂—, —CH₂CH₂C(O)—, —CH₂CH₂CH₂C(O)NHCH₂CH₂NH—, —CH₂CH₂CH₂C(O)NHCH₂CH₂NHC(O)—, —CH₂CH₂CH₂C(O)NHCH₂CH₂NHC(O)CH₂—, a bivalent cycloalkyl group, or —N(R⁶)—;
R⁶ is H, alkyl, substituted alkyl, alkenyl, substituted alkenyl, alkynyl, substituted alkynyl, aryl, or substituted aryl; and POLY is a poly(ethylene oxide) having from about 1 to about 30 monomers.
2. The compound of claim 1, wherein POLY possess from about 1 to about 10 monomers.
3. The compound of claim 1, wherein POLY possess 1 monomer.
4. The compound of claim 1, wherein POLY possess 2 monomers.
5. The compound of claim 1, wherein POLY possess 3 monomers.
6. The compound of claim 1, wherein POLY possess 4 monomers.
7. The compound of claim 1, wherein POLY possess 5 monomers.
8. The compound of claim 1, wherein POLY possess 6 monomers.
9. The compound of claim 1, wherein POLY possess 7 monomers.
10. The compound of claim 1, wherein POLY possess 8 monomers.
11. The compound of claim 1, wherein POLY possess 9 monomers.
12. The compound of claim 1, wherein POLY possess 10 monomers.
13. The compound of claim 1, wherein POLY is a methoxy end-capped poly(ethylene oxide).
14. A composition comprising:
(i) a compound of claim 1; and
(ii) optionally, a pharmaceutically acceptable excipient.
15. A dosage form comprising a compound of claim 1.
16. A method of treating pain comprising administering a compound of claim 1 to a patient in need thereof.
17. The compound of claim 1, wherein X is a single bond, —O—, or —OC(O)CH₂O—.
18. The compound of claim 1 according to either of the following formulas:

wherein n is an integer from 1-30.

* * * * *